United States Patent
Blauert et al.

(10) Patent No.: US 12,166,275 B2
(45) Date of Patent: Dec. 10, 2024

(54) BIO-MATCHED ANTENNA

(71) Applicant: OHIO STATE INNOVATION FOUNDATION, Columbus, OH (US)

(72) Inventors: John Blauert, Columbus, OH (US); Asimina Kiourti, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 0 days.

(21) Appl. No.: 18/311,647

(22) Filed: May 3, 2023

(65) Prior Publication Data
US 2023/0275342 A1  Aug. 31, 2023

Related U.S. Application Data

(63) Continuation of application No. 17/261,963, filed as application No. PCT/US2019/043060 on Jul. 23, 2019, now Pat. No. 11,664,585.
(Continued)

(51) Int. Cl.
*H01Q 1/27* (2006.01)
*A61B 5/00* (2006.01)
(Continued)

(52) U.S. Cl.
CPC ......... *H01Q 1/273* (2013.01); *A61B 5/0031* (2013.01); *A61N 1/37229* (2013.01); *H01Q 13/02* (2013.01)

(58) Field of Classification Search
CPC ...... H01Q 1/273; H01Q 13/02; A61B 5/0026; A61B 5/0028; A61B 5/0031;
(Continued)

(56) References Cited

U.S. PATENT DOCUMENTS 5,563,616 A  10/1996 Dempsey et al.
6,115,636 A   9/2000 Ryan
(Continued)

OTHER PUBLICATIONS

International Search Report and Written Opinion dated Oct. 22, 2019 in co-pending PCT Application No. PCT/US2019/043060.
(Continued)

*Primary Examiner* — Robert Karacsony
(74) *Attorney, Agent, or Firm* — Thomas | Horstemeyer, LLP

(57) ABSTRACT

An on-body antenna is provided that overcomes mismatch loss problems associated with current on-body antennas and is capable of operating over a wide range of frequencies with low transmission loss. At least a first antenna element of the on-body antenna is configured to receive an oscillating electric current and to radiate an oscillating electromagnetic field over a predetermined range of frequencies. The first antenna element is made of non-electrically-conductive material having a first relative permittivity. At least a second material having a second relative permittivity can be disposed on or in the first antenna element. Disposing the second material provides the first antenna element with an effective permittivity that can be closely matched to a frequency-dependent permittivity of biological tissue of a subject. The first non-electrically-conductive material and the second material can be preselected to have relative permittivities that allow anisotropy to be achieved.

25 Claims, 41 Drawing Sheets

Related U.S. Application Data

(60) Provisional application No. 62/702,105, filed on Jul. 23, 2018.

(51) Int. Cl.
  *A61N 1/372* (2006.01)
  *H01Q 13/02* (2006.01)

(58) Field of Classification Search
  CPC .......... A61B 18/1815; A61B 2018/183; A61B 2018/1838; A61B 2018/1846; A61B 2018/1853; A61B 2018/1884; A61N 1/37229
  See application file for complete search history.

(56) References Cited

U.S. PATENT DOCUMENTS

| | | | |
|---|---|---|---|
| 6,489,931 | B2 | 12/2002 | Liu |
| 6,879,297 | B2 | 4/2005 | Brown et al. |
| 6,930,602 | B2 | 8/2005 | Villaseca et al. |
| 7,878,207 | B2 | 2/2011 | Goetz et al. |
| 8,059,034 | B2 | 11/2011 | Ly et al. |
| 9,254,393 | B2 | 9/2016 | Perryman et al. |
| 11,664,585 | B2 * | 5/2023 | Blauert .............. A61N 1/37229 343/718 |
| 2004/0189528 | A1 | 9/2004 | Killen et al. |
| 2009/0267858 | A1 | 10/2009 | Itsuji |
| 2010/0228244 | A1 * | 9/2010 | Hancock ............ A61B 18/1815 606/33 |
| 2017/0360323 | A1 | 12/2017 | Li et al. |

OTHER PUBLICATIONS

Tak et al., "Dual-Band On-Body Repeater Antenna for In-on-On WBAN Applications", Intl J. Anennas Propagation, vol. 2013, Art. ID 107251, pp. 1-12, http://dx.doi.org/10.115/2013/107251.

Blauert, John, "Bio-Matched Horn: A Novel 1-9 GHz On-Body Antenna for Low-Loss Biomedical Telemetry with Implants", Paper submitted to IEEE, Apr. 2018.

C.W. L. Lee et al., "A high-sensitivity fully-passive neurosensing system for wireless brain signal monitoring," IEEE Transactions on Microwave Theory and Techniques , vol. 63, No. 6, pp. 2060-2068, Jun. 2015.

A. Kiourti et al., "A broadband implantable and a dual-band onbody repeater antenna: design and transmission performance," IEEE Transactions on Antennas and Propagation, vol. 62, No. 6, pp. 2899-2908, Jun. 2014.

J. Felicio et al., "Dual-Band Skin-Adhesive Repeater Antenna for Continuous Body Signals Monitoring," IEEE Journal of Electromagnetics, RF and Microwaves in Medicine and Biology, vol. 2, No. 1, pp. 25-32, Mar. 2018.

E. Chow et al., "Evaluation of Cardiovascular Stents as Antennas for Implantable Wireless Applications" IEEE Transactions on Microwave Theory and Techniques, vol. 57, No. 10, pp. 2523-2532, Oct. 2009.

H. Bahrami et al., "Flexible, Polarization-Diverse UWB Antennas for Implantable Neural Recording Systems," IEEE Transactions on Biomedical Circuits and Systems, vol. 10, No. 1, pp. 38-48, Feb. 2016.

Klemetsen O, "Design and Evaluation of a Medical Microwave Radiometer for Observing Temperature Gradients Subcutaneously in the Human Body." Dissertation for University of Tromso, 2011.

Amineh, R. "Tem Horn Antenna for Ultra-Wide Band Microwave Breast Imaging", Progress in Electromagnetics Research B, Jan. 2009, https://www.researchgate.net/publications/277111695.

Carr, "Microwave Radiometry: Its Importance to the Detection of Cancer", IEEE Transactions on Microwave Theory and Techniques, vol. 37, No. 12, Dec. 1989, pp. 1862-1869.

B. Sanz-Izquierdo et al., "WLAN Antenna on 3D Printed Bracelet and Wrist Phantom", 2014 Loughborough Antennas and Propagation Conference (LAPC), Nov. 10-11, 2014, UK, DOI: 10.1109/LAPC.2014.6996400.

Van Roon et al., "A 433 MHz Lucite Cone Waveguide Applicator for Superficial Hyperthermia," International Journal of Hyperthermia, 14:1, 13-27, DOI: 10.3109/02656739809018211, https://doi.org/10.3019/02656739809018211.

* cited by examiner

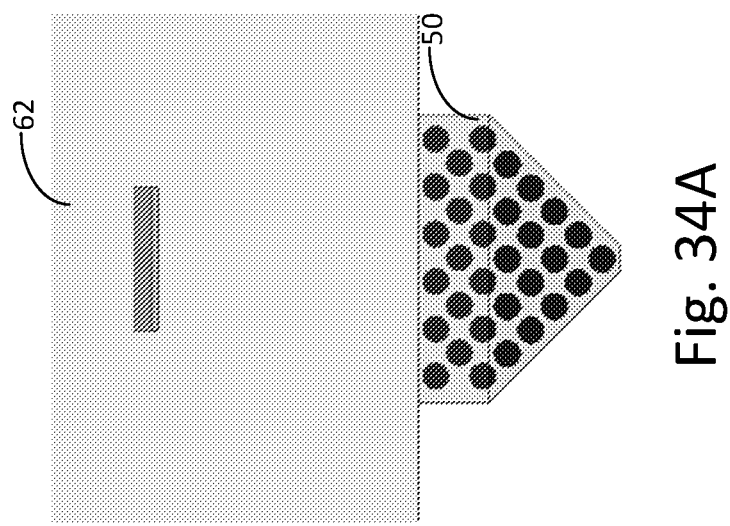

BIO-MATCHED ANTENNA

CROSS-REFERENCE TO RELATED APPLICATIONS

This application is a continuation of copending application Ser. No. 17/261,963, filed Jan. 21, 2021, which is a nonprovisional PCT international application that claims priority to, and the benefit of the filing date of, U.S. Provisional Application having Ser. No. 62/702,105, filed on Jul. 23, 2018 and entitled "A BIO-MATCHED ANTENNA," which is hereby incorporated by reference herein in its entirety.

TECHNICAL FIELD

The present disclosure relates to antennas. More particularly, the invention relates to wearable, or on-body, antennas.

BACKGROUND

Radio frequency (RF) devices, including wearables and implants, play a key role in emerging medical technologies. Many of these devices, such as radiometers and wireless implants, rely on into-body radiation. Specifically, medical radiometry is a non-invasive imaging/sensing technology that allows for improved detection of core body temperature [1]-[3] and breast cancer [4] through monitoring RF radiation from the body. As another example of into-body radiators, implanted medical devices, such as neural implants [5], pacemakers [6], and glucometers/insulin pumps [7]-[8], can be made more ubiquitous through efficient wireless links with into-body radiators. In turn, extensive research has been conducted into efficient implanted antennas that can communicate from within the body to outside of it for implant telemetry [9]-[17] and/or wireless charging [18]. As expected, the aforementioned medical technologies necessitate robust, wideband and high gain wearable antennas to act as into-body radiators. Such features will eventually allow for high-sensitivity radiometers and high data-rate telemetry links for implants.

To date, very few works have reported into-body radiators for radiometry applications, and most of them do not address transmission loss aspects, as shown below in Table I. Instead, radiometry research focuses primarily on antenna bandwidth and backend signal processing to interpret the received thermal radiation. In contrast, works on into-body radiators intended for telemetry with implants often provide data link efficiency for benchmarking performance. Table II provides an overview of such state-of-the-art into-body antennas and their associated performance.

TABLE I

Into-Body Radiators for Radiometry: Comparison of Proposed Design vs. the State of The Art

| Ref. | Size/Antenna Type | Phantom Used | Bandwidth |
|---|---|---|---|
| [1] | $\pi \times 12.5^2 \times 4.45$ mm$^3$/Spiral | Chemical phantoms to represent brain | 1.1-1.6 GHz |
| [2] | $40 \times 10 \times 5$ mm$^3$/Biconical Patch | Simulation of breast tissue | 1-4 GHz |
| [3] | $40 \times 40 \times 2.54$ mm$^3$/Patch | Salmon/water to represent skin/muscle | 1.4-1.427 GHz |
| [4] | $21 \times 27 \times {\sim}30$ mm$^3$/Waveguide | Chemical phantoms to represent brain | 1-4 GHz |
| This work | $24.9 \times 24.9 \times 11.95$ mm$^3$/BMA | Beef/POPEYE | 1.07-11.9 GHz |

As seen below in Table II, several implant communication systems utilize off-body radiators, i.e., radiators that are separated from the patient by a sizeable air gap. However, the immense mismatch between biological tissues and free space adds an additional insertion loss. Indeed, air-tissue mismatch loss for a cardiac model wireless link operating at 2.4 Gigahertz (GHz) has been found to be as high as 17.5 decibels (dB). To mitigate this mismatch loss, research has been conducted on wearable, into-body antennas that make direct contact with the body. Most designs are relatively two-dimensional, utilizing a modified patch antenna milled from printed circuit board laminates. However, such antennas still have numerous issues to overcome, including: (a) mismatch at the biological tissue and antenna interface, (b) environmental and inter-subject variability, (c) frequency-dependent tissue properties, and (d) inherent material loss of biological tissues.

TABLE II

Into-Body Radiators for Telemetry: Comparison of Proposed Design vs. the State of The Art

| Ref. | Frequency | Implantation Depth | Air Gap | Size/Antenna Type | Bandwidth | Transmission Loss |
|---|---|---|---|---|---|---|
| [9] | 2.4 GHz | 3.3 mm | 4 mm | $\pi \times 72.5^2 \times 13.635$ mm$^3$/Spiral | 0.6-6 GHz | 26 dB |
|  | 4.8 GHz | 3.3 mm | 4 mm | $\pi \times 72.5^2 \times 13.635$ mm$^3$/Spiral | 0.6-6 GHz | 19 dB |
| [10] | 400 MHz | 4 mm | 5 cm | 375 mm/Dipole | NA | 34 dB |
|  | 2.4 GHz | 4 mm | 5 cm | 62.4 mm/Dipole | NA | 32 dB |
| [11] | 2.4 GHz | 3.5 cm | 10 cm | NA/Free-Space Horn | 0.9-2.45 GHz | 56.5 dB |
| [12] | 400 MHz | 1 cm | 1.5 cm | $70 \times 60 \times 1.6$ mm$^3$/Patch | 350-450 MHz | 50 dB |
| [13] | 2.4 GHz | 5 cm | 2.55 m | NA/Free-Space Horn | NA | 81 dB |
| [14] | 2.4 GHz | 4 mm | 0 cm | $26.3 \times 30 \times 1.6$ mm$^3$/Spiral | 2-11 GHz | 22.5 dB |
| [15] | 400 MHz | 9 mm | 0 cm | $28 \times 26.8 \times 0.635$ mm$^3$/Patch | 380-470 MHz | 24 dB |
| [16] | 2.4 GHz | 2 cm | 0 cm | $\pi \times 17.5^2 \times 0.76$ mm$^3$/Exponentially Tapered Slot | 2.35-2.7 GHz | 30 dB |
| [17] | 2.4 GHz | 2 cm | 0 cm | $22 \times 22 \times 10$ mm$^3$/BMA | 1.4-8.5 GHz | 19.2 dB |
| This work | 2.4 GHz | 3 cm | 0 cm | $24.9 \times 24.9 \times 11.95$ mm$^3$/BMA | 1.07-11.9 GHz | 21.4 dB |

Accordingly, a need exists for an on-body, or wearable, antenna that overcomes the aforementioned issues associated with (a) mismatch at the biological tissue and antenna interface, (b) environmental and inter-subject variability, (c) frequency-dependent tissue properties, and (d) inherent material loss of biological tissues.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 7 is a plot of isofrequency contours for the BMA shown in FIG. 1 for the unit cell size, a, divided by the free space wavelength, $\lambda_0$, for various wave vectors ($k_x$, $k_z$) scaled by the unit cell size, a.

FIG. 34A is a side plan view of the BMA simulation setup in accordance with another representative embodiment equipped with a small buffer lens that is made of the same dielectric material that is used to make the antenna.

DETAILED DESCRIPTION

Figure 1:
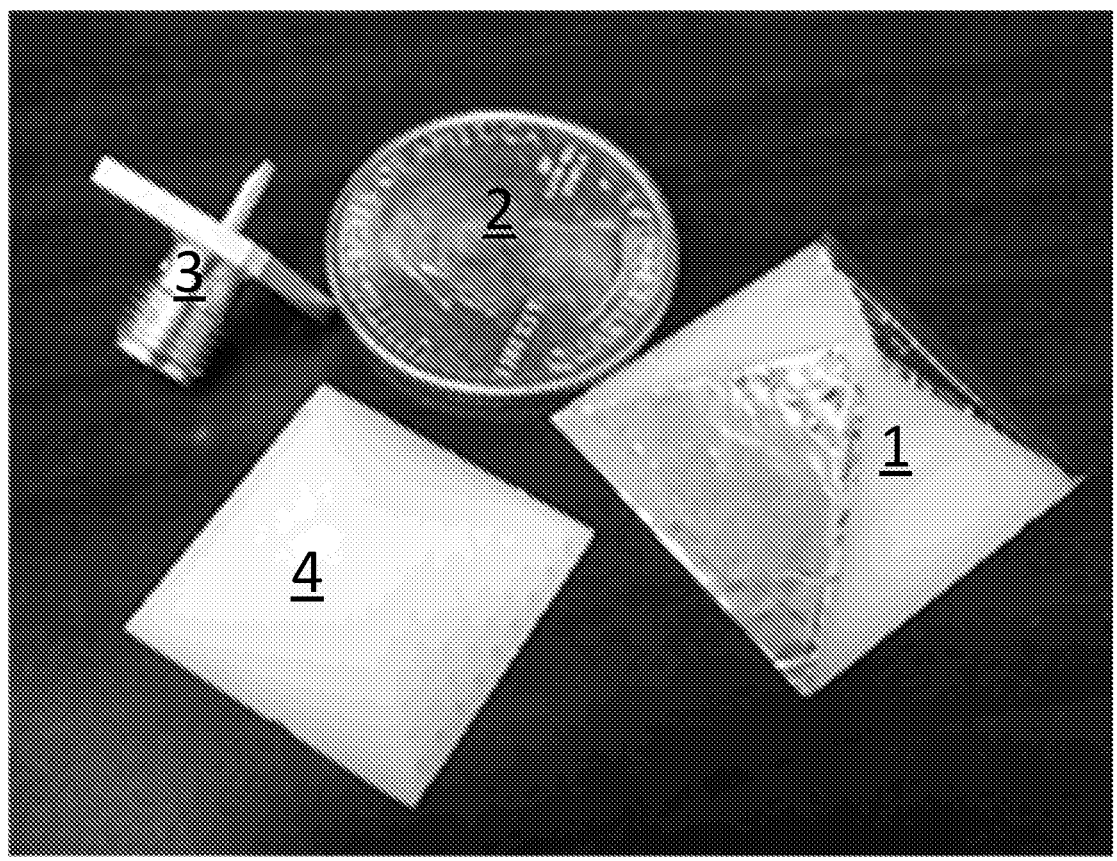
FIG. 1 is a photograph showing a fabricated Bio-Matched Antenna (BMA), a quarter coin, a Sub-Miniature Version A (SMA) connector and the engineered dielectric structure of the fabricated BMA.

The present disclosure discloses an on-body, or wearable, bio-matched antenna that overcomes the aforementioned issues and that is capable of operating over a wide range of frequencies with high gain. At least a first antenna element of the wearable bio-matched antenna is configured to receive an oscillating electric current and to radiate an oscillating electromagnetic field over a predetermined range of frequencies. The oscillating electromagnetic field has a predetermined beam shape and directionality. The first antenna element is made at least partially of at least a first non-electrically-conductive material having a first relative permittivity. At least a second material is disposed on or in the first antenna element at one or more predetermined locations on or in the first antenna element. The second material has a second relative permittivity. Disposing the second material on or in the first antenna element at one or more predetermined locations provides the first antenna element with an effective permittivity that is closely matched, over the predetermined range of frequencies, to a frequency-dependent permittivity of skin of a subject. An electrically-conductive material at least partially covers at least a first side of the first antenna element.

To address the aforementioned issues associated with state-of-the-art antennas: (a) mismatch at the biological tissue and antenna interface, (b) environmental and inter-subject variability, (c) frequency-dependent tissue properties, and (d) inherent material loss of biological tissues concerns, the above-referenced U.S. provisional application Ser. No. 62/702,105 disclosed a bio-matched antenna (BMA) that utilizes an engineered periodic dielectric composed of plastic and water to match to biological tissues over a wide bandwidth with high gain. Subject matter of this provisional application was also disclosed in an article by J. Blauert and A. Kiourti, entitled "Bio-Matched Horn: A Novel 1-9 GHz On-Body Antenna for Low-Loss Biomedical Telemetry with Implants," published in IEEE Transactions on Antennas and Propagation, Early Access, December 2018 (hereinafter referred to as "the article"). This BMA was shown to operate over a wide bandwidth ranging from 1.4 to 8.5 GHz with 10.8 dB less transmission loss than the state-of-the-art antennas at 2.4 GHz. The high gain in combination with the remarkably wide bandwidth of this BMA allows for robust RF transmission through biological tissues.

In the following, a comprehensive theoretical framework is disclosed that demonstrates that the inventive principles and concepts of the BMA disclosed in the aforementioned U.S. provisional application and in the corresponding article apply to, and can be used to design, a full class of antennas. We refer to these antennas herein as BMAs: a new class of wearable, high-gain, wideband antennas that can be fine-tuned according to design guidelines introduced in this disclosure to fit numerous into-body applications. It is worth clarifying here that the initial prototype of was referred to as a bio-matched horn based upon design shape and appearance. However, traditional metal-waveguide-excited horn antennas operate differently than the BMAs, which are more closely related to a conical antenna. In order to avoid confusion, the new class of antennas shall be referred to herein as BMAs.

The theoretical framework disclosed herein includes the fundamental governing equations behind the BMA's performance that will allow custom designs with optimized performance for various application scenarios to be achieved. For example, larger BMAs can operate at lower frequencies, but have higher loss at higher frequencies as compared to smaller BMAs. As another example, increasing the unit cell size allows for easier manufacturing and quicker simulation times, but lowers the high frequency cutoff.

In the following, simulation results are reported that are further validated by in vitro measurements using tissue-emulating phantoms. To validate and demonstrate the utility of the theoretical framework disclosed herein, the design, fabrication and measurement of a BMA with 6.2 dB less transmission loss and a 11.12:1 as opposed to a 6.07:1 bandwidth than what is disclosed in the aforementioned article at a minimal increase in antenna dimensions. Comparison vs. the state of the art is shown above in Tables I and II.

I. BMA Model and Design Parameters

Figure 2A:
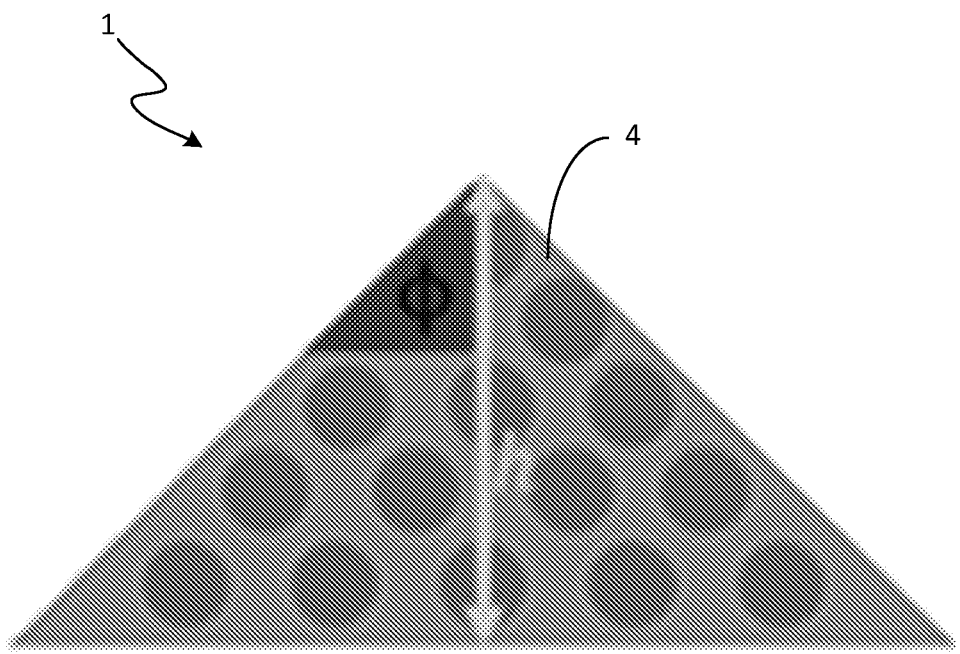
FIG. 2A shows a cross-sectional side view diagram of the engineered dielectric structure shown in FIG. 1.
Figure 2B:
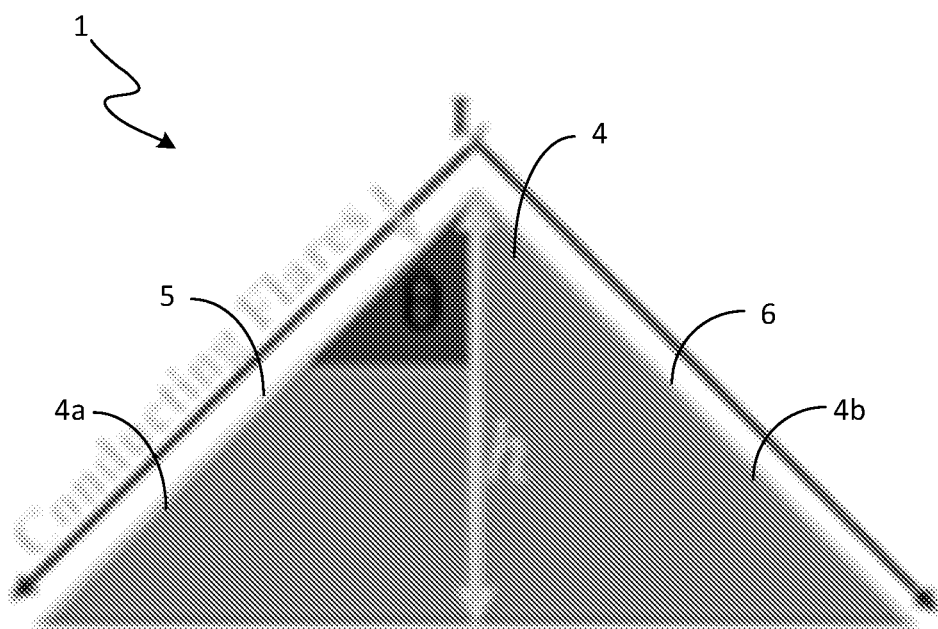
FIG. 2B shows a cross-sectional side view diagram of the BMA shown in FIG. 1.

FIG. 1 is a photograph showing a fabricated BMA 1, a quarter coin 2, a Sub-Miniature Version A (SMA) connector 3 and the engineered dielectric structure 4 of the fabricated BMA 1. FIG. 2A shows a cross-sectional side view diagram of the engineered dielectric structure 4 shown in FIG. 1. FIG. 2B shows a cross-sectional side view diagram of the BMA 1 shown in FIG. 1. The BMA 1 comprises the engineered dielectric structure 4 and first and second electrically-conductive flares 5 and 6, respectively, that are disposed on first and second opposite sides 4a and 4b, respectively, of the engineered dielectric structure 4 at ascending angles $\theta$ and $\phi$, respectively. Unless specified otherwise, the ascent angle is uniform in both directions and is referred to solely as $\theta$.

The BMA 1 can be excited via the SMA connector 3 being applied along the top of the BMA 1 with the pin of the connector 3 touching one of the flares 5, 6 and the ground plane touching the other of the flares 5, 6. The pyramidal shape of the BMA 1 allows for the BMA 1 to behave like a dielectrically-loaded conical antenna, enabling wide bandwidth and high gain. The height, h, of the BMA 1 governs how much the antenna extends from the body of the subject or patient (not shown). The edge length, L, of the BMA 1 is the maximum length that the electrically-conductive material (e.g., copper) of the flares 5, 6 extends along each of the sides 4a and 4b.

The engineered dielectric structure 4 is bio-matched to the biological tissue of the patient and plays a central role in designing the BMA, as will be described below in detail. As is well known in the art, the electrical properties (permittivity and conductivity) of biological tissues are heavily influenced by their high water content. With this in mind, in accordance with an embodiment, the engineered dielectric structure 4 is engineered to mimic the properties of biological tissues through a periodic distribution of water surrounded by plastic. The unit cell (fundamental repeating structure) of the engineered dielectric structure 4 can take on different forms as will be discussed in Section II.

II. Engineering the Bio-Matched Dielectric

A. Benefits of Anisotropy

When engineering the dielectric structure 4 to match to biological tissues, the designer has the freedom to design the dielectric to be isotropic or anisotropic. Having a high permittivity in the plane orthogonal to propagation (i.e., in the X-Y plane of the Cartesian coordinate system shown in FIG. 3), and a low permittivity in the direction of propagation (i.e., in the Z-direction) will improve the gain of the BMA. To test this hypothesis, BMAs were simulated with dielectrics that were manually defined to be isotropic or anisotropic, and their performance was compared. For the isotropic case, the dielectric was defined to emulate the skin's permittivity in all directions. For the anisotropic case, the dielectric was defined to emulate the skin's permittivity perpendicular to the direction of propagation (i.e., in the X-Y plane shown in FIG. 3) and a lower permittivity ($\varepsilon r=10$) in the direction of propagation (i.e., in the Z-direction shown in FIG. 3).

Figure 3:
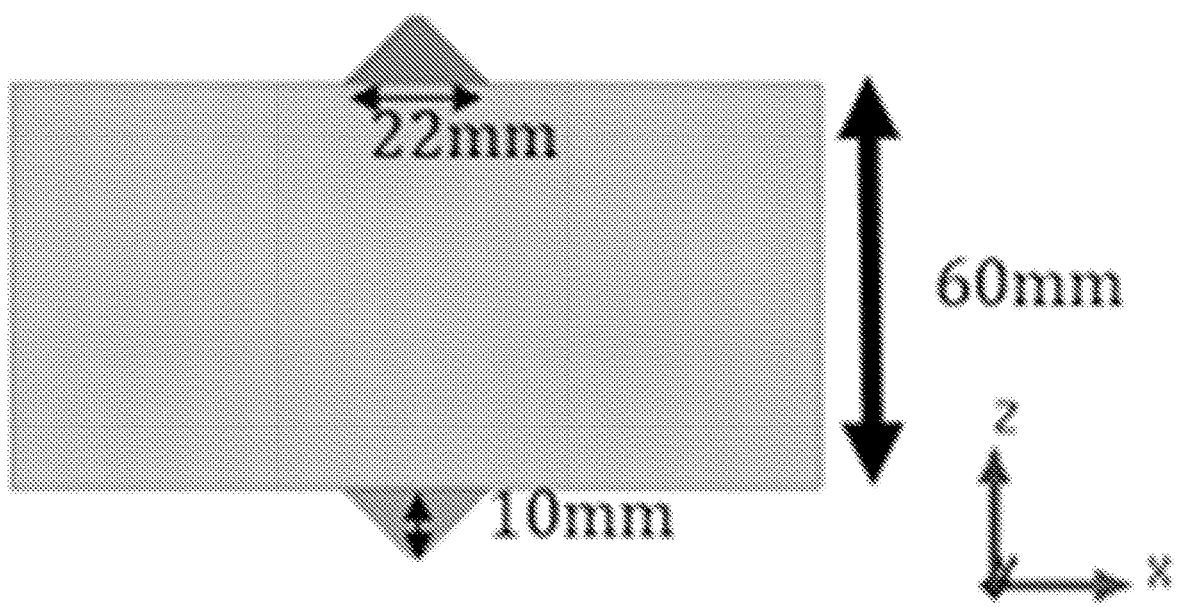
FIG. 3 shows a simulation setup for the simulating the BMA shown in FIGS. 1-2B.

Simulations were carried out in ANSYS High Frequency Structure Simulator (HFSS) using the setup of FIG. 3. As seen, two BMAs were employed, separated by a 60-mm-thick material emulating skin tissue. Skin tissue was chosen because it is comparable in properties to ground beef and ⅔ muscle, both of which have been extensively used in the literature to emulate the average human body properties. Both BMAs are of the same size as the BMA discussed in the aforementioned article.

Figure 4:
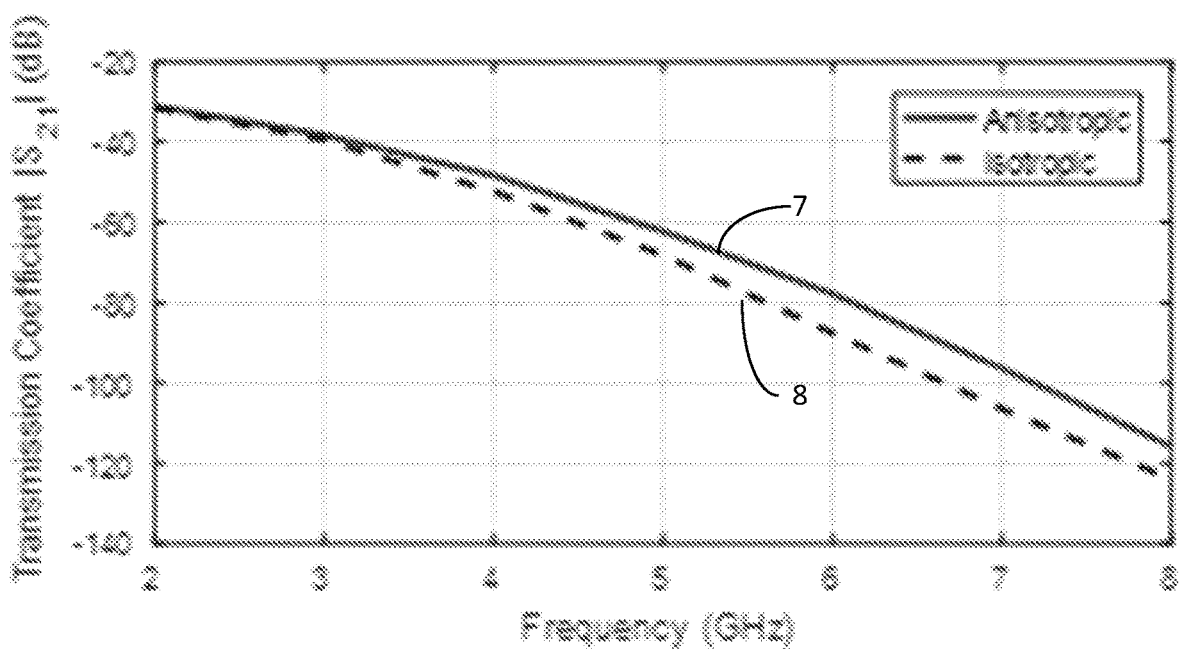
FIG. 4 is a plot of the simulated transmission coefficient results in decibels (dB) as a function of frequency in GHz obtained using the simulation setup shown in FIG. 3.

FIG. 4 is a plot of the simulated transmission coefficient results in decibels (dB) as a function of frequency in GHz. The simulated transmission coefficient results indicate that the anisotropic permittivities, which correspond to curve 7, achieve better transmission across the bandwidth than the isotropic permittivities, which correspond to curve 8. This is attributed to the orientation of the permittivities so that only the desired direction of propagation has a high permittivity path in the orthogonal plane.

B. Development of Anisotropy

Figures 5A, 5B:
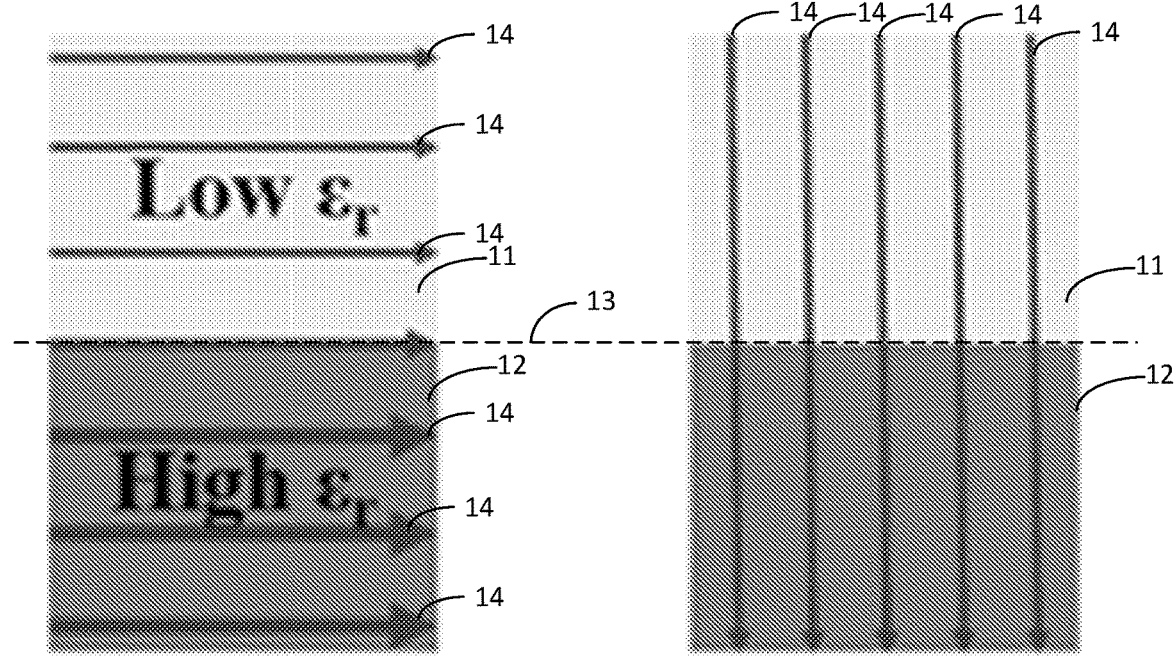
FIGS. 5A and 5B show dielectric materials of both low and high relative permittivity and demonstrate the manner in which electric flux develops differently in anisotropic and isotropic materials.

Since anisotropic dielectric materials are shown to perform better than the isotropic dielectric materials, then another consideration is how to achieve anisotropy. One way to achieve anisotropy is through manipulating the orientation of materials of differing permittivity. In this embodiment, these materials are selected to be plastic and water for reasons set forth above in Section I. FIGS. 5A and 5B show dielectric materials of low and high relative permittivity 11 and 12, respectively. Dashed line 13 represents the boundary between the dielectric materials of low and high relative permittivity 11 and 12, respectively. Lines 14 represent the electric flux. FIGS. 5A and 5B show how the electric flux 14 develops differently depending on direction. Since the electric flux 14 does not vary in the medium, an electric field applied to the medium will have a higher flux when having parallel paths of different dielectrics (shown in FIG. 5A) as opposed to being applied orthogonally through multiple media (shown in FIG. 5B). This principle is also the reason why series capacitors result in a lower capacitance than in a parallel arrangement. Periodic distribution of a fundamental unit cell that has anisotropy due to such high and low flux paths will create an effective anisotropic medium. By controlling the ratio of high to low permittivity materials, the effective permittivity can be designed to match to a propagating medium.

C. Unit Cell Choice and Design

Figures 6A, 6B, 6C:
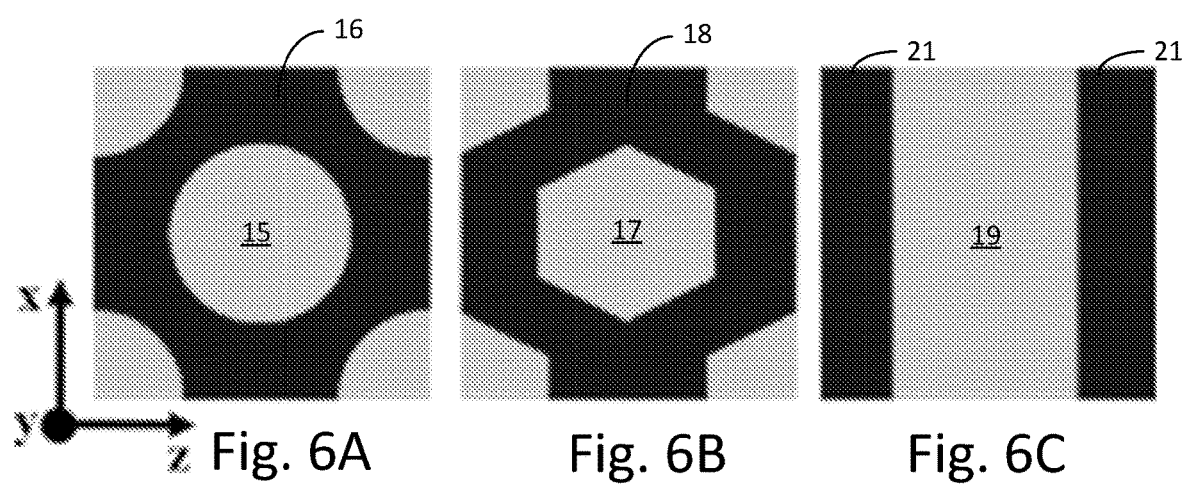
FIGS. 6A-6C show examples of various designs for the unit cells of the BMA shown in FIG. 1, such as, for example, cylindrical, hexagonal, and rectangular, respectively.

FIGS. 6A-6C show examples of various designs for the unit cells of the BMA, such as, for example, cylindrical, hexagonal, and rectangular, respectively. Areas in FIGS. 6A-6C having of different levels of darkness indicate materials of different permittivities (water in light areas, plastic in dark areas).

Referring to FIG. 6A, the unit cell employed in the prototype disclosed in the provisional application and in the aforementioned article was a cylindrical water unit cell 15 surrounded by plastic 16. However, other unit cells can be designed, such as hexagonal water unit cells 17 surrounded by plastic 18 and rectangular water unit cells 19 surrounded by plastic 21, as shown in FIGS. 6B and 6C, respectively. The key merits of different unit cell designs lie in miniaturization and anisotropy. Miniaturization increases the high frequency cutoff and will be discussed further in Section III-B, while anisotropy improves transmission as indicated previously in Section II-A.

In brief, hexagonal unit cells are superior to cylindrical unit cells in both miniaturization and anisotropy considerations. Rectangular unit cells offer comparable anisotropy to cylindrical unit cells, but enable a much higher degree of miniaturization than both cylindrical and hexagonal designs. Here, it is worth nothing that all three unit cells of FIGS. 6A-6C are uniaxial in design, meaning they have one permittivity direction that is abnormal to the rest. However, they differ in type of birefringence (degree of anisotropy) developed. Hexagonal and cylindrical unit cells have positive birefringence, since the high permittivity path is solely in the Y-direction. In contrast, rectangular unit cells have negative birefringence, since both the X- and Y-directions have high permittivity paths and the Z-direction has a low permittivity path.

D. Analysis of the Anisotropic Behavior

The Plane Wave Expansion Method (PWEM), which is known in the art, is used herein to analyze the anisotropic behavior of the bio-matched engineered dielectric structure of the BMA. The method solves Maxwell's equations in Fourier space, and, since the material is periodic, separates its operation across various frequencies into different bands. The first band can be considered as the effective medium band, and typically covers free-space wavelengths under ~0.05a, where "a" is the unit cell size. Depending on unit cell type, the first band cutoff can vary around this general estimate.

Figure 7:
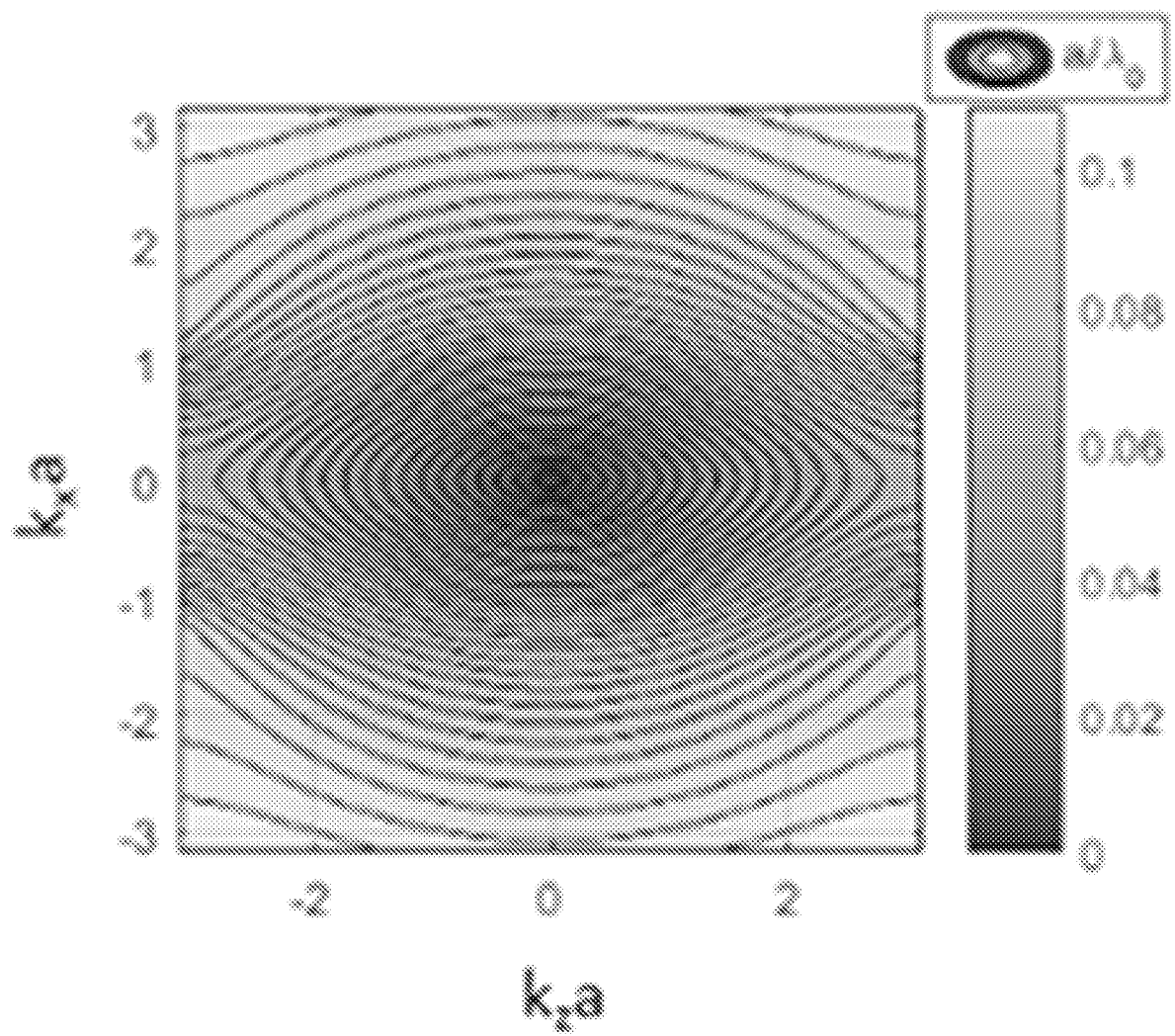

More specifically, the PWEM solves for the potential wave vectors for a given material structure. Here, this is done for the rectangular unit cell shown in FIG. 6C, but can be readily expanded to other unit cells as well. One way to view the results of the PWEM is through the use of isofrequency contours as shown in FIG. 7. These contours are plotted for the unit cell size, a, divided by the free space wavelength, $\lambda_0$, for various wave vectors ($k_x$, $k_z$) scaled by the unit cell size, a.

Figure 8:
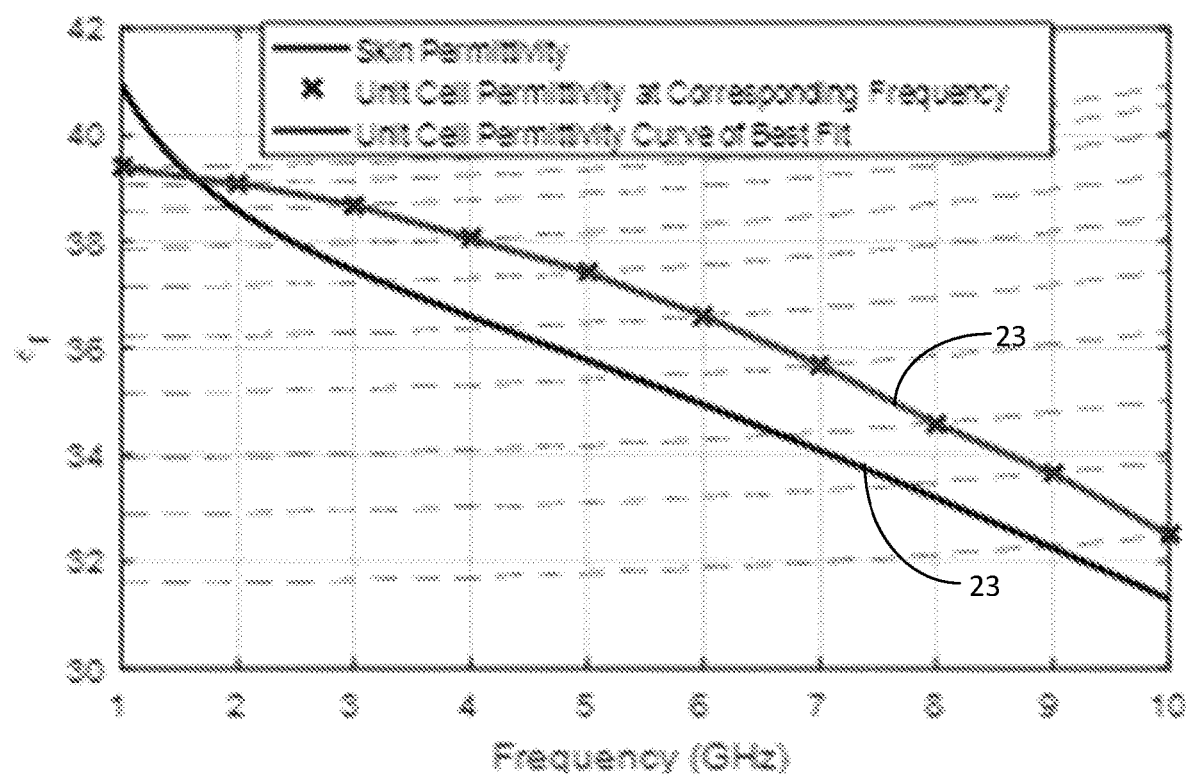
FIG. 8 is an effective permittivities v. frequency extrapolated from the isofrequency contour plot shown in FIG. 7.

As a next step, the effective permittivity of the medium can be extrapolated from the isofrequency contour plot, as shown by FIG. 8, which is an effective permittivities v. frequency plot. Each of the dashed lines in FIG. 8 corresponds to the solved PWEM permittivity values in the X-direction at a given frequency. Notably, the PWEM is limited, because it only takes into account one frequency's electrical properties. Since water is highly dispersive, it needs to be implemented multiple times to account for the changing electrical properties with frequency. As such, each of these frequency-dependent curves will only remain valid at one point marked with an "x." In turn, the effective permittivity needs to be solved at multiple points to develop a smooth curve over a wide bandwidth, as represented by curve 23. Curve 24 represents skin effective permittivity as a function of frequency. For this example case, the maximum percentage difference between the skin and unit cell permittivities is smaller than 4.76% across the entire 1 to 10 GHz bandwidth plotted in FIG. 8.

III. Modeling of the BMA Performance

This Section discusses how to modify BMA design aspects to customize antenna performance. Section III.A discusses how unit cell size relates to the high frequency cutoff, whereas Section III.B describes how the low frequency cutoff relates to antenna size. The real input impedance is described as relating to the flare angles and water concentration in Section III.C, and the optimal transmission for a BMA is studied for various sizes in Section III.D. All relations are hereafter studied through simulating BMAs that employ the rectangular unit cell of FIG. 6C. This unit cell is chosen as attributed to: (a) the reduced simulation time, and (b) the fact that this unit cell can be easily manipulated with flare angle. In contrast, the hexagonal and cylindrical unit cells can only be implemented with a 45° flare angle, or else the edge of the BMA will cut through the water holes. To demonstrate how the developed framework can be generalized to other unit cells besides rectangular, a discussion is included in Section III.E.

While a wide variety of tissue models may be considered in simulations depending on anatomical region, analysis in Section IV considers a homogeneous skin tissue model. This is because we intend to set a simple standard in place that can show the general trends for various applications. Skin tissue is chosen as it is the first layer of electromagnetic propagation and exhibits electrical properties close to those of ⅔ muscle (as often used to emulate the average human body properties).

A. High Frequency Cutoff

As seen in FIG. 8B, the permittivity increases dramatically when the unit cell becomes electrically large (i.e., at high frequencies). This causes the unit cell to no longer behave like an effective medium, thus limiting the bandwidth of the BMA by restricting its upper frequency limit. To analytically derive the high frequency cutoff, parametric studies of the BMA are conducted in simulation.

For the rectangular unit cell of FIG. 6C, a typical effective medium band extends from DC to wavelengths that are 0.05a, where "a" is the unit cell size. To study the exact cutoff, the rectangular unit cell BMA was simulated against skin and the high frequency cutoff was determined to be where the reflection coefficient is greater than −10 dB. Under these conditions, the free space cutoff wavelength ($\lambda_0$) can be modeled as being linearly related to the unit cell size (a) with an offset based upon the water fill ratio (r), as shown in Eq. 1(a). The slope, K, between the cutoff wavelength and unit cell size depends on the factors that can vary impedance, θ and r, as shown in Eq. 1(b).

$$\lambda_0 = aK - 0.006r \quad (1a)$$

$$K = 21.811 - 15.172 \ln(\cos\theta) + 8.317 \ln(r) - 5.785 \frac{\ln(r)}{\ln(\cos\theta)} \quad (1b)$$

Figure 9A:
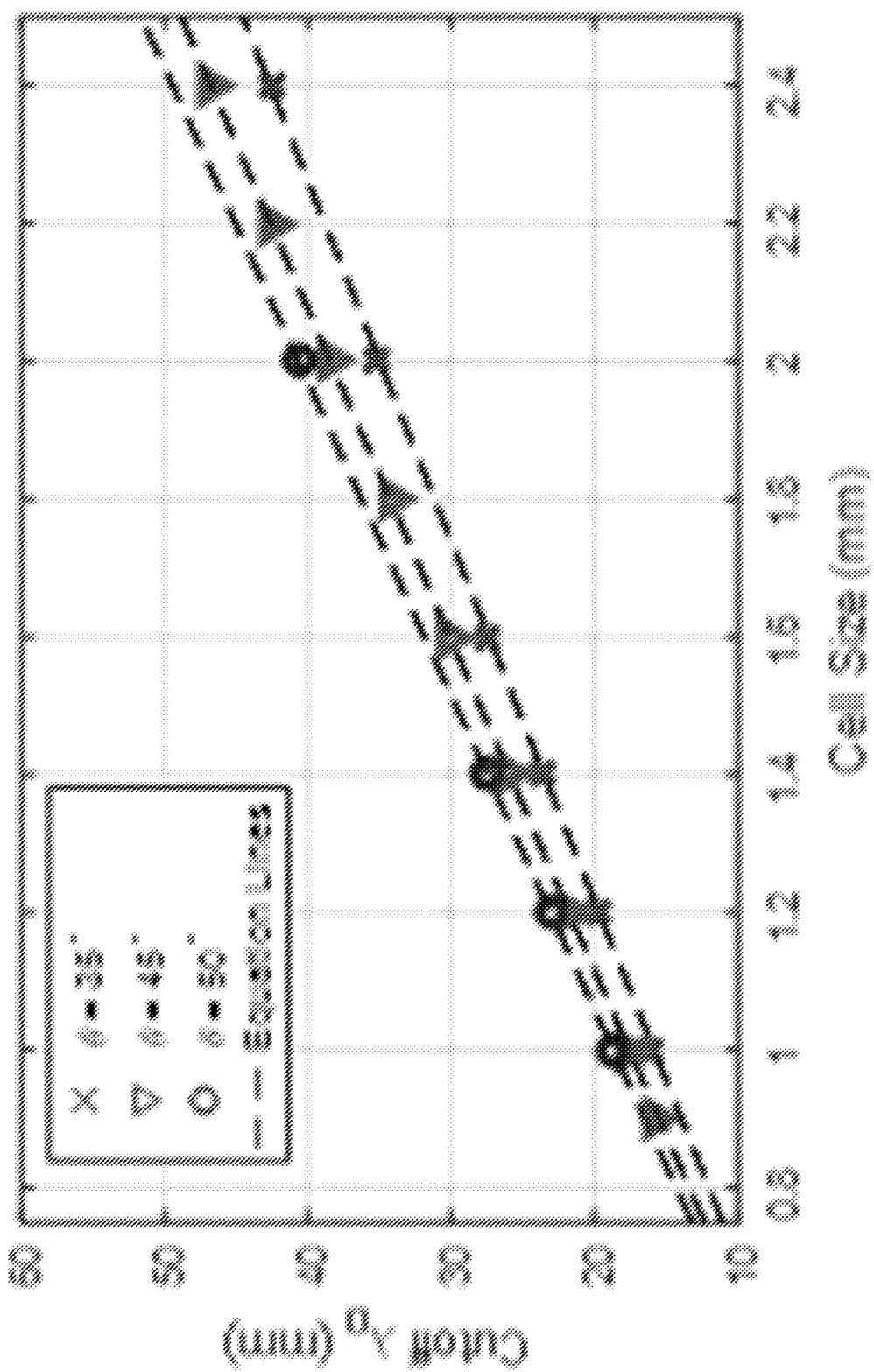
FIGS. 9A and 9B are plots of the free space high frequency cutoff wavelength ($\lambda_0$) against the cell size, a, for varying flare angle and varying fill fraction, respectively.
Figure 9B:
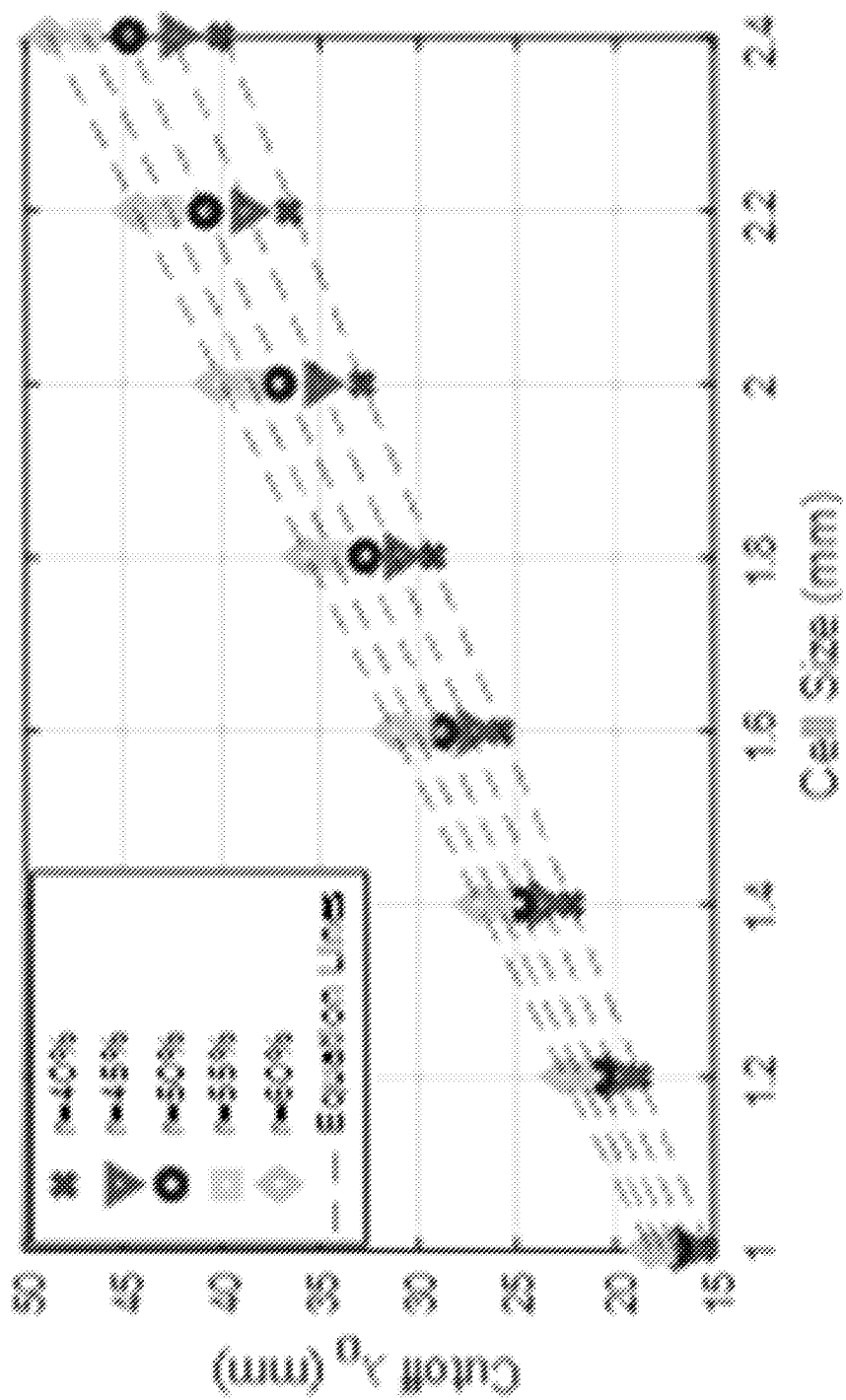

Verification of these equations is shown in FIGS. 9A and 9B, which are plots of the free space cutoff wavelength ($\lambda_0$) against the cell size, a, for varying flare angle (FIG. 9A) and varying fill fraction (FIG. 9B). The predicting Eq. (1) is super-imposed in dashed lines, showing excellent agreement (error smaller than 1.75% in all cases). The slope, K, is around ~20 for these plots, which coincides with the above results from the PWEM. The inverse of this K value is 0.05, which is a typical first band limit for a rectangular unit cell. Indeed, FIG. 8 shows that around 0.05a, the shape of the band begins to no longer be truly elliptical in the Z-direction, thus indicating that the effective medium limit is being reached.

B. Low Frequency Cutoff

The BMA can be modeled as a quasi-conical antenna with a loaded dielectric that focuses radiation. Similar to a conical antenna, the first resonance in the BMA occurs when its edge length (L in FIG. 2A) is equal to an electrical half-wavelength. This is modeled by Eq. 2 below, which relates the resonant free-space wavelength ($\lambda_{r0}$) to the BMA edge length (L) and the effective permittivity $\varepsilon_{eff}$.

$$\frac{\lambda_{r0}}{2} = L\sqrt{\varepsilon_{eff}} \quad (2)$$

Figure 10:
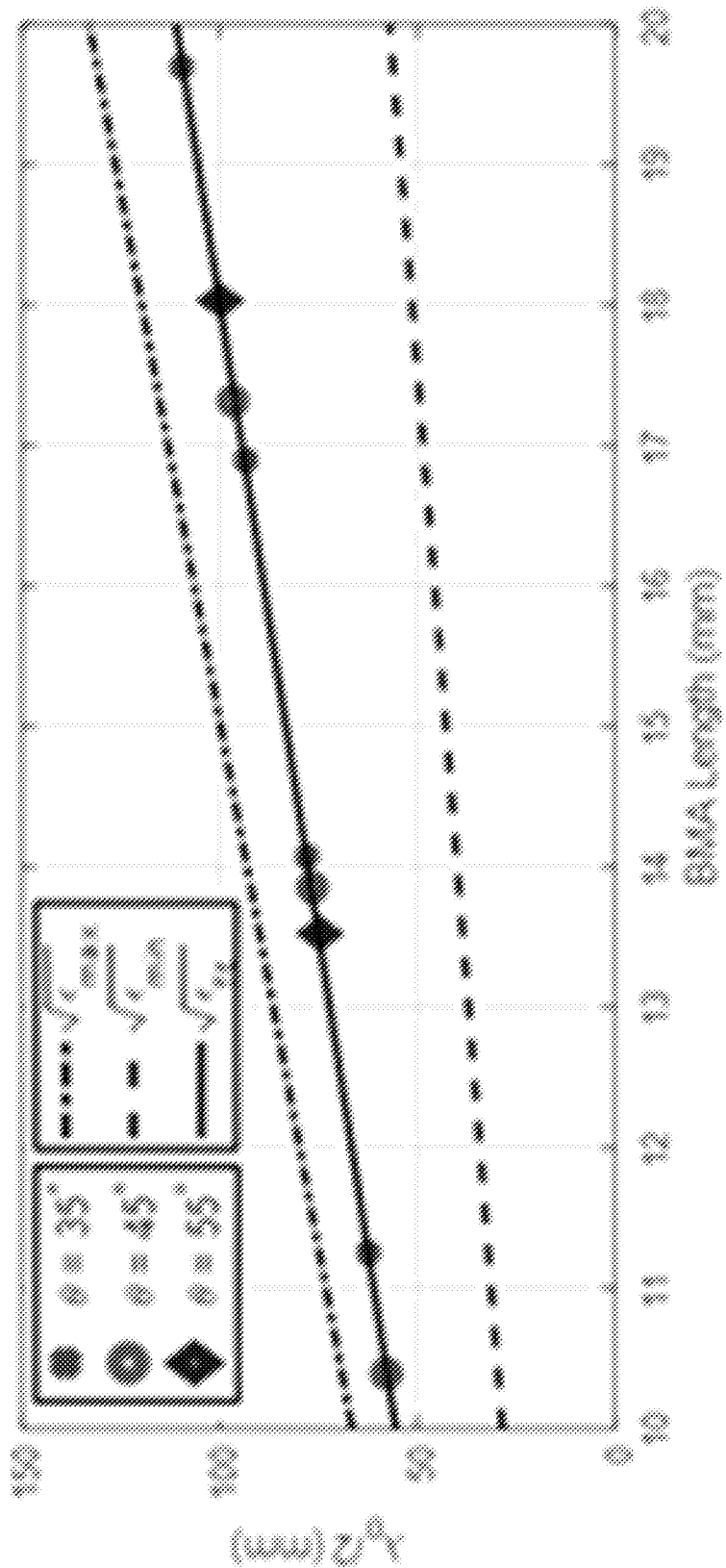
FIG. 10 is a plot of the low frequency resonant half-wavelengths vs. BMA edge lengths, as well as the maximum $\sqrt{\varepsilon_r}$ and minimum $\sqrt{\varepsilon_r}$ calculated from the Plane Wave Expansion Method (PWEM) for numerous BMAs with rectangular unit cells (r=55%) of varying height and angle simulated against skin.

The flux developed, which depends on $\varepsilon_{eff}$, is not solely influenced by the maximum permittivity direction discussed above with reference to FIGS. 5A and 5B. Instead, since the electric fields are normal to the flares, there will be a component of the flux developed that is in the lower permittivity direction. Numerous BMAs with rectangular unit cells (r=55%) of varying height and angle were simulated against skin. The resonant half-wavelengths are plotted against BMA edge lengths in FIG. 10, as well as the maximum $\sqrt{\varepsilon_r}$ and minimum $\sqrt{\varepsilon_r}$ calculated from the PWEM. As shown, the curve of best fit for the permittivity lies between the maximum and minimum permittivity lines. The ratio of the fit in this instance is 83.5% maximum permittivity and 17.5% minimum permittivity. This ratio of the fit will change based upon the water's dispersion over the bandwidth. Moreover, the dispersion of water would also manifest as nonlinear permittivity slopes between the resonant half-wavelengths and the edge lengths if plotted over a significantly large bandwidth.

C. BMA Input Impedance

Figure 11:
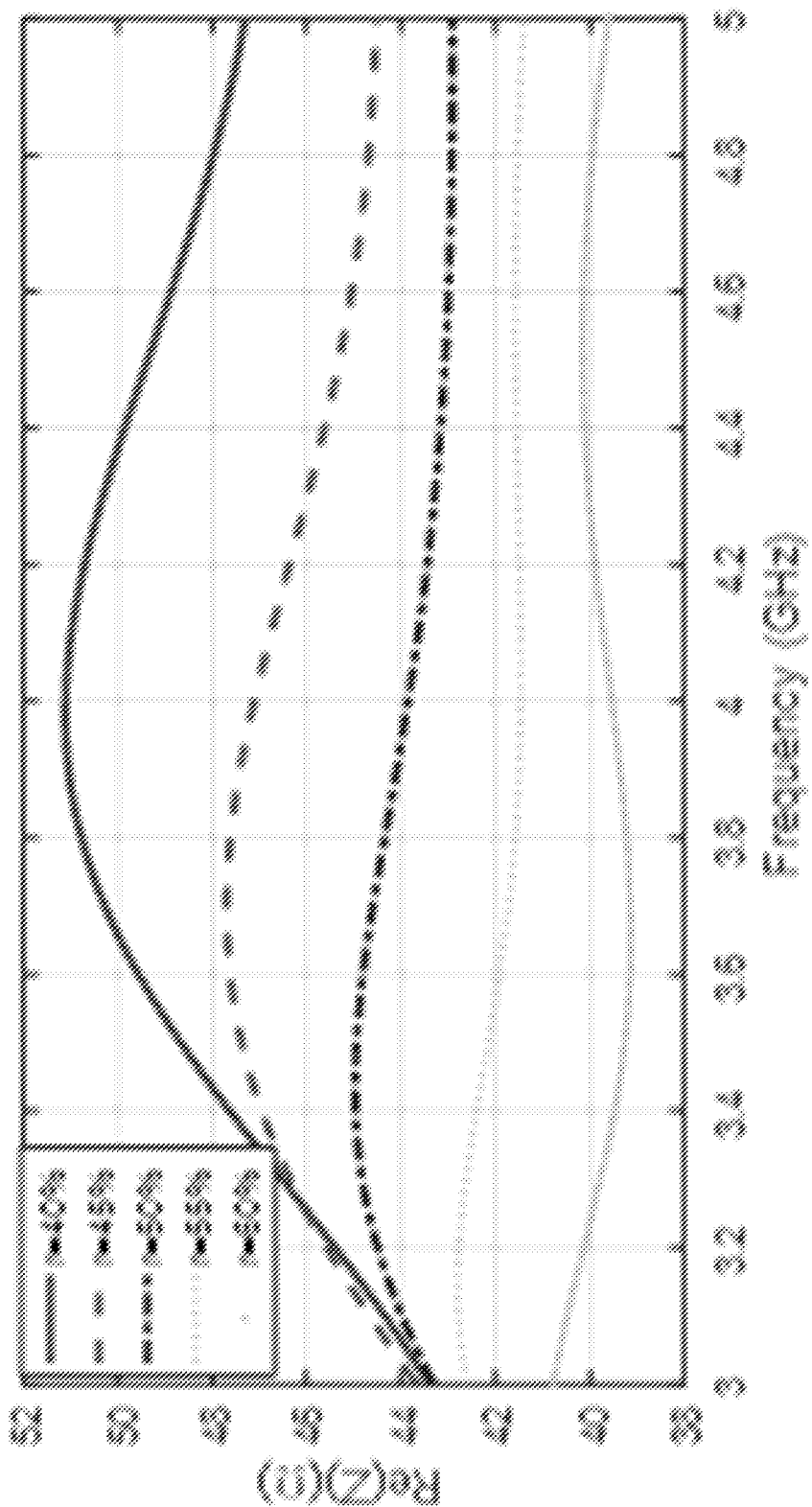
FIG. 11 is a plot of the BMA's real input impedance as a function of its water content indicating that increasing the water content (r) of the BMA should decrease its real impedance.

The BMA's real input impedance can be explored as a function of its: (a) water content and (b) flare angle. To test this, a rectangular unit cell BMA of height 10 mm and flare angle 45° was simulated against a homogeneous skin block. Since the water has a high permittivity, it also has a low impedance. Therefore, increasing the water content (r) of the BMA is anticipated to decrease its real impedance, as shown in FIG. 11.

Figure 12A:
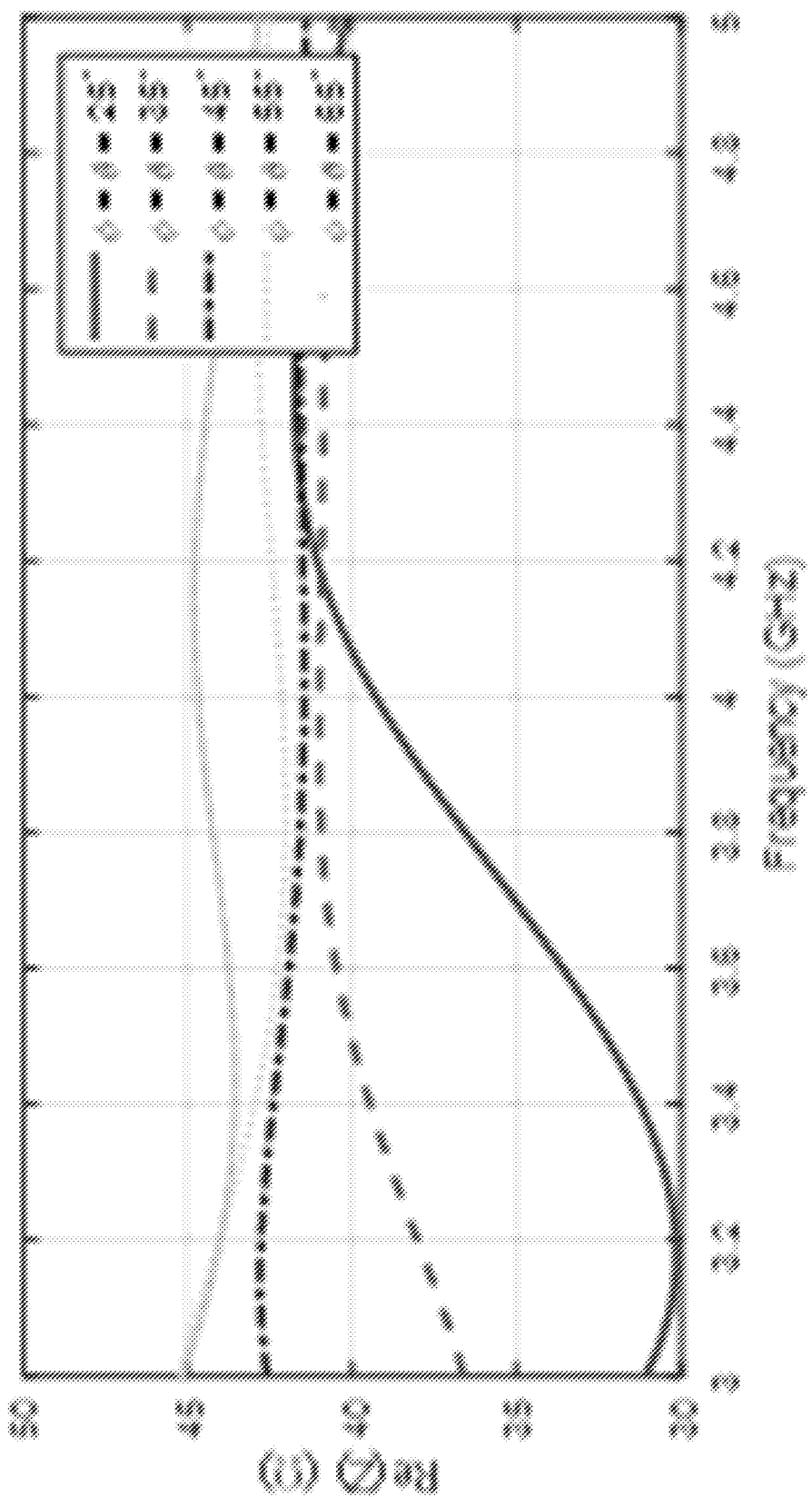
FIGS. 12A and 12B are plots of the BMA's real input impedance as a function of flare angle.
Figure 12B:
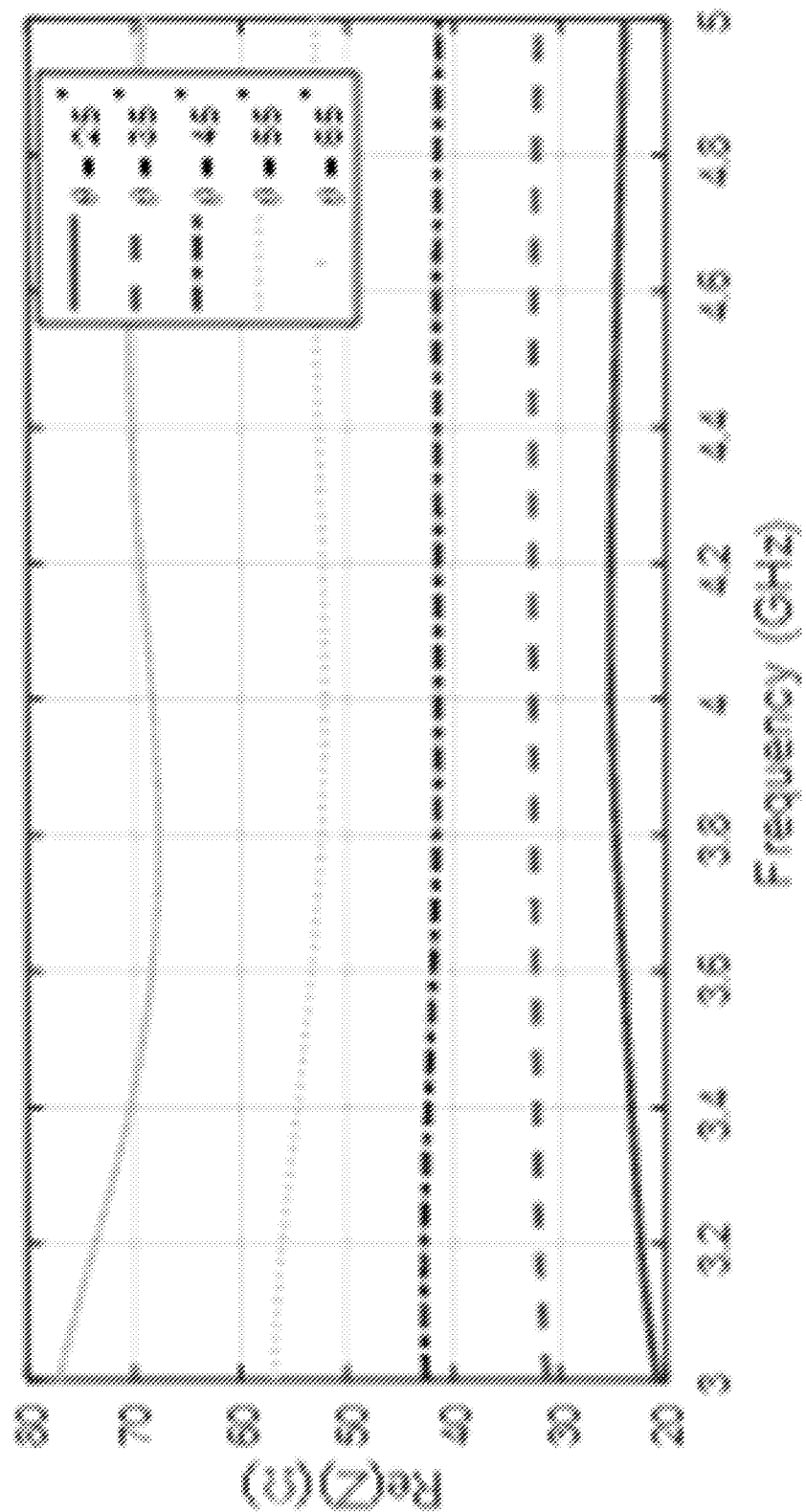

Moreover, the flare angle of the BMA can be modified in order to further control its impedance. Similar to a conical antenna, narrower flare angles are expected to lower the input impedance and wider flare angles are expected to raise the input impedance, as shown in FIG. 12A. If the θ angle (normal to the flare) is different from the φ angle (parallel to the flares), this effect will be more pronounced, as shown in FIG. 12B. In this case, φ=45° and θ varies.

D. Transmission Loss

Figure 13A:
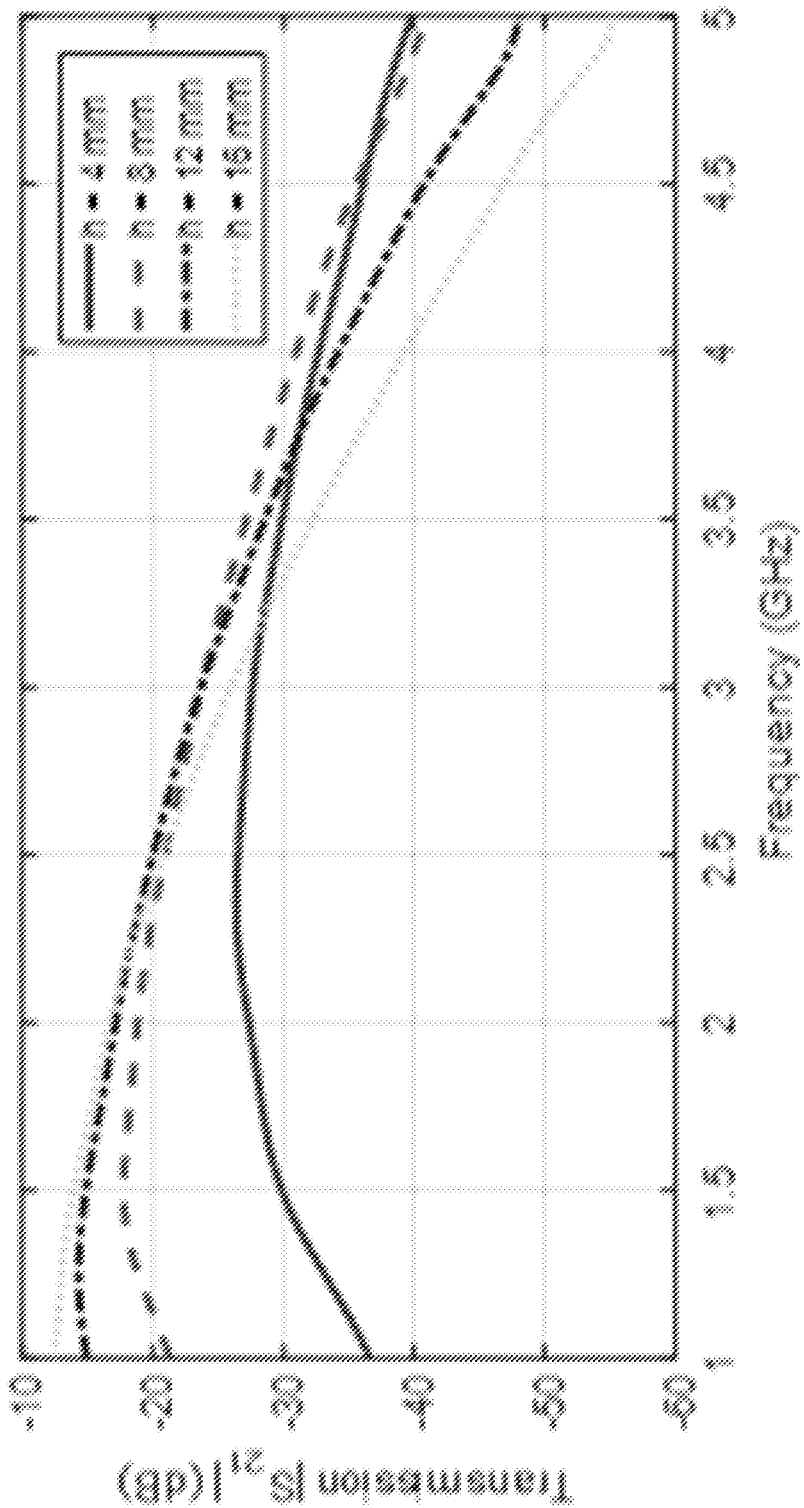
FIGS. 13A and 13B are transmission loss v. frequency plots for varying height and varying flare angle of the BMA, respectively.
Figure 13B:
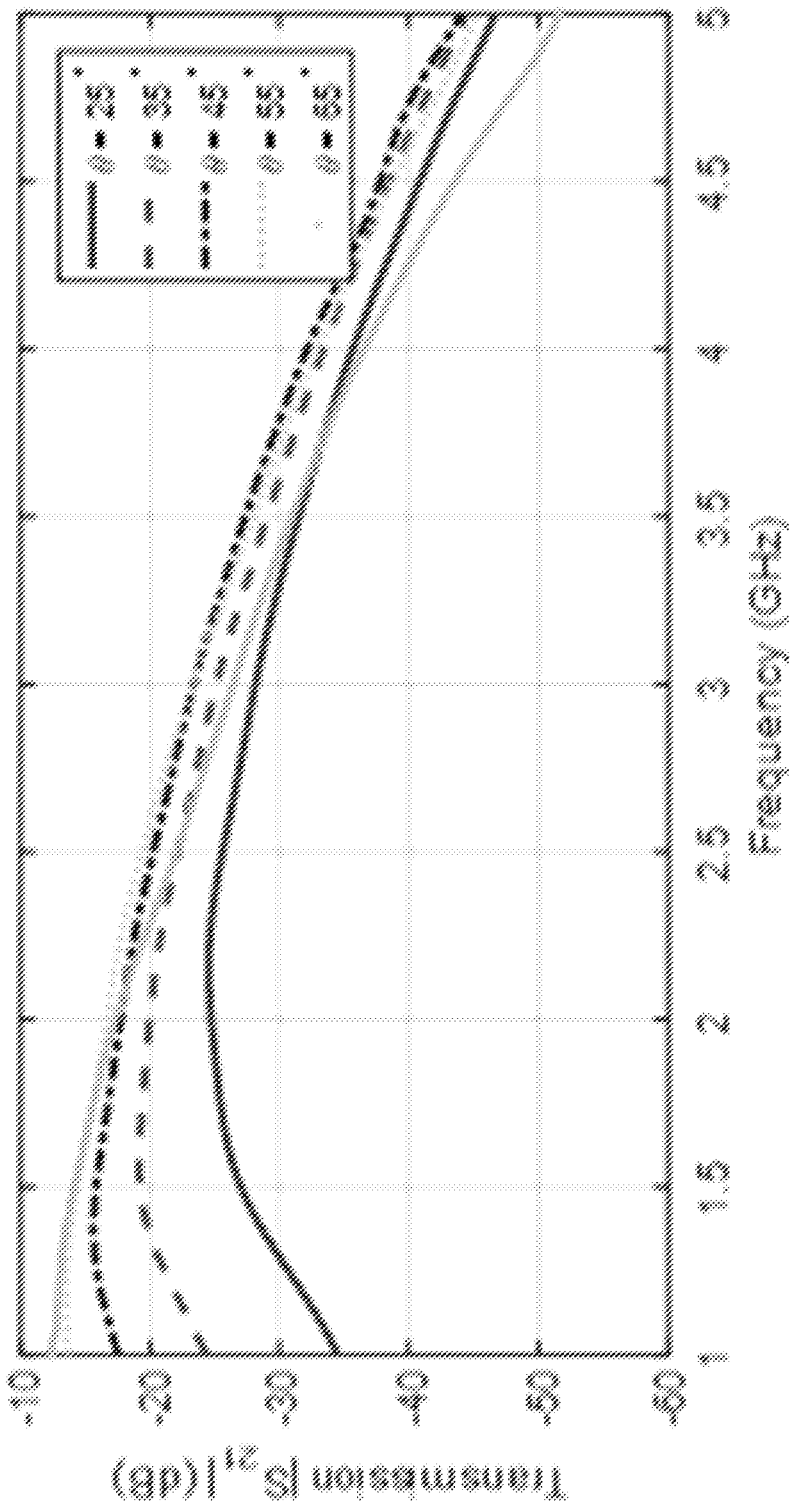

The BMA gain is dependent primarily on its size, quantified by the flare contact angle, θ, and height, h. The general trend is that a BMA's transmission loss is smallest towards its lower operating frequency. This is expected, because larger BMAs have higher material loss. Also, larger BMAs develop a wider beam, which will have increased loss with frequency as well. To demonstrate these effects, two rectangular unit cell BMAs (h=10 mm, r=0.55) were simulated on both sides of a 30 mm block that had the electrical properties of skin. FIGS. 13A and 13B are transmission loss vs. frequency plots for varying height and varying flare angle of the BMA, respectively. The transmission vs. frequency plots indicate that larger BMAs have sharper transmission degradation with respect to frequency than smaller ones, as shown in FIGS. 13A and 13B. This indicates that a BMA should be designed for minimum necessary size, so that it has minimal transmission loss across its bandwidth.

E. Applicability to Other Unit Cells

Simulations and theoretical modeling for hexagonal and cylindrical cells indicate that Eq. 1(a) above is robust and accounts for a wide variety of designs. Expectedly, the slope, K, will vary depending on the type of unit cell included. Different unit cells have different effective medium limits and would therefore have different slopes.

Section III.B depended primarily upon the permittivity developed by the unit cell. As such, using the PWEM to analyze the permittivity will allow for direct use of Eq. 2. Further, the real input impedance can still be manipulated, as mentioned in Section III.C, regardless of the type of unit cell.

Figure 14:
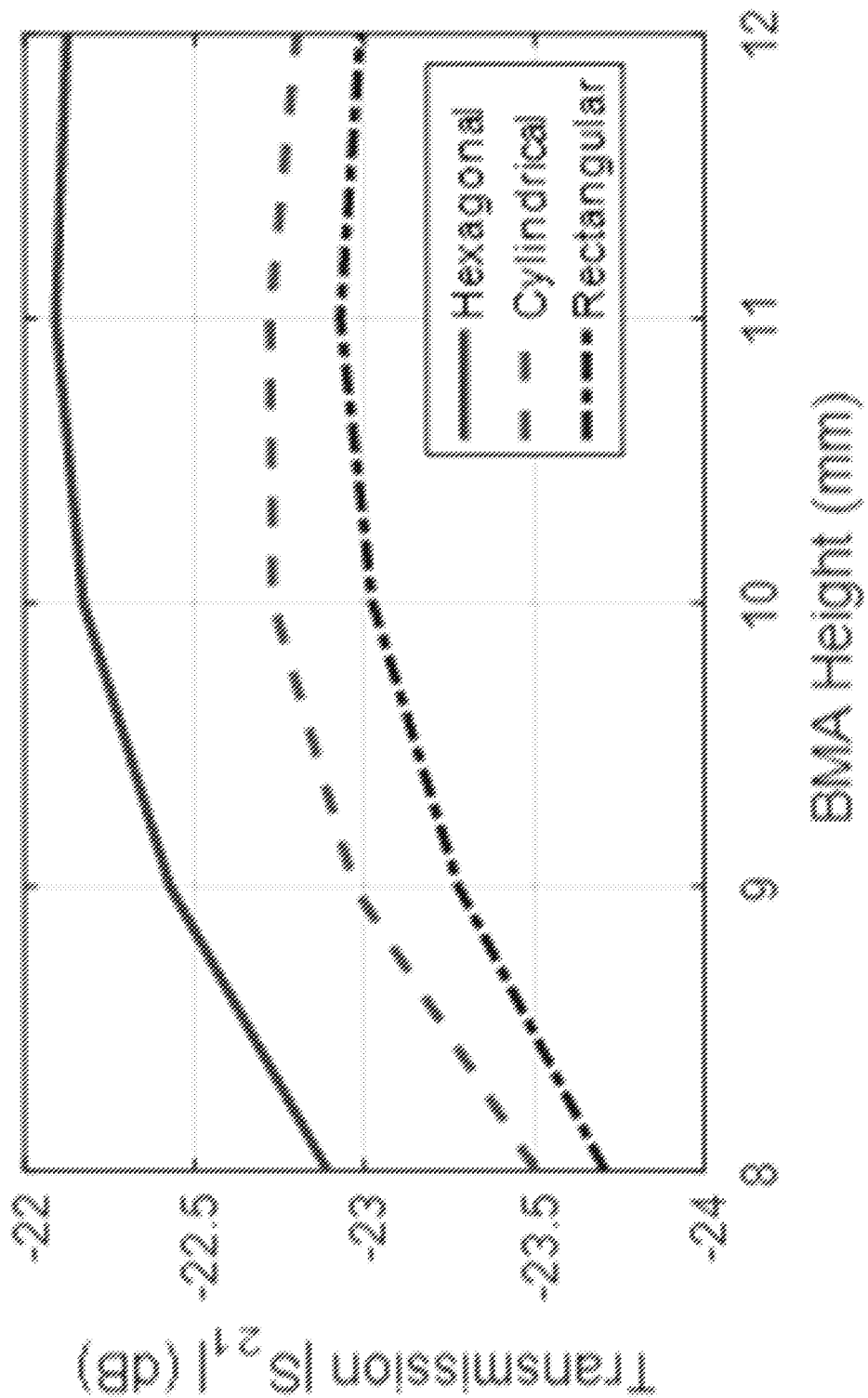
FIG. 14 is a plot of transmission loss results as a function of BMA height, h, for transmission at an example frequency of 3 GHz through an example thickness of tissue of 3 cm for varying unit cells and BMA heights.

To discern the effect of unit cell type upon transmission loss, the setup described above with reference to FIGS. 13A and 13B was employed again and the BMA cells were altered between rectangular, hexagonal and cylindrical. In all three cases, the unit cell size and water ratio were maintained roughly the same. FIG. 14 is a plot of transmission loss results as a function of BMA height, H, for transmission at an example frequency of 3 GHz through an example thickness of tissue of 3 cm for varying unit cells and BMA heights. As seen in FIG. 14, hexagonal unit cells have the least amount of loss. This was expected since hexagonal unit cells are the most anisotropic per discussions in Section II.C.

Having described the theoretical framework for designing BMAs, a few representative embodiments of BMAs will be described. In accordance with a representative embodiment, the BMA is a quasi-conical antenna made at least partially of a non-electrically-conductive, i.e., dielectric, material having a first relative permittivity that ranges from about 1.0 to 10.0 and preferably from about 2.0 to 4.0. At least a first side of the pyramid-shaped engineered dielectric element has a plurality of holes formed in it. A material is disposed inside of the holes that has a second relative permittivity that ranges from about 50 to 90. Disposing the material inside of the holes provides the engineered dielectric element with an effective permittivity that is closely matched, over the predetermined range of frequencies, to a frequency-dependent permittivity of skin. An electrically-conductive material at least partially covers at least a first side of the pyramid element. In accordance with a representative embodiment in which the antenna element is pyramidal in shape, the electrically-conductive material covers at least first and second opposite sides of the pyramid element. The electrically-conductive material may be, for example, strips of copper tape.

IV. First Experimental Setup

In accordance with a representative, or exemplary, embodiment, a miniaturized (1.773 cm$^3$) wearable, or on-body, BMA is disclosed that employs an anisotropic material configuration to mimic the frequency-dependent electrical properties of biological tissues across its 1 to 9 GHz bandwidth. As highlighted in Tables III and IV below, the bio-matched antenna offers a promising alternative to existing on-body antenna designs for wireless telemetry with both subcutaneous (<5-mm-deep) and deep-tissue (>5-mm-deep) implants. The antenna is remarkably efficient, offering 14.5 dB lower transmission loss vs. previous designs at 2.4 GHz for a 4 millimeter (mm) implantation depth. Concurrently, the bio-matched antenna offers 10.8 dB lower transmission loss vs. previous designs at 2.4 GHz for a 2 cm implantation depth. That is, the antenna brings forward transformational opportunities for biomedical telemetry with wireless implants.

TABLE III

SUBCUTANEOUS COUPLING: COMPARISON OF PROPOSED DESIGN VS. THE STATE OF THE ART

| Ref. | Frequency | Implantation Depth | Air Gap | Size/Antenna Type | Bandwidth | Transmission Loss |
|---|---|---|---|---|---|---|
| [4] | 2.4 GHz | 3.3 mm | 4 mm | $\pi \times 72.5^2 \times 13.635$ mm$^3$/Spiral | 0.6-6 GHz | 26 dB |
|  | 4.8 GHz | 3.3 mm | 4 mm | $\pi \times 72.5^2 \times 13.635$ mm$^3$/Spiral | 0.6-6 GHz | 19 dB |
| [5] | 400 MHz | 4 mm | 5 cm | 375 mm/Dipole | NA | 34 dB |
|  | 2.4 GHz | 4 mm | 5 cm | 62.4 mm/Dipole | NA | 32 dB |
| [6] | 2.4 GHz | 4 mm | 0 cm | 26.3 × 30 × 1.6 mm$^3$/Spiral | 2-11 GHz | 22.5 dB |
| This work | 2.4 GHz | 4 mm | 0 cm | 22 × 22 × 10 mm$^3$/BMA | 1.4-8.5 GHz | 8.01 dB |

TABLE IV

DEEP TISSUE COUPLING: COMPARISON OF PROPOSED DESIGN VS. THE STATE OF THE ART

| Ref. | Frequency | Implantation Depth | Air Gap | Size/Antenna Type | Bandwidth | Transmission Loss |
|---|---|---|---|---|---|---|
| [7] | 400 MHz | 9 mm | 0 cm | 28 × 26.8 × 0.635 mm$^3$/Patch | 380-470 MHz | 24 dB |
| [8] | 2.4 GHz | 2 cm | 0 cm | $\pi \times 17.5^2 \times 0.76$ mm$^3$/Exponentially Tapered Slot | 2.35-2.7 GHz | 30 dB |

TABLE IV-continued

DEEP TISSUE COUPLING: COMPARISON OF
PROPOSED DESIGN VS. THE STATE OF THE ART

| Ref. | Frequency | Implantation Depth | Air Gap | Size/Antenna Type | Bandwidth | Transmission Loss |
|---|---|---|---|---|---|---|
| [9] | 2.4 GHz | 3.5 cm | 10 cm | NA/Free-Space Horn | 0.9-2.45 GHz | 56.5 dB |
| [10] | 400 MHz | 1 cm | 1.5 cm | 70 × 60 × 1.6 mm³/Patch | 350-450 MHz | 50 dB |
| [11] | 2.4 GHz | 5 cm | 2.55 m | NA/Free-Space Horn | NA | 81 dB |
| This work | 2.4 GHz | 2 cm | 0 cm | 22 × 22 × 10 mm³/BMA | 1.4-8.5 GHz | 19.2 dB |

Figure 15:
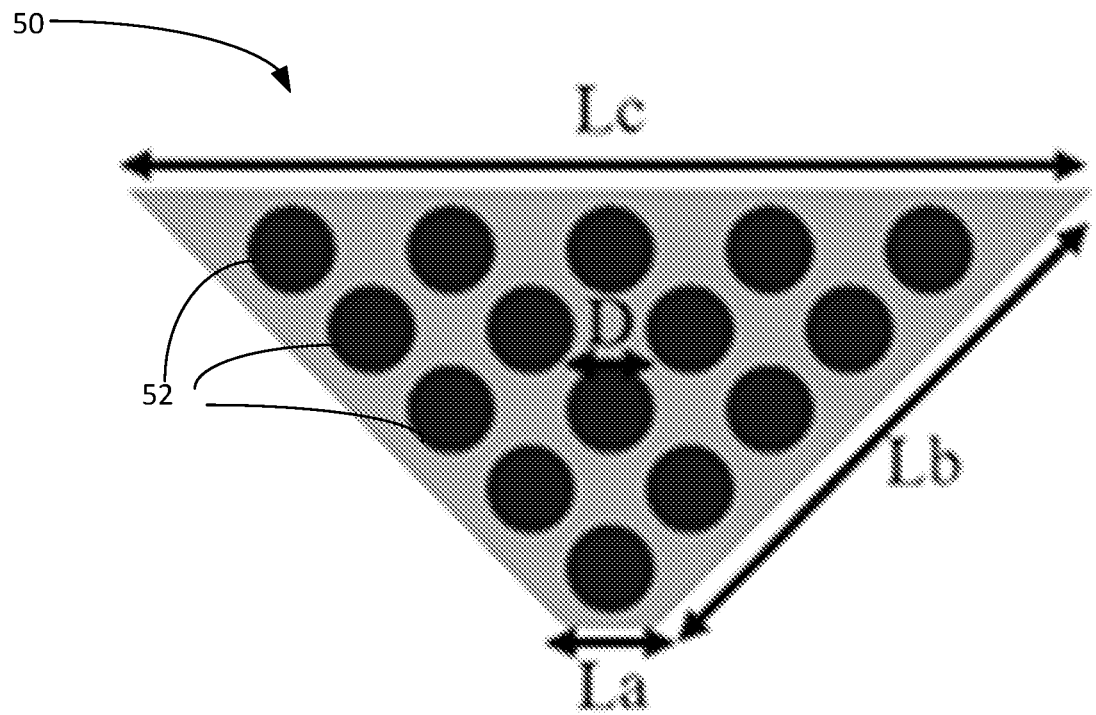
FIG. 15 illustrates a side plan view diagram of a BMA in accordance with a representative embodiment.
Figure 16:
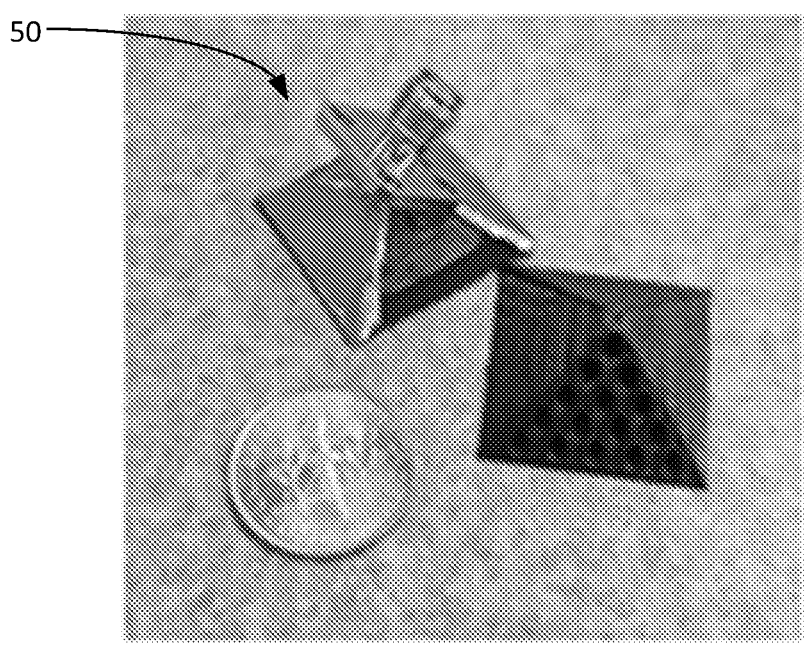
FIG. 16 is a photograph taken of the BMA shown in FIG. 15 having a coaxial connector mounted thereon.
Figure 17:
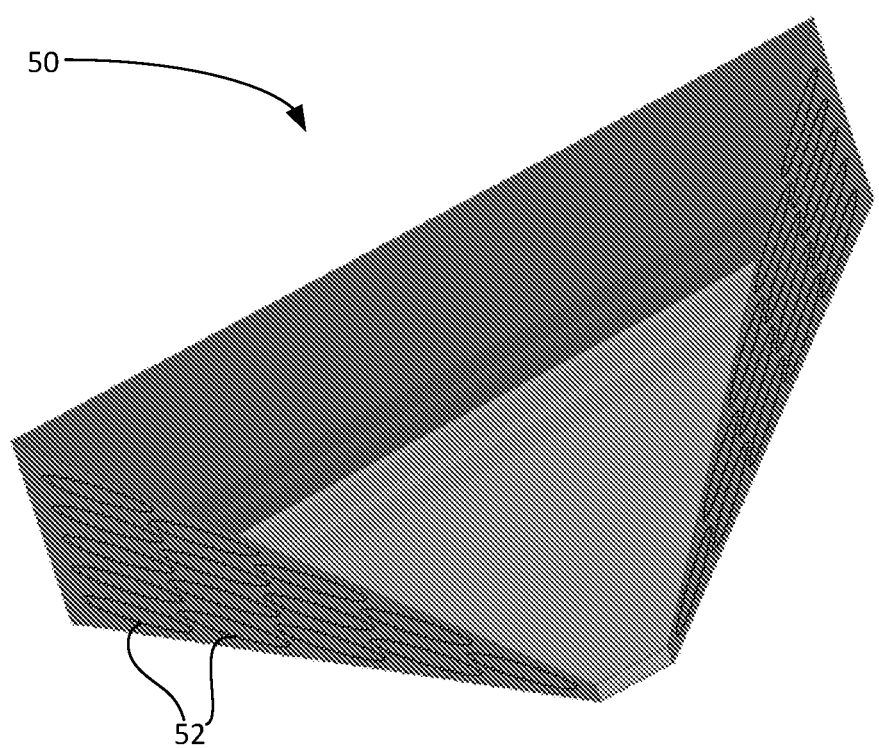
FIG. 17 illustrates a perspective view of the BMA shown in FIGS. 15 and 16 in accordance with a representative embodiment.

A side plan view diagram of the BMA 50 in accordance with a representative embodiment is shown in FIG. 15 with design parameters given below in Table V. In accordance with this representative embodiment, the BMA 50 is a conical bio-matched antenna. FIG. 16 is a photograph taken of the BMA 50 having an SMA connector mounted thereon positioned beside a dime to provide an idea of the scale of the BMA 50 in accordance with this embodiment. FIG. 17 is a perspective view of the BMA 50 shown in FIGS. 15 and 16 in accordance with a representative embodiment.

In accordance with this embodiment, the BMA 50 is compact, maintaining a volume of 1.773 cm³, and is intended for on-body operation and telemetry with subcutaneous and/or deep-tissue wireless implants (not shown). In accordance with this embodiment, the BMA 50 has an effective permittivity that has been engineered to match the frequency-dependent permittivity of the underlying skin tissue across the entire 1 to 9 GHz bandwidth, although it should be noted that the inventive principles and concepts are not limited to any particular range of frequencies. In accordance with this embodiment, this is accomplished by including 2-mm-diameter cylindrical through holes 52 that extend from a first side to a second side of a 3D-printed polylactic acid ($\varepsilon_r=3.549$, tan $\delta=0.001$) pyramid structure. In accordance with this representative embodiment, the through holes 52 are subsequently filled with distilled water. The holes 52 are subsequently capped to prevent the distilled water from flowing, or spilling, out of the holes 52.

TABLE V

DIMENSIONS OF THE BIO-MATCHED ANTENNA

| Parameter | Value | Parameter | Value |
|---|---|---|---|
| La | 2 mm | Lc | 22 mm |
| Lb | 17.3 mm | D | 2 mm |

Figure 18:
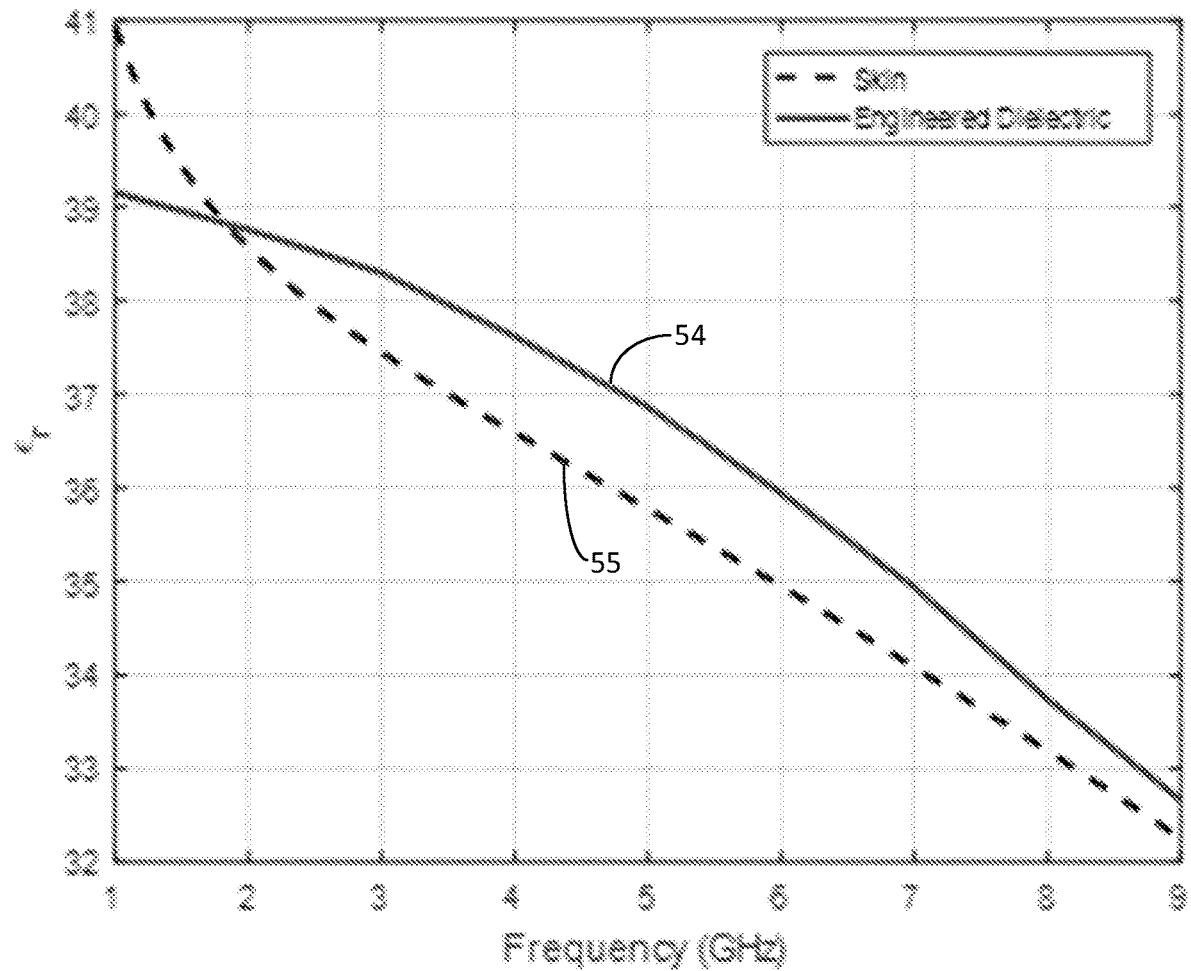
FIG. 18 is a plot showing the effective relative permittivity of the dielectric material used to make the BMA shown in FIG. 15 compared to the permittivity of skin over a broad bandwidth.

The engineered dielectric material was designed to be anisotropic, developing a higher permittivity parallel to the cylinders and a lower permittivity orthogonal to the cylinders. FIG. 18 is a plot showing the effective relative permittivity of the dielectric material used to make the BMA 50 compared to the permittivity of skin over a broad bandwidth of 1 to 9 GHz. Curve 54 corresponds to the effective permittivity of the engineered dielectric as a function of frequency and curve 55 corresponds to the permittivity of skin as a function of frequency. As seen in FIG. 18, the difference between the two permittivities is less than 2.86% across the entire 1 to 9 GHz bandwidth.

In accordance with an embodiment, the BMA 50 is a device that is 3-D printed using a Raise3D N2 printer and polylactic acid filaments ($\varepsilon_r=3.549$, tan $\delta=0.001$ [25]). It should be noted, however, that the BMAs disclosed herein are not limited with respect to the manner in which they are made. Once the plastic container was printed, the holes 52 of the BMA 50 were filled with distilled water. Super glue was then applied along the edges of the pyramid, and copper tape was placed on top of the adhesive to seal in the water. In this particular case, copper tape serves as the conducting flares of the BMA. The prototype of the fabricated BMA 50 is shown in FIG. 16.

Figure 19:
FIG. 19 depicts a SPEAG's POPEYE leg phantom that was used as a tissue-emulating phantom to evaluate the performance of the BMA shown in FIG. 15.
Figure 20:
FIG. 20 depicts an 80% lean ground beef phantom that was used as a tissue-emulating phantom to evaluate the performance of the BMA shown in FIG. 15.
Figure 21:
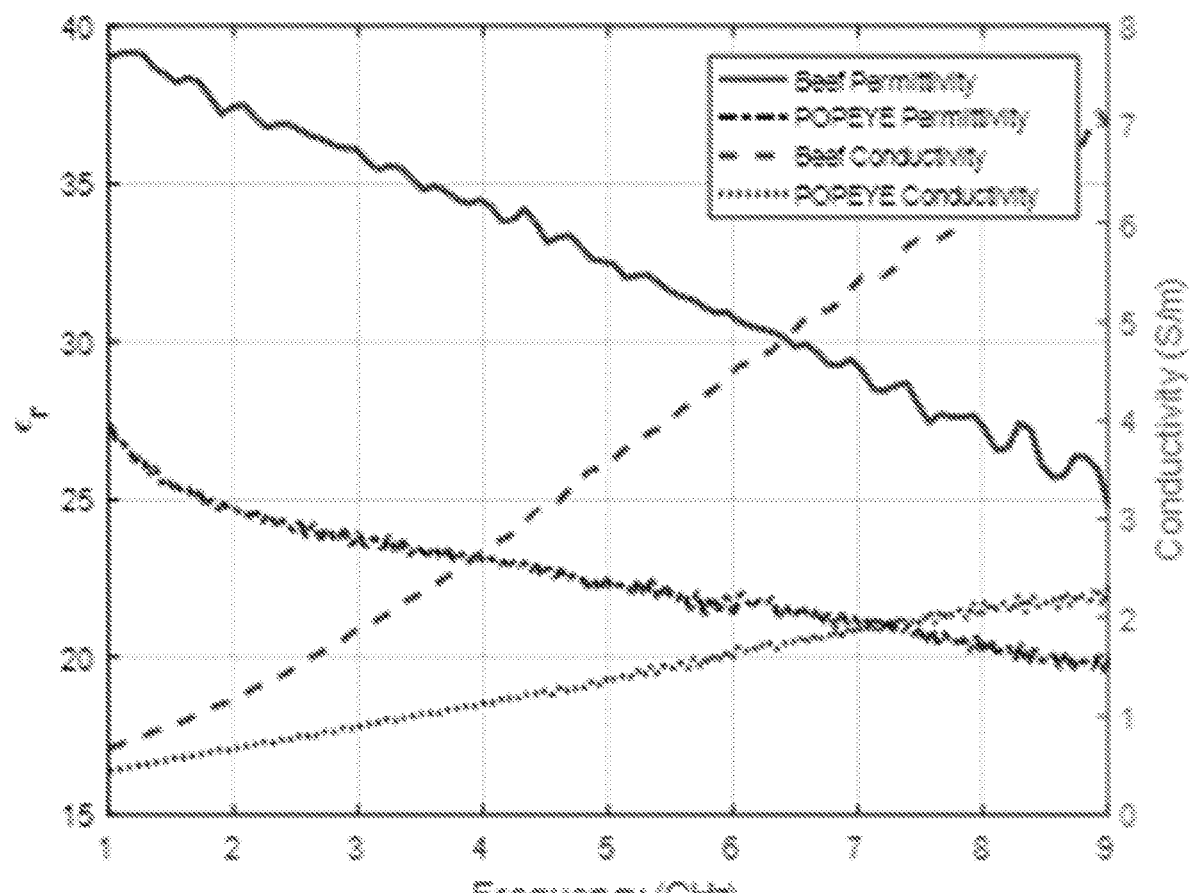
FIG. 21 is a plot of permittivity and conductivity for the phantoms shown in FIGS. 19 and 20 measured via Keysight's 85070E high-temperature probe over a 1 to 9 GHz frequency range.

Performance of the BMA 50 was experimentally evaluated upon tissue-emulating phantoms, and specifically upon: a) SPEAG's POPEYE leg phantom, as shown in FIG. 19, and an 80% lean ground beef phantom, as shown in FIG. 20. The POPEYE leg phantom enables accurate representation of the tissue anatomy and average electrical properties, but it is sealed and does not allow implantation of wireless implants for biomedical telemetry evaluation. To achieve the latter, the ground beef phantom shown in FIG. 20 was employed. As is well known in the art, ground beef phantoms have long been used to emulate the frequency-dependent electrical properties of biological tissues. FIG. 21 is a plot of permittivity and conductivity of both phantoms measured via Keysight's 85070E high-temperature probe at 1 to 9 GHz. Expectedly, the ground beef phantom exhibits higher permittivity and conductivity values, since it does not include bone tissue, which is inherently low-permittivity and low-loss. For comparison, the permittivity of ⅔ muscle tissue that is often used to emulate the average tissue properties varies from 36 to 28 in this frequency range. Accordingly, the conductivity of ⅔ muscle tissue varies from 0.65 to 7 S/m.

Figure 22:
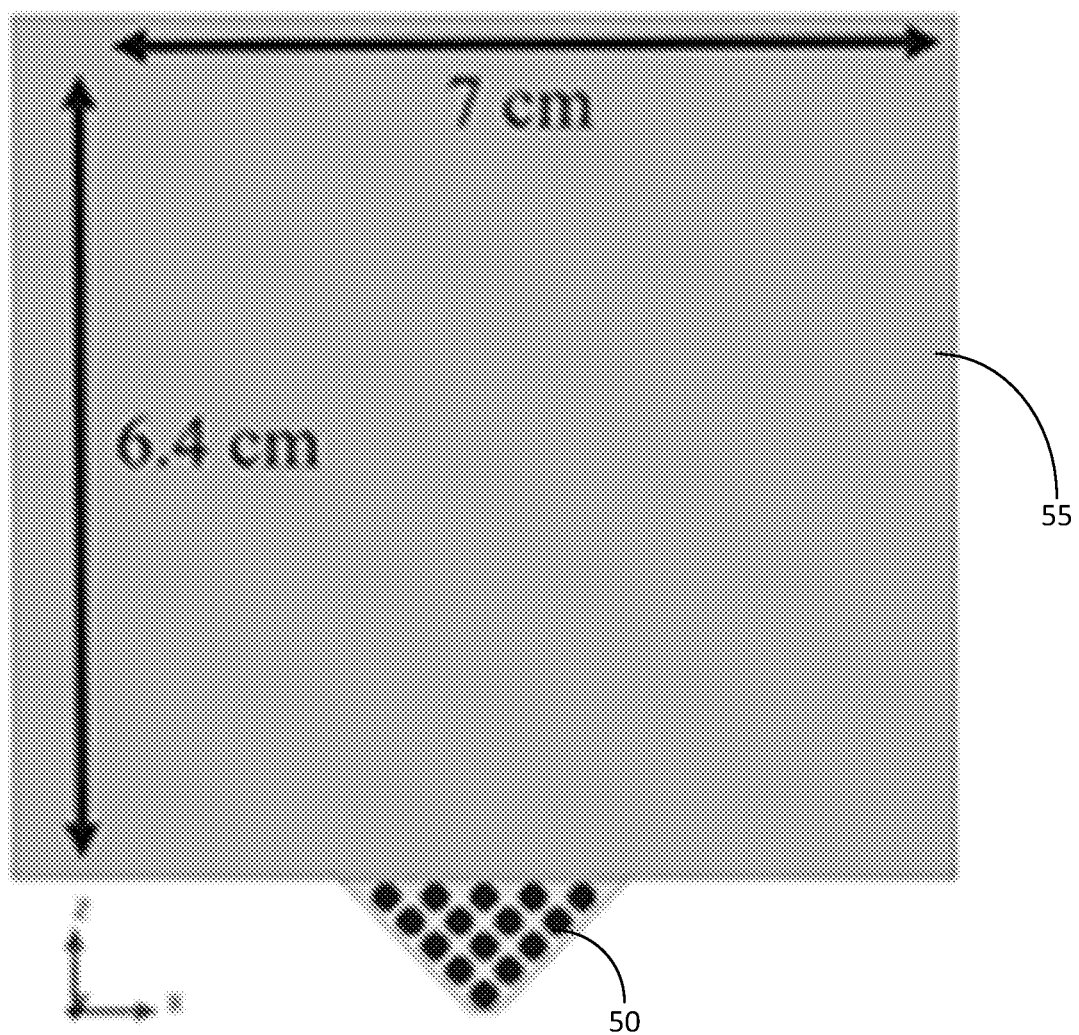
FIG. 22 shows the BMA shown in FIG. 15 placed against a 7 cm×7 cm×6.4 cm rectangular tissue-emulating box for performing Finite Element (FE) simulations for the BMA.

Finite Element (FE) simulations for the BMA 50 were performed in Ansys High Frequency Structure Simulator (HFSS). As depicted in the diagram of FIG. 22, the BMA 50 was placed against a 7 cm×7 cm×6.4 cm rectangular tissue-emulating box 55. Permittivity and conductivity of the aforementioned box 55 represented the measured electrical properties of the POPEYE and/or the ground beef phantom, per the study requirements.

Simulation and measurement results are hereafter presented for the BMA 50: a) reflection coefficient, b) electric fields, c) transmission loss with subcutaneous and deep-tissue implants, d) sensitivity to misalignment, and e) SAR performance. Focus is on the 2.4 GHz ISM band, which has been repeatedly reported in the literature for biomedical telemetry with wireless implants. Of course, similar results can readily be derived at any of the operating frequencies of the bio-matched antenna 1 across its 1-9 GHz bandwidth.

Figure 23:
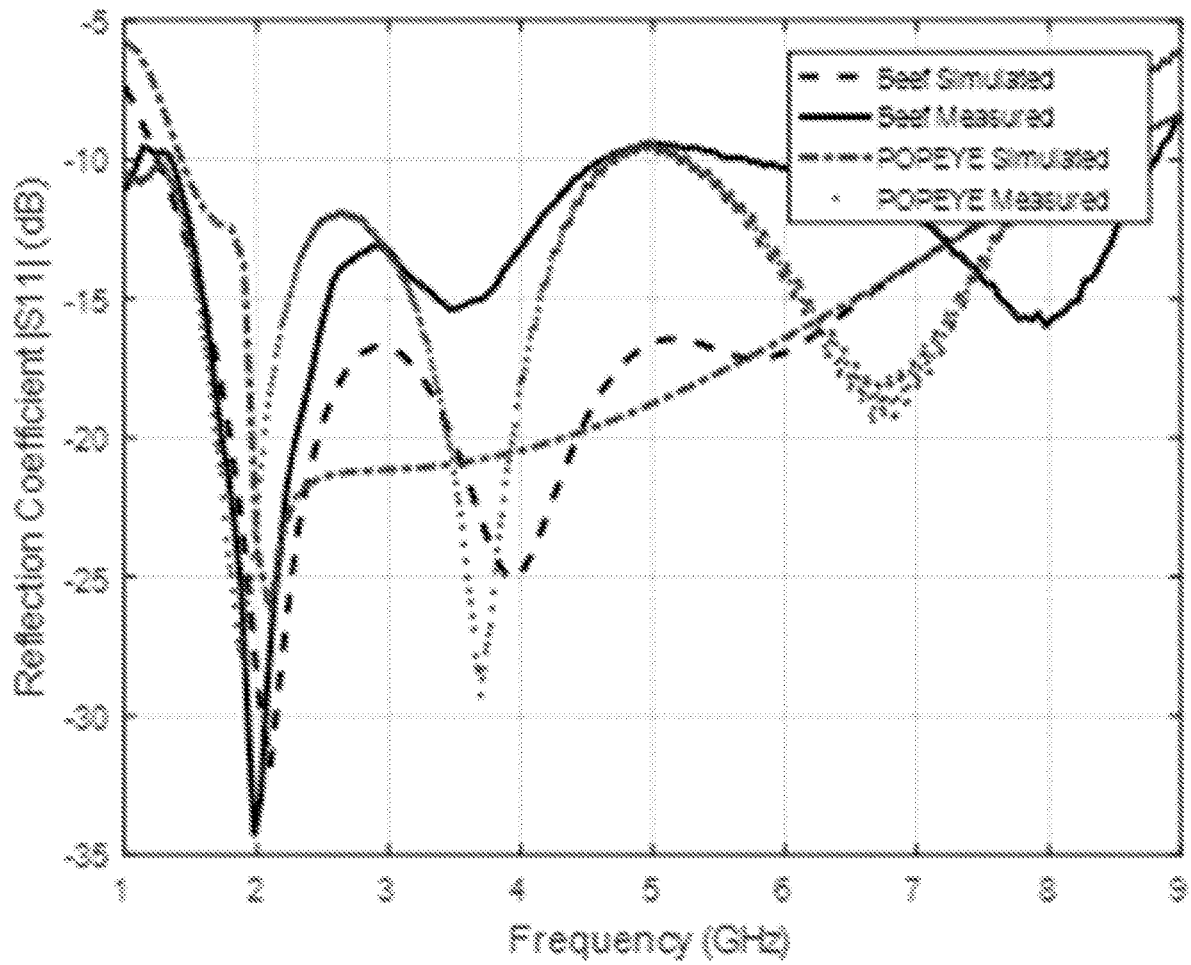
FIG. 23 is a plot of the measured and simulated reflection coefficient for the phantoms shown in FIGS. 19 and 20.

The simulated vs. measured reflection coefficient performance of the BMA 50 is shown in FIG. 23. Two simulation setups were considered with the tissue-emulating box 55 of FIG. 22 emulating the POPEYE and ground-beef properties. Accordingly, two measurement setups were considered that employed the POPEYE and ground-beef phantoms of FIGS. 19 and 20, respectively.

As seen in FIG. 23, the bio-matched antenna 50 matches remarkably well across the 1 to 9 GHz bandwidth, despite the POPEYE phantom having only ~60% of the permittivity of the ground beef. Notably, measurements are in very good agreement with simulations, with the BMA 50 only being slightly detuned, most likely due to slight water leakage. When placed upon the POPEYE phantom (FIG. 19), the reflection coefficient remains below −10 dB across the bandwidth of 1.0-8.01 GHz, with the exception of a small section that is −9 dB from 4.72-5.25 GHz. When placed upon the ground beef phantom (FIG. 20), the reflection coefficient remains below-10 dB across the bandwidth of 1.35-8.81 GHz, with the exception of a small section that is-9 dB from 4.60-5.65 GHz.

Figure 24:
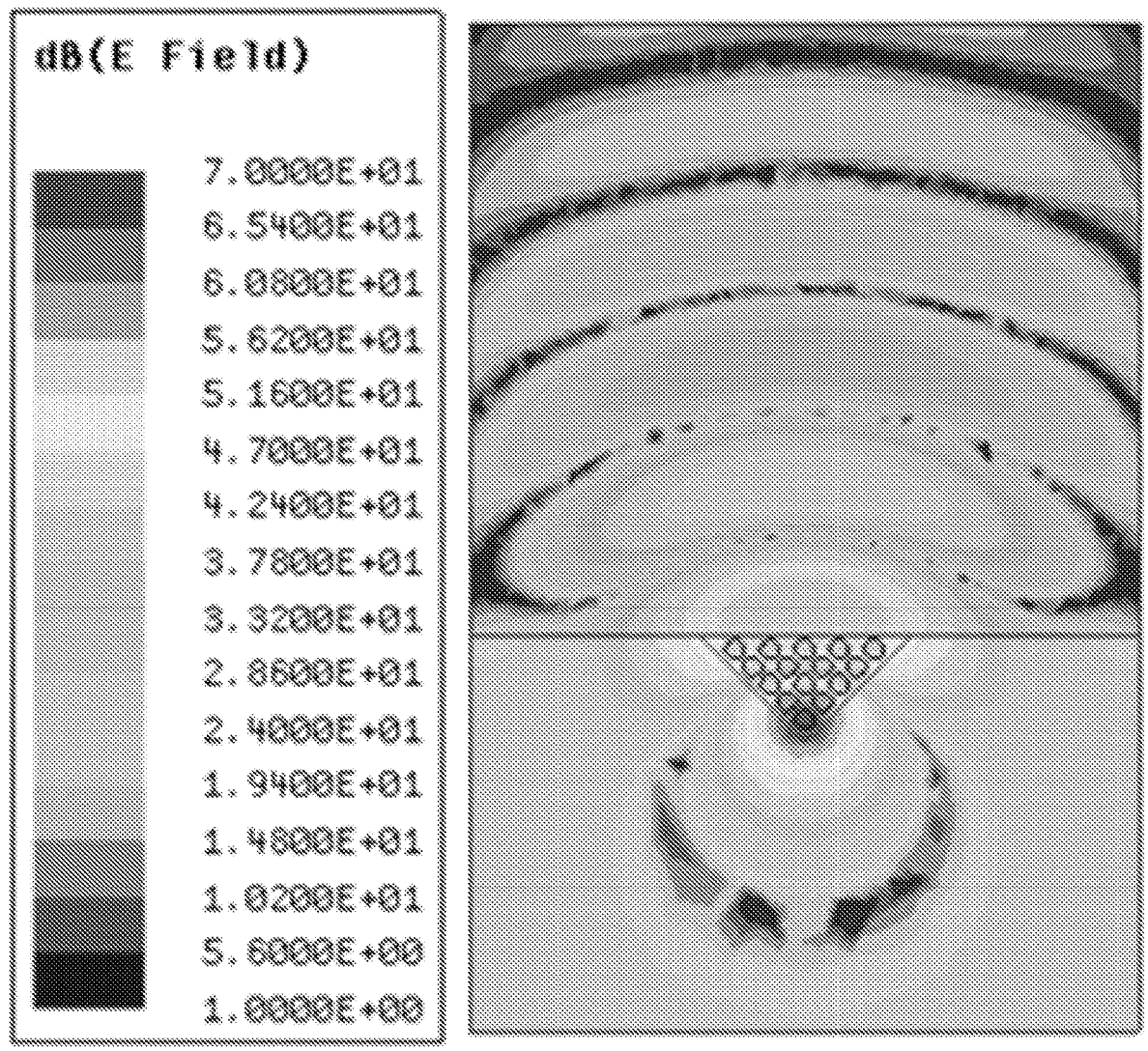
FIG. 24 shows the electric fields radiated by the BMA inside of the tissue-emulating phantom of FIG. 22 at 2.4 GHz.

The electric fields radiated by the BMA 50 inside the tissue-emulating phantom of FIG. 22 at 2.4 GHz are shown in FIG. 24. For this particular example, the POPEYE electrical properties were used in simulations. As seen, the bio-matched antenna 50 keeps the orientation of the fields normal to the placement of the BMA 50, allowing them to propagate deep into the tissue in a directive manner.

Simulations and measurements were carried out to assess the feasibility of the BMA 50 in communicating with both subcutaneous (<5-mm-deep) and deep-tissue (>5-mm-deep) wireless implants. The ISM frequency of 2.4 GHz was again considered in these studies. To enable implantation, the ground beef phantom of FIG. 20 was employed. Accordingly, the simulation setup of FIG. 22 was set to emulate the ground beef properties of FIG. 20.

Figure 25:
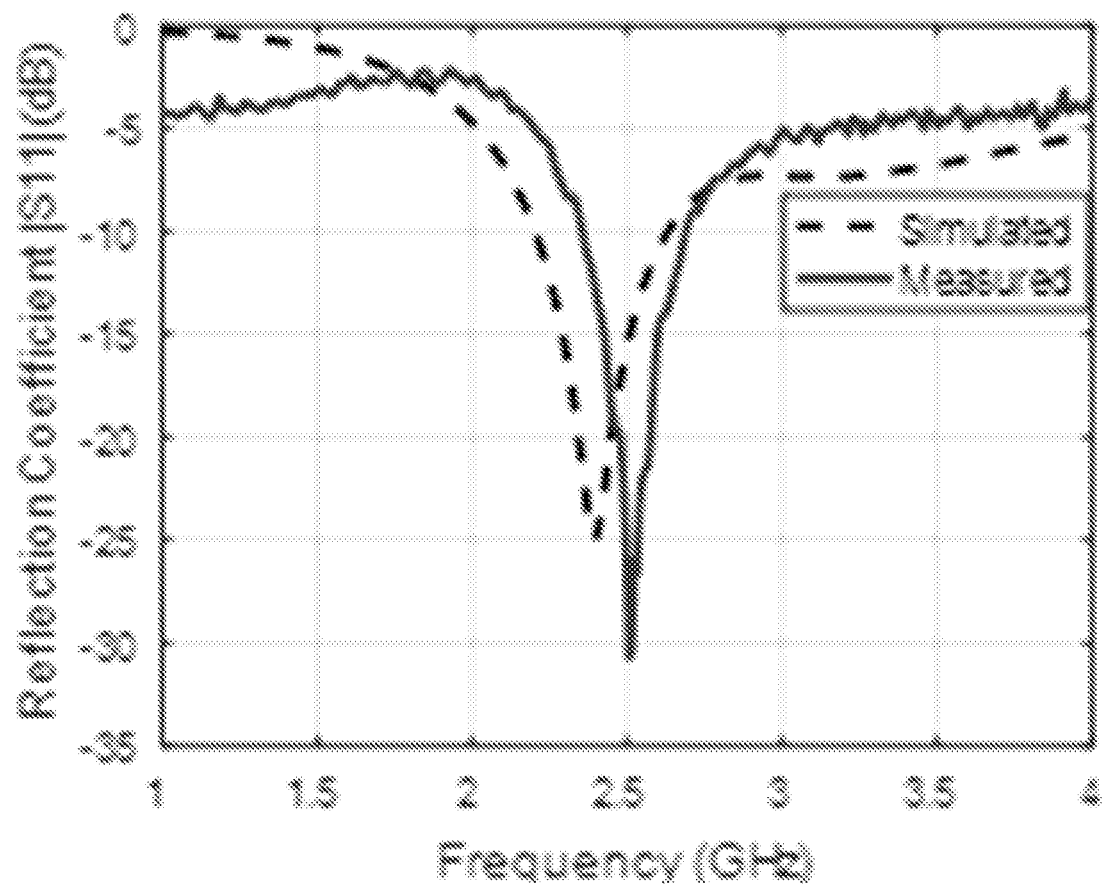
FIG. 25 shows the simulated vs. measured reflection coefficient of an implantable patch antenna that was used during an experiment to test the BMA antenna shown in FIG. 15.

To account for the wireless implant, a proof-of-concept implantable antenna was employed (not shown). This antenna exhibited a patch geometry with a footprint of 18.5 mm×11 mm, and was not miniaturized or optimized in any way. The prototype was milled upon a 1.27 mm thick Rogers TMM 13$i$ substrate ($\varepsilon_r$=12.85 and tan δ=0.0019), and was further coated with a 0.5 mm layer of polydimethylsiloxane (PDMS) ($\varepsilon_r$=2.8 and tan δ=0.001) to ensure biocompatibility. The simulated vs. measured reflection coefficient of this implantable patch is shown in FIG. 25. As expected, the antenna operates in the 2.4 GHz ISM band, with good agreement between simulations and measurements. The slight detuning in the measured reflection coefficient most likely stems from inaccuracies in the thickness of the manually-employed PDMS coating.

Figure 26A:
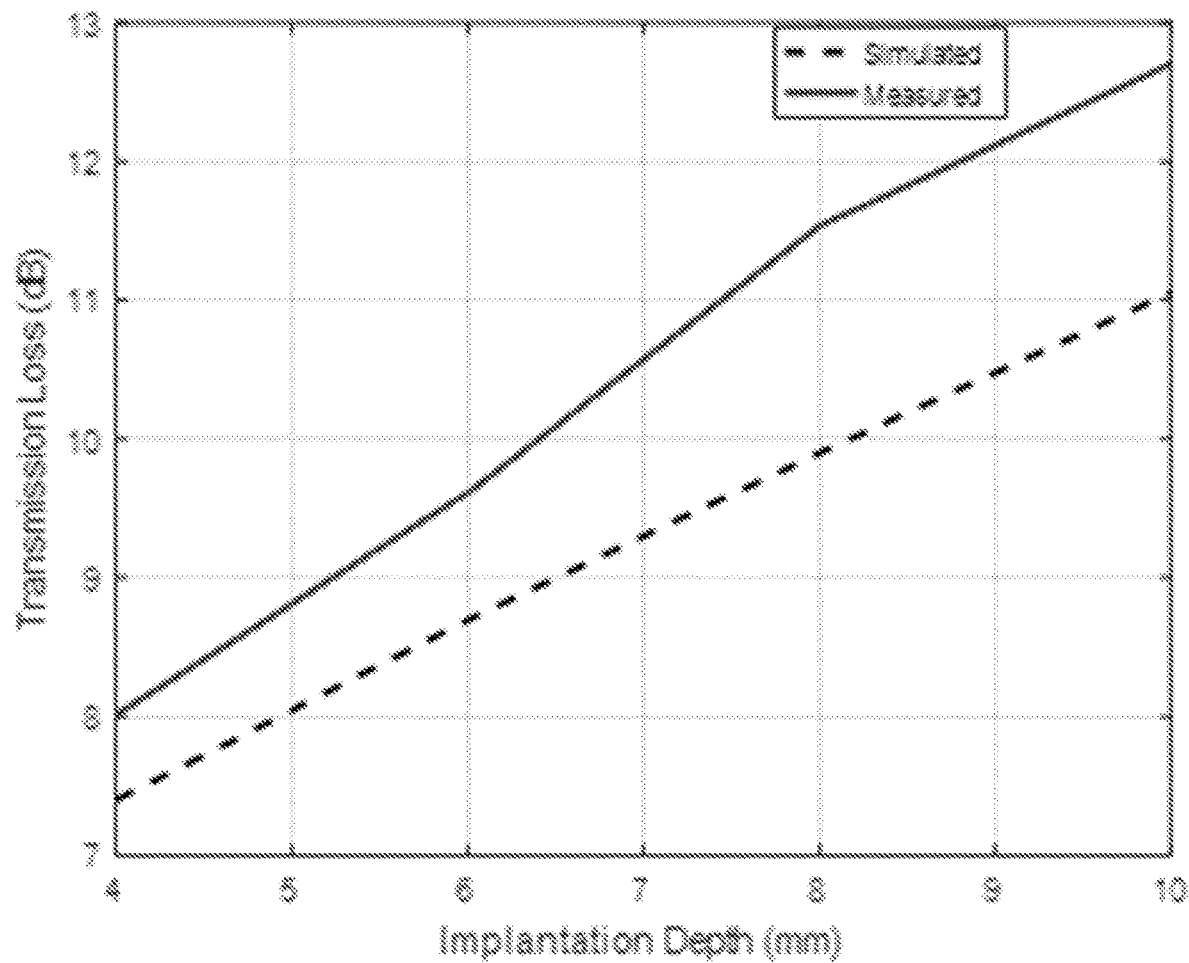
FIGS. 26A and 26B are plots of transmission loss vs. implantation depth results between the BMA and the patch antenna implanted subcutaneously and deep into tissue, respectively.
Figure 26B:
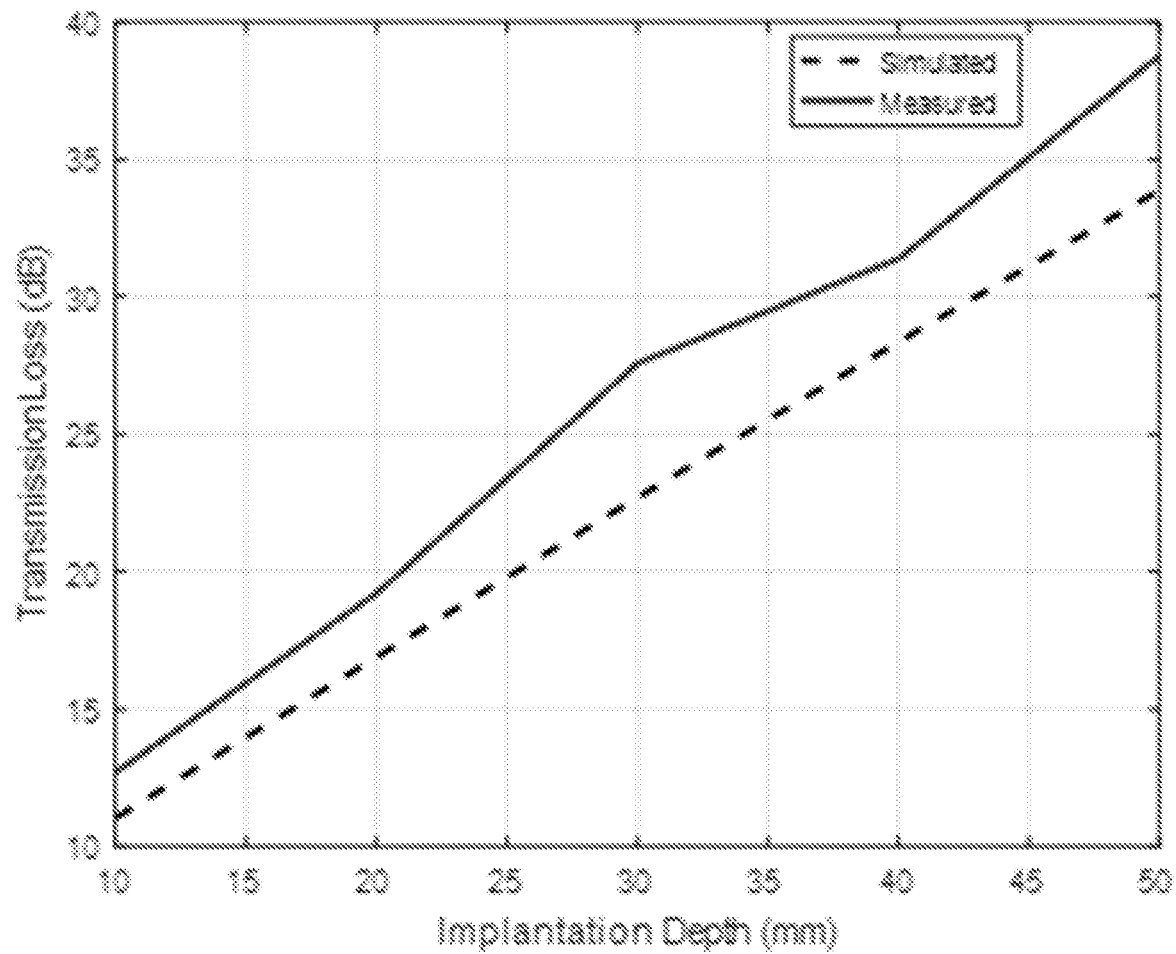

FIGS. 26A and 26B are plots of transmission loss results between the BMA 50 and the patch antenna implanted subcutaneously and deep into tissue, respectively, as a function of implantation depth. In measurements, layers of beef were added incrementally upon the patch to achieve the desired implantation depth. Expectedly, as implantation depth increases, transmission loss to the underlying implant increases linearly on a dB scale. Notably, great agreement is observed between simulations and measurements. Measured loss was, on average, ~1 dB higher than simulation loss for subcutaneous testing and ~3.3 dB higher than simulation loss for deep-tissue testing. Such discrepancies are expected and can be attributed to fabrication errors (e.g., thickness of the manually-employed PDMS coating) and/or uncertainties in the measurement setup (e.g., exact implantation depth, positional and angular misalignment, etc.).

Importantly, and as also highlighted in Tables III and IV above, the BMA 50 considerably outperforms state-of-the-art on-body antenna designs for communication with wireless implants. Considering the subcutaneous implant scenario of FIG. 26A, the BMA 50 offers at least 14.2 dB lower loss than what has been reported with other known designs. At a depth of 2 cm (see FIG. 26B) the BMA 50 has a mere 19.21 dB of loss as compared to some known designs which had 30 dB of loss. Although such designs have an additional mismatch loss between free space and biological tissues, the BMA 50 has at least 12.78 dB lower transmission loss even when subtracting out any losses associated with mismatch.

Figure 27:
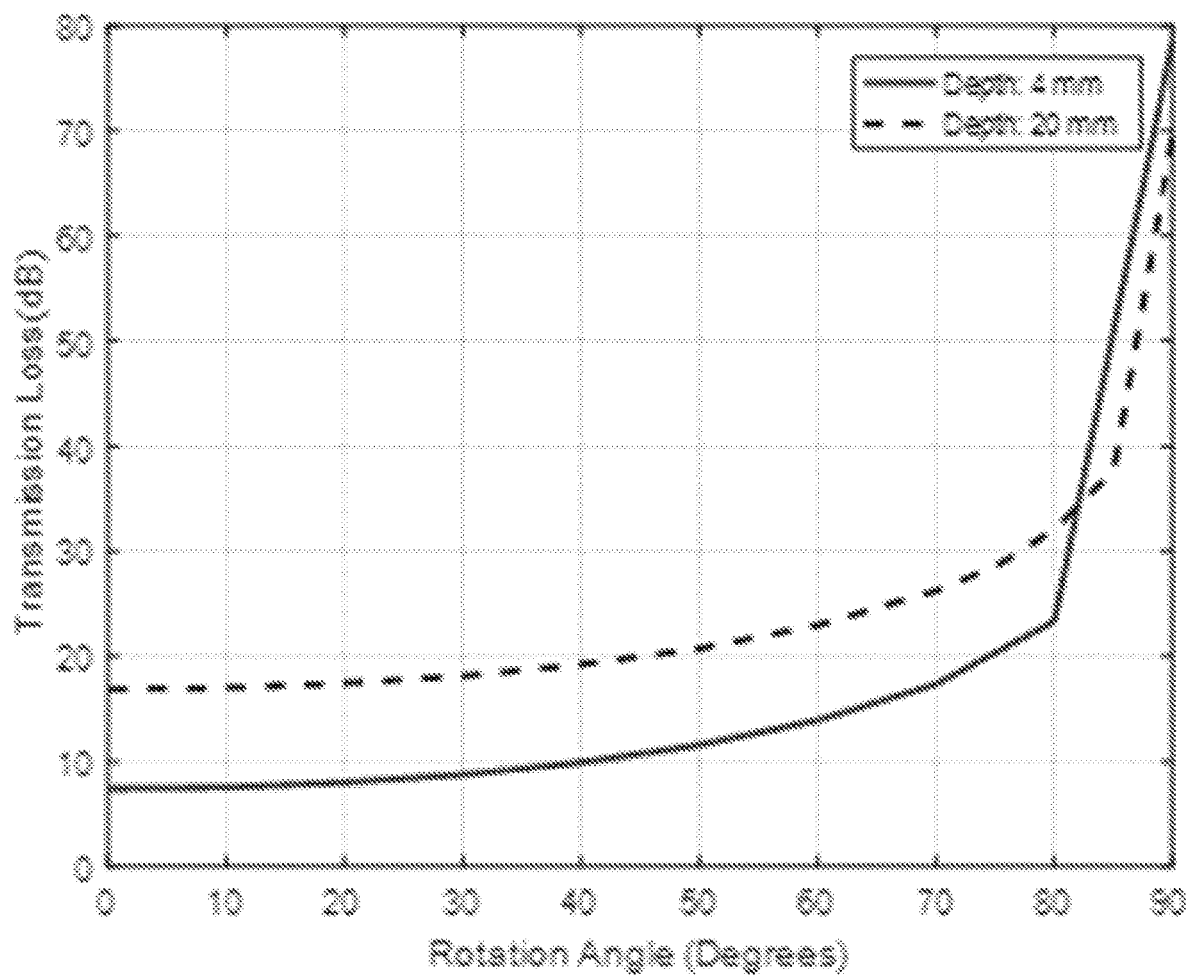
FIG. 27 is a plot of transmission loss vs. implantation depth results between the BMA and the implanted patch antenna after the BMA has been rotated about its central axis.

The BMA 50 maintains a linear polarization that causes it to be dependent on rotational alignment for communication with wireless implants. To assess this effect on the associated transmission loss, simulation studies were performed at 2.4 GHz. To do so, the setup of FIG. 22 was employed, with the ground beef electrical properties (see FIG. 20) assigned to the tissue-emulating box. The BMA 50 was placed right upon the air-tissue interface, while the implantable patch antenna (not shown) was immersed: a) 4 mm (subcutaneously), and b) 20 mm (deep-tissue) inside the phantom. The BMA 50 was subsequently rotated about its central axis and the transmission loss between the BMA 50 and the implanted patch was recorded. FIG. 27 is a plot of transmission loss at 2.4 GHz between the BMA 50 and the implantable patch antenna immersed at 4 mm and 20 mm depth as a function of rotational misalignment. As seen, perfect alignment yields 7.4 dB of transmission loss in the subcutaneous scenario and 16.9 dB of transmission loss in the deep-tissue implantation scenario. For both depths, the bio-matched antenna 50 can be misaligned by up to 45° and remain within 3 dB of the perfectly matched polarization. At an angular offset of 90°, the transmission loss increases significantly. This is attributed to the fact that the bio-matched antenna's polarization and the patch antenna's polarization are orthogonal to each other. Therefore, it is recommended to utilize circularly polarized implantable antennas in biomedical telemetry scenarios where polarization cannot be adequately controlled.

Figure 28A:
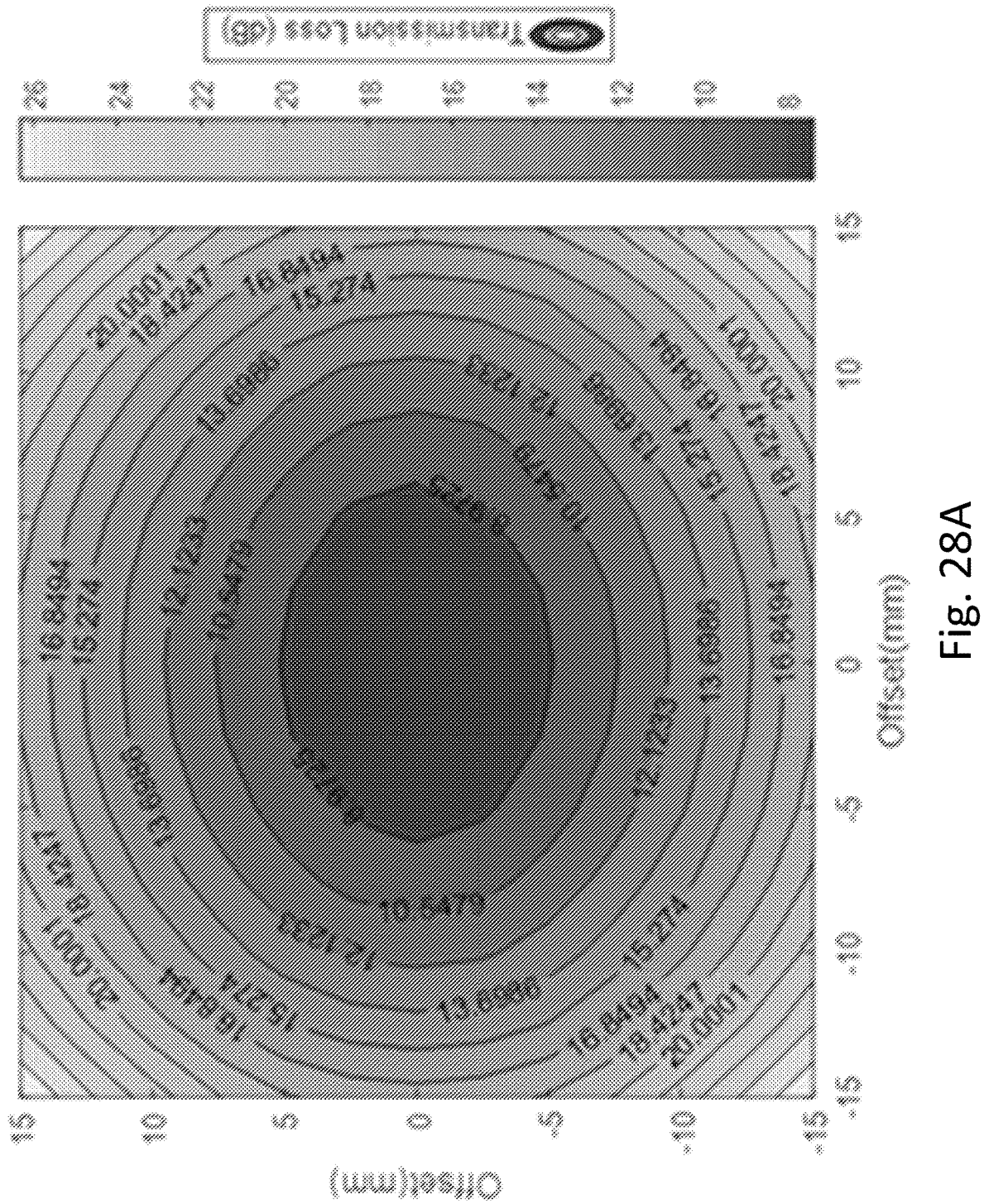
FIGS. 28A and 28B are contour maps for transmission loss between the BMA and the implanted patch antenna for subcutaneous and deep-tissue implantation, respectively, after the bio-matched antenna has been misaligned by up to 15 mm.
Figure 28B:
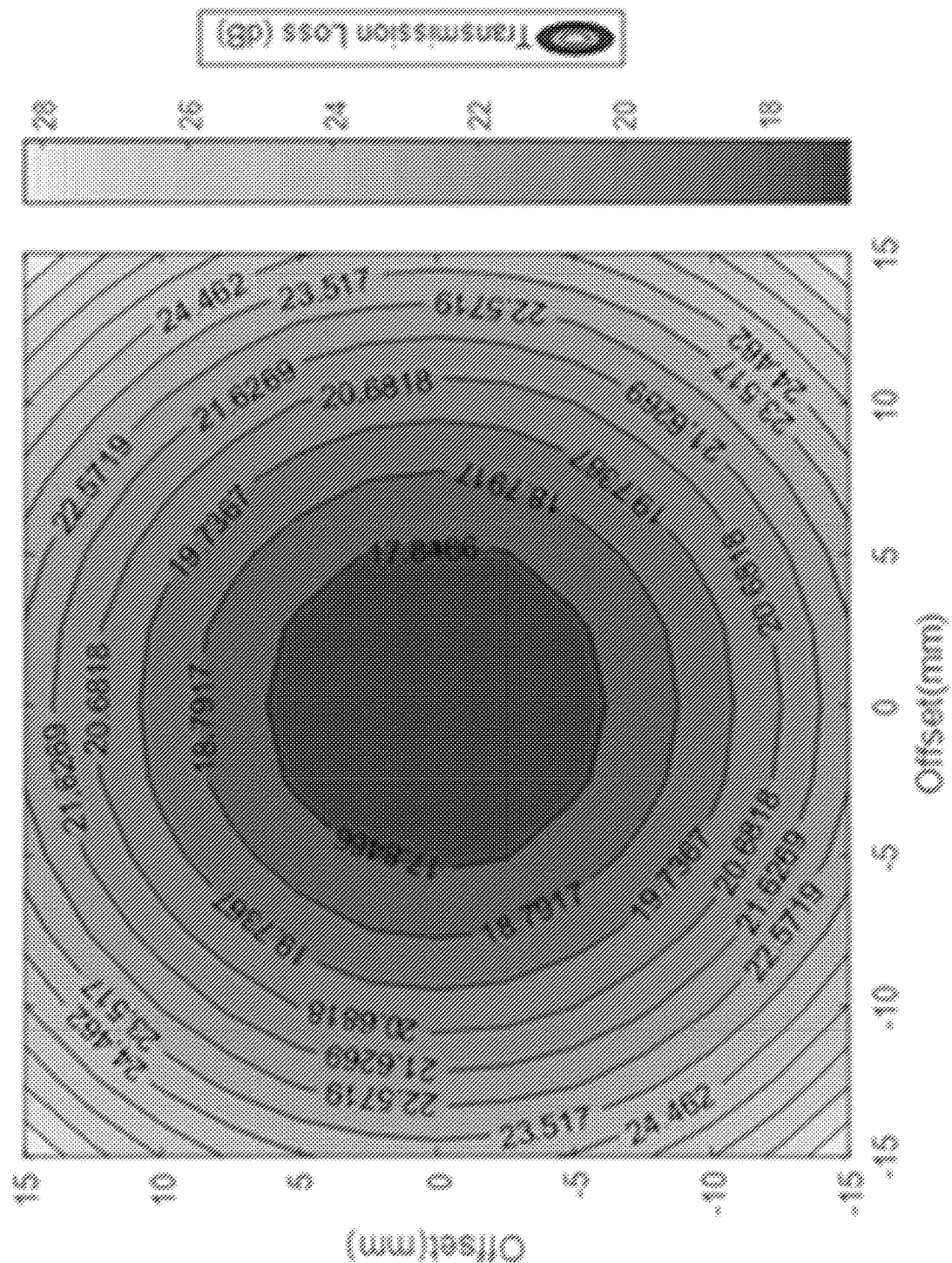

Similarly, transmission loss between the bio-matched antenna 50 and the wireless implant depends on positional alignment between the two. To assess this effect, the BMA 50 was again placed right upon the air-tissue interface, while the implantable patch antenna was immersed: a) 4 mm (subcutaneously), and b) 20 mm (deep-tissue) inside the phantom. The BMA 50 was subsequently misaligned by up to 15 mm in the x-direction and y-direction (defined in FIG. 22). To reduce simulation time, only one spatial quadrant was simulated and then was duplicated for the remaining spatial quadrants. FIGS. 28A and 28B are contour plots of the transmission losses for subcutaneous and deep-tissue implantation scenarios, respectively, for the bio-matched antenna.

The contour plots of FIGS. 28A and 28B show relatively radially isotropic dependence on alignment for deep tissue operation and greater dependency on Y-directional alignment for subcutaneous operation. This matches intuition as the patch antenna is longer along its Y-direction (18 μm) than in the X-direction (11.5 μm). Moreover, positional alignment appears to be more critical in the subcutaneous rather than the deep-tissue scenario. This was expected as the bio-matched antenna's beam size grows as a function of the radial depth squared. Therefore, less radiation will be developed spatially at shallower implantation depths. Overall, the bio-matched antenna 50 in accordance with this embodiment can be misaligned by a maximum of 7.5 mm for a 4-mm-deep implant and by a maximum of 12.5 mm for a 20-mm-deep implant and still be within 3 dB of optimal power transfer.

Figure 29:
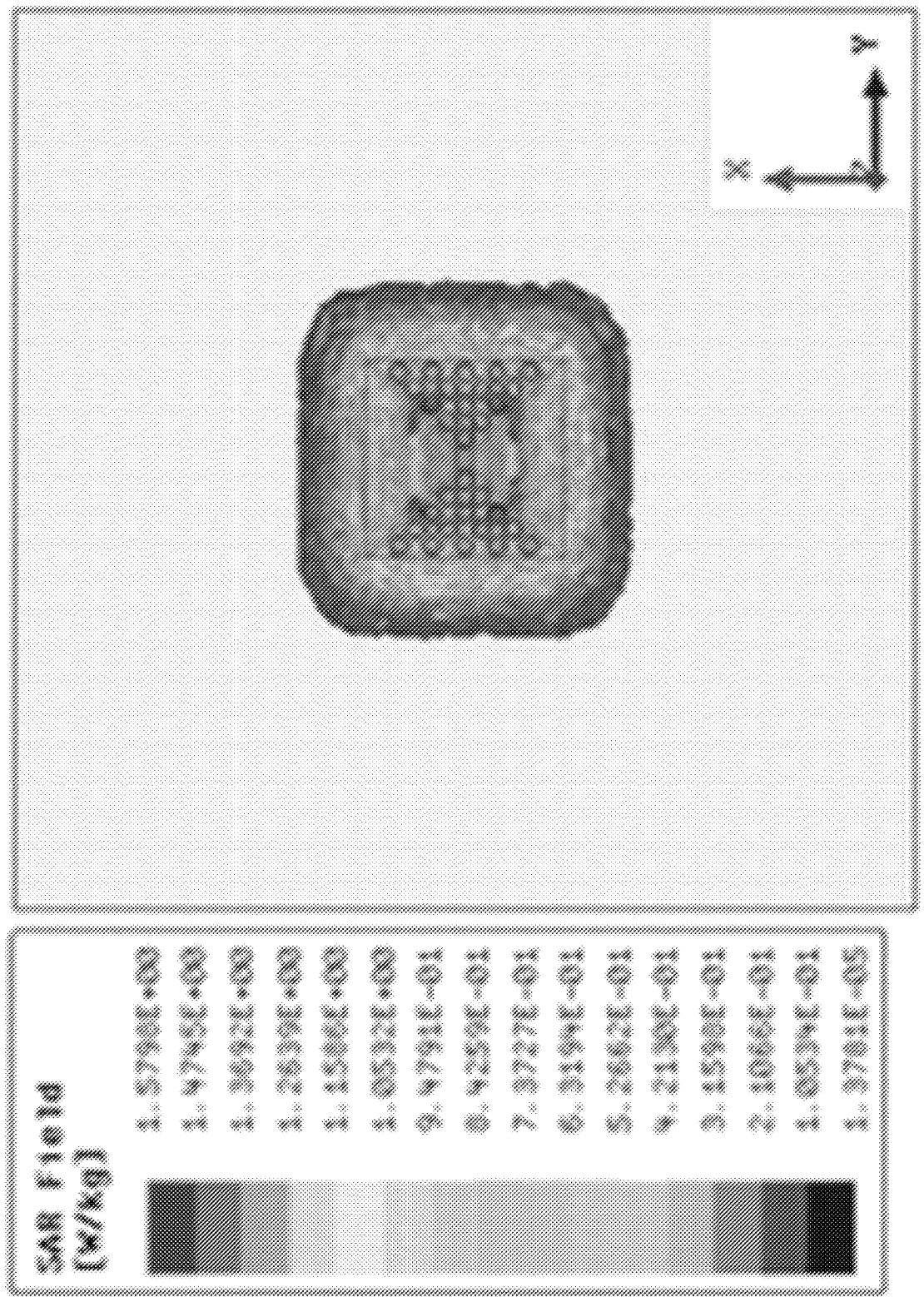
FIG. 29 is a Specific Absorption Rate (SAR) distribution for SAR simulations performed for the BMA using the simulation setup of FIG. 22 and the ground beef electrical properties of the phantom shown in FIG. 20.

SAR simulations were performed for the bio-matched antenna 50 using the simulation setup of FIG. 22 and the ground beef electrical properties of the phantom shown in FIG. 20. The mass density used for the phantom was 1010 kg/m³, which corresponds to the mass density of human skin tissue. The 2.4 GHz SAR distribution averaged over 1 g ($SAR_{1g}$) of tissue is shown in FIG. 29. Assuming an 8.57 dBm input power for the BMA 50, the maximum value of $SAR_{1g}$ is found to be equal to ~1.6 W/kg. That is, input power levels as high as 8.57 dBm guarantee conformance with the strictest safety guidelines imposed by the FCC (i.e., $SAR_{1g} \leq 1.6$ W/kg).

V. Second Experimental Setup

A. BMA Design and Manufacturing

Leveraging the theoretical modeling and design guidelines of the framework described in sections I.-III, his section presents an approach for designing a novel BMA of comparable size to that disclosed in the aforementioned article and provisional application, but with improved bandwidth and transmission loss. Section III.A indicated that the high frequency cutoff could be improved through implementing smaller unit cells, whereas Section III.B showed that increasing the size of the antenna can lower the first resonant frequency of the antenna, thus lowering the low cutoff frequency. Lastly, the analysis of unit cells discussed above with reference to FIG. 14 showed that hexagonal unit cells are optimal for transmission. Implementing these improvements results in an improved antenna with only a minor increase in antenna size.

With the above in mind, a BMA is designed that employs the hexagonal unit cell of FIG. 6B. In this example, the BMA has a unit cell size of 2.476 mm with a hexagon diameter of 1.3 mm. Its height is 11.95 mm and it has an angle of 45°, yielding a final base of size 24.9×24.9 mm². For comparison, the antenna reported in the aforementioned article employed the cylindrical unit cell of FIG. 6A of size 3.636 mm. The BMA had a height of 10 mm with an angle of 45°, yielding a final base size of 22×22 mm².

B. BMA Prototype and Measurement Setup

For fabrication, the BMA design of Section V.A was 3-D printed using stereolithography. This was accomplished using a Formlabs Form 2 printer and rigid resin. The rigid resin was chosen for its high precision and stiffness for small sizes. Its relative permittivity and loss tangent were found to be in the range of ~3-4 and ~0.01, respectively. To simplify the design, it was assumed that it had comparable characteristics to polylactic acid (PLA) ($\varepsilon_r$=3.549, tan δ=0.001). Once printed, the hexagonal holes were filled with water and the sides were covered with copper tape as shown in FIG. 1.

Both SPEAG's POPEYE leg phantom (FIG. 19) and 80% lean ground beef (FIG. 20) were used as phantoms to test the BMA.

C. Results

Figure 30A:
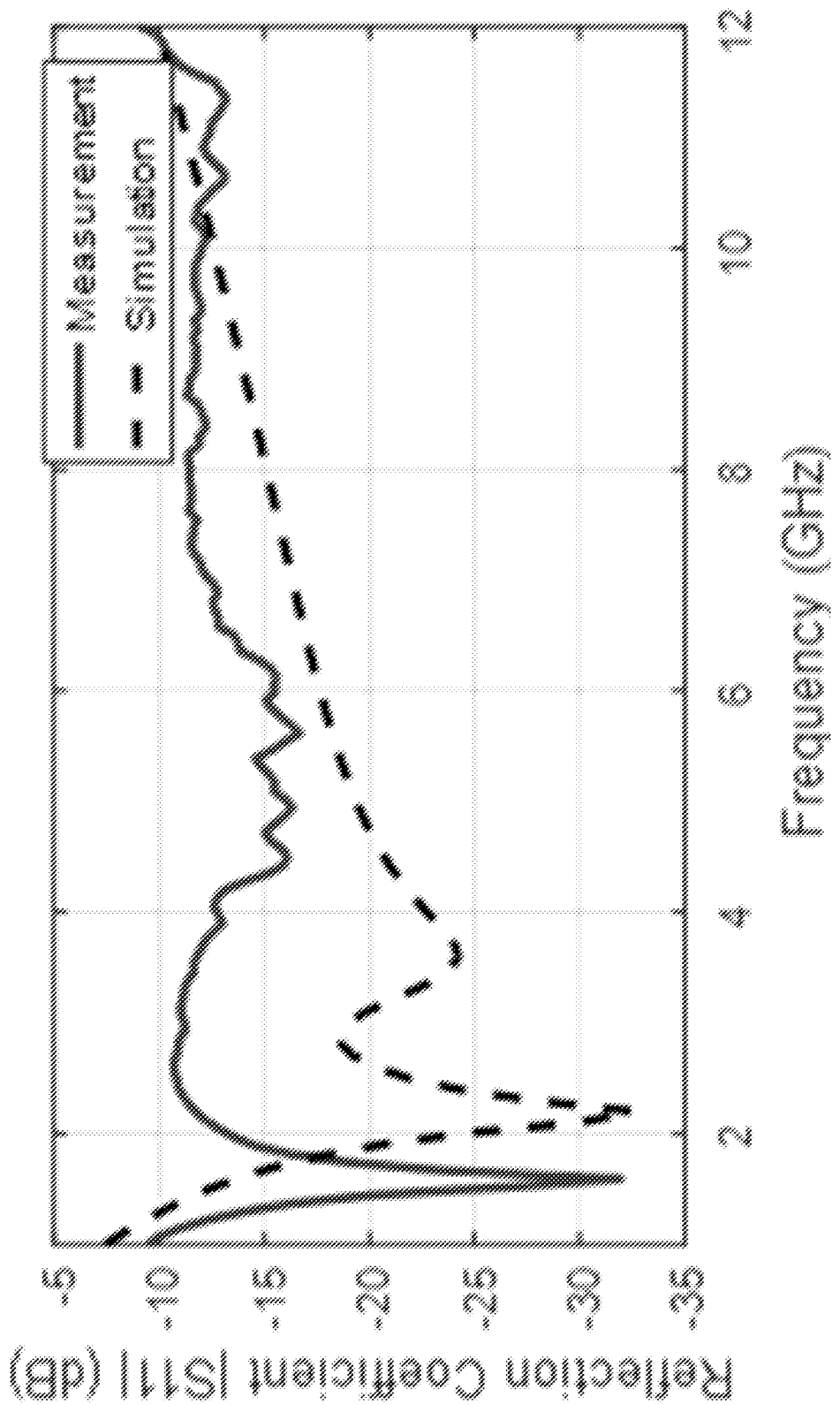
FIGS. 30A and 30B are superimposed plots of the measured and simulated reflection coefficients of the reflection coefficient against POPEYE and ground beef phantoms, respectively, for a second experimental setup for the BMA.
Figure 30B:
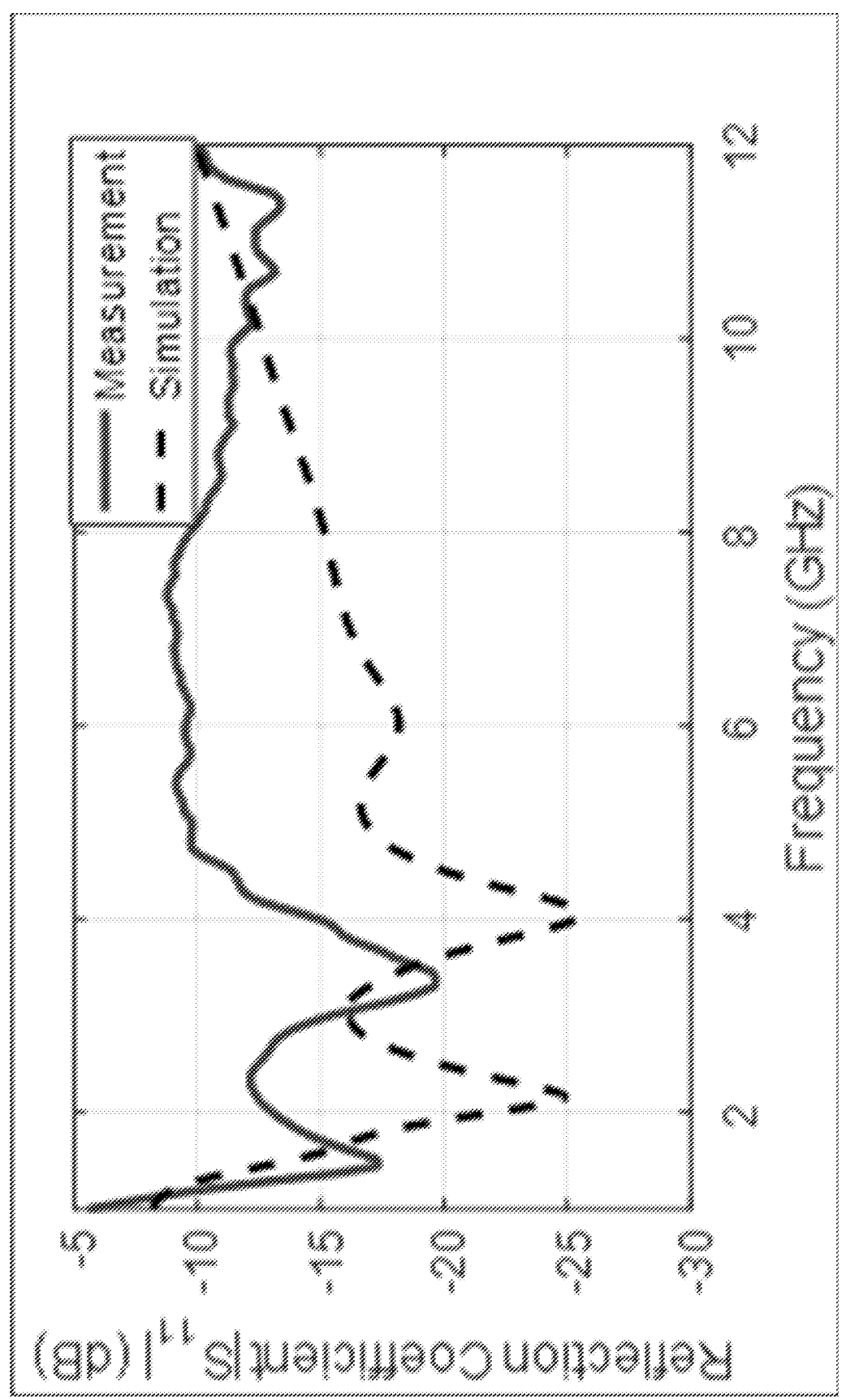

Measurements and simulations of the BMA's reflection coefficient against the POPEYE and ground beef phantoms are superimposed in FIGS. 30A and 30B, respectively. The measured bandwidth against the POPEYE phantom is 11.12:1, whereas the original design of the aforementioned article was merely 6.07:1.

Figure 31:
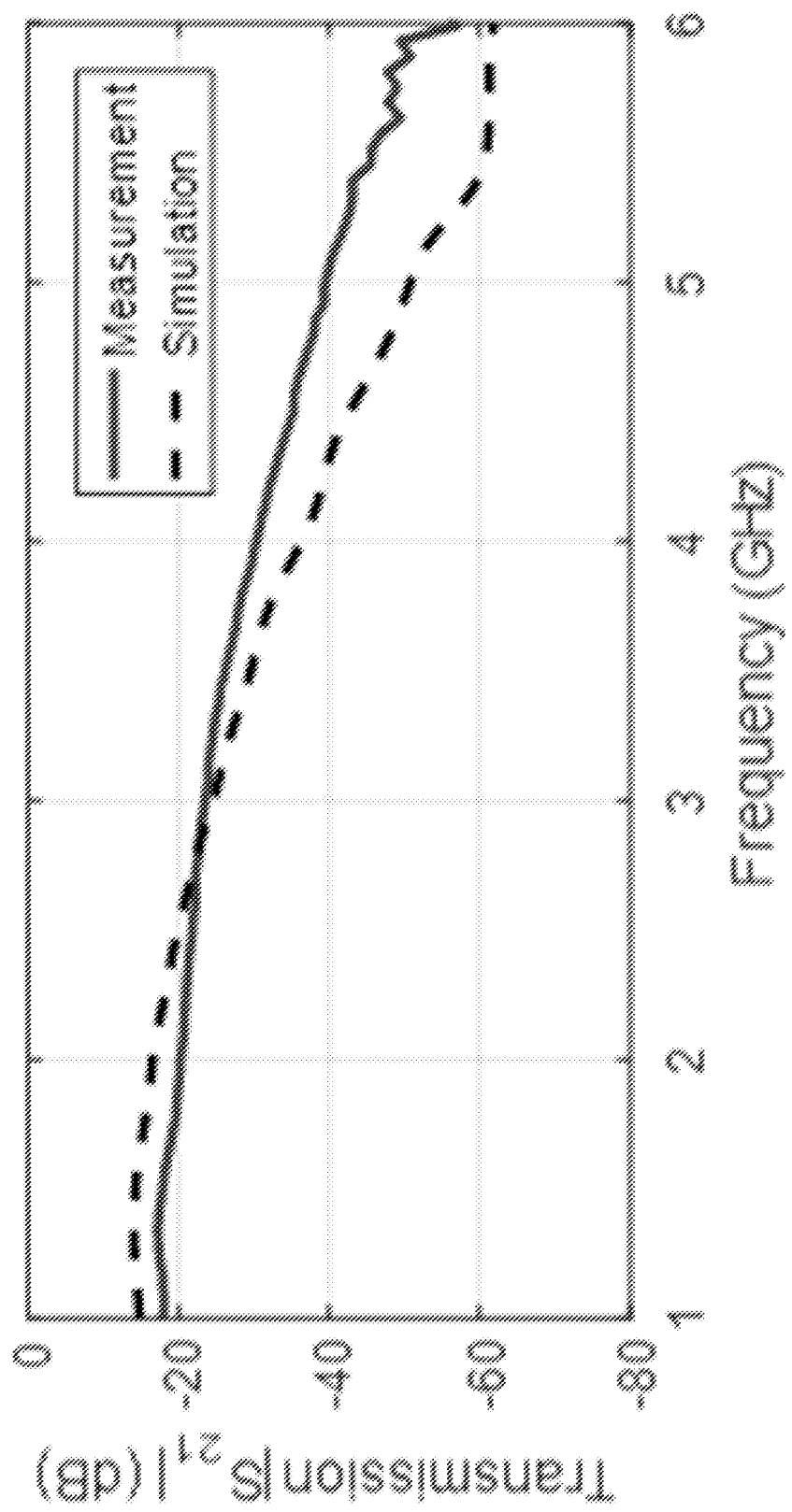
FIG. 31 is a plot of the measured and simulated transmission coefficients through beef as a function of frequency for the second experimental setup of the BMA placed on either side of the ground beef phantom shown in FIG. 20 having a thickness of 3 cm.

To measure the transmission loss, the ground beef phantom was made to be 3 cm thick and two identical BMAs were placed on either side of it. FIG. 31 is a plot of the measured and simulated transmission coefficients through beef as a function of frequency. As can be seen in FIG. 31, the measured and simulated transmission coefficients are in good agreement. Most likely, there was slight water leakage that caused there to be worse performance than simulation at lower frequencies and better performance at higher frequencies. Beyond 6 GHz, the measurements are in the noise floor and are thus not reported in this disclosure. At 2.4 GHz, the transmission loss is a remarkable 21.4 dB, which is 6.2 dB lower than the transmission loss reported in the aforementioned article.

VI. Additional Considerations

The BMA's 1 and 50 can be used in a variety of applications and can have a variety of configurations. With their low loss communication to implanted medical devices, the BMAs 1, 50 are well-suited for wireless biomedical telemetry, but have many other uses as well. For example, they can be used as an on-body interrogator for glucometers, neural implants, ingestible sensors and more. With their ability to efficiently send power to the implant, the BMAs 1, 50 could be used for neural stimulation. They can also be used to harvest power for implant antennas and the associated circuitry. Since the transmission loss of the BMAs 1, 50 is minimal, they are excellent candidates for delivering wireless power to implanted devices. This can be used to potentially power pacemakers and lead to batteryless implants.

The BMAs 1 and 50 may also be used in imaging and radiometry applications. Due to their minimal transmission loss, the BMAs 1 and 50 also allow for precise mapping and identification of cancerous tumors as well as some forms of spectroscopy. They can also be used for ablation and hyperthermia applications. The BMAs 1 and 50 can be used to heat biological tissues efficiently with their excellent match to biological tissues. A combination of the above works well since the BMAs 1, 50 are so broadband. The BMAs 1, 50 are also suitable for use for non-biological testing in that they can be used to match to other water-based materials, such as soil, for example. The above listing of examples of different applications for which the BMAs 1 and 50 are suitable for use is not exhaustive, as will be understood by those of skill in the art in view of the description provided herein.

Figure 32:
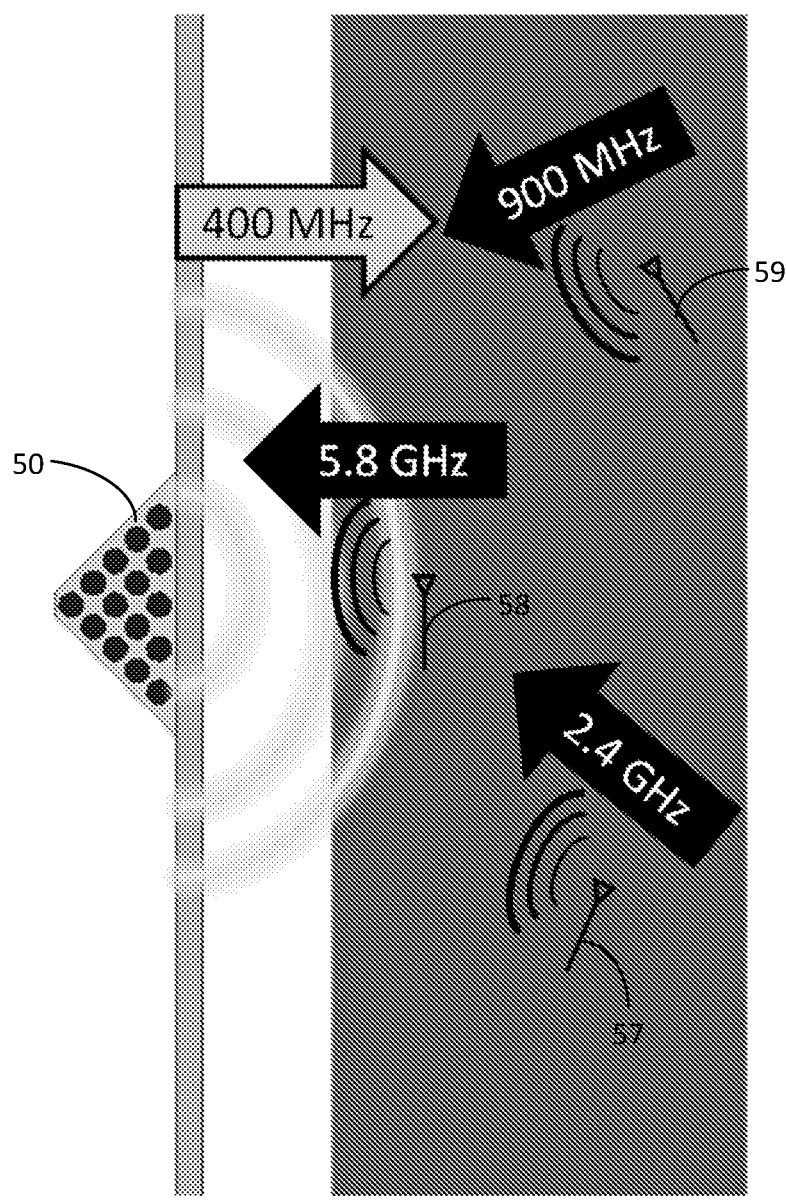
FIG. 32 is a pictorial illustration of the BMA in accordance with a representative embodiment employed with multiple implant devices that transmit over different channels (ISM bands) of 2.4 GHz, 5.8 GHz and 900 MHz.

FIG. 32 is a pictorial illustration of the BMA 50 in accordance with a representative embodiment employed with multiple implant devices 57-59. In accordance with this embodiment, the BMA 50 illuminates in MedRadio (400 MHZ). The implant devices 57-59 rectify the 400 MHz signal and transmit out different channels (ISM bands) of 2.4 GHZ, 5.8 GHz and 900 MHz, respectively.

Figure 33:
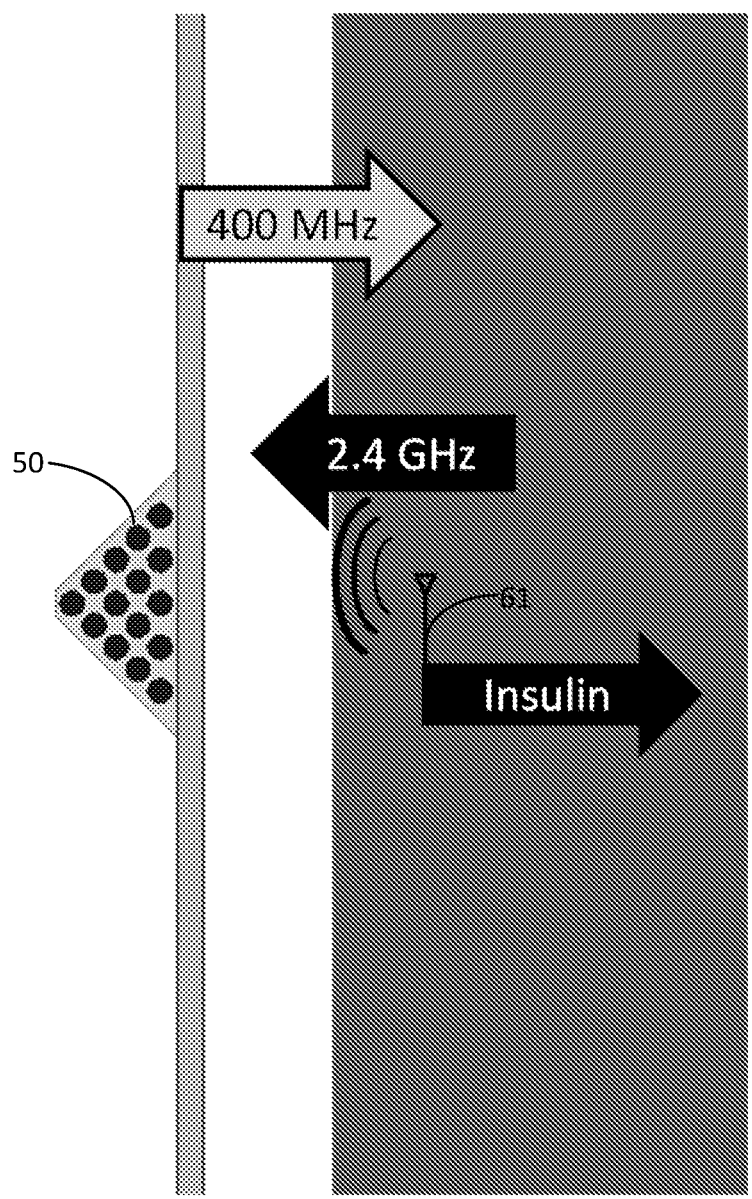
FIG. 33 is a pictorial illustration of the bio-matched antenna in accordance with a representative embodiment in which the bio-matched antenna illuminates in MedRadio (400 MHz) to wirelessly electrically charge an implant device that has a built-in glucometer for wireless telemetry.

FIG. 33 is a pictorial illustration of the BMA 50 in accordance with a representative embodiment in which the BMA 50 illuminates in MedRadio (400 MHZ) to wirelessly electrically charge an implant device 61 that has a built-in glucometer for wireless telemetry. The implant device 61 transmits at 2.4 GHz to communicate with the implant device 61.

Figure 34B:
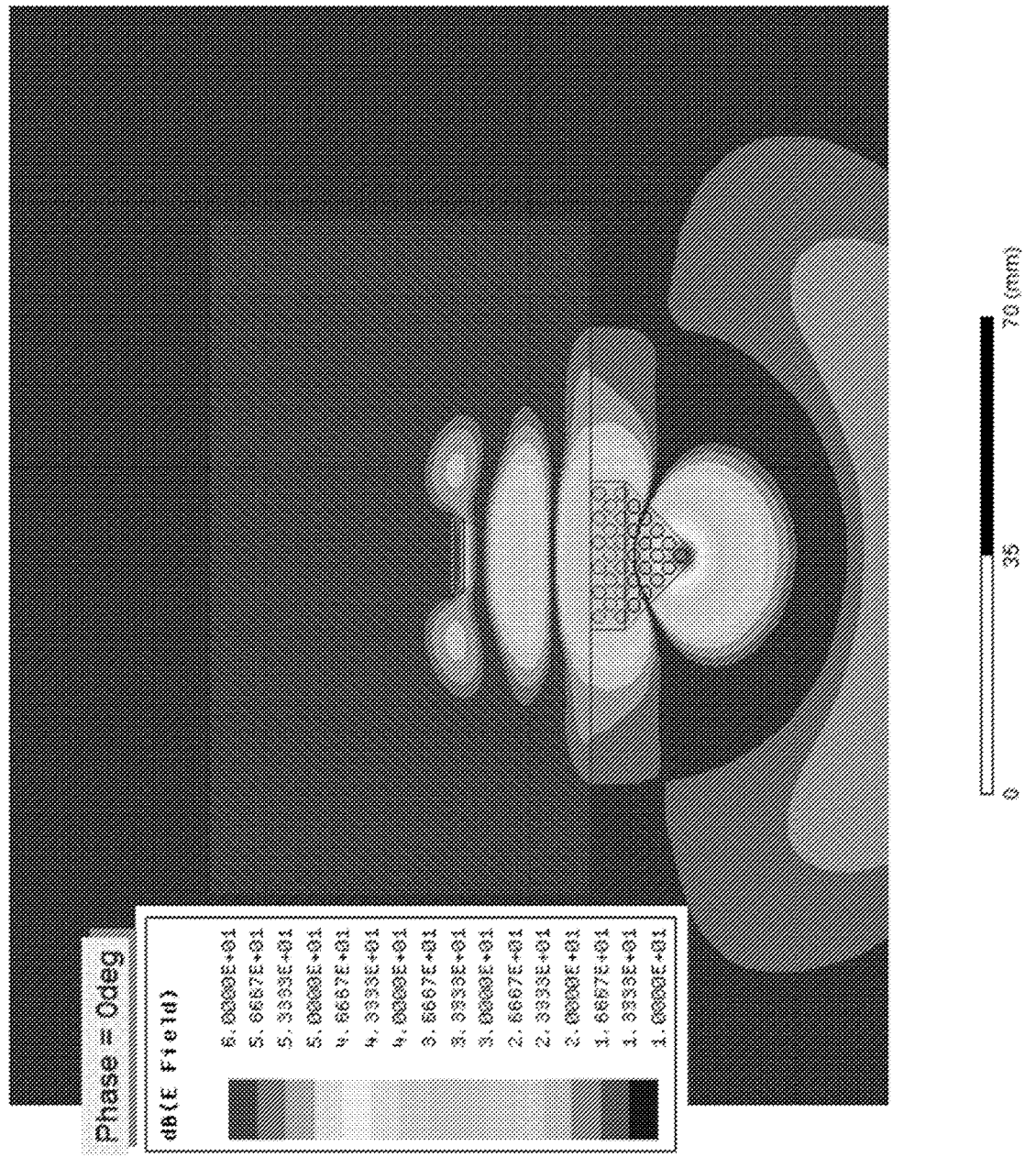
FIGS. 34B and 34C show the electric field and SAR field data, respectively, for preliminary simulations that result in the maximum input power increasing to 14.9 dBm.
Figure 34C:
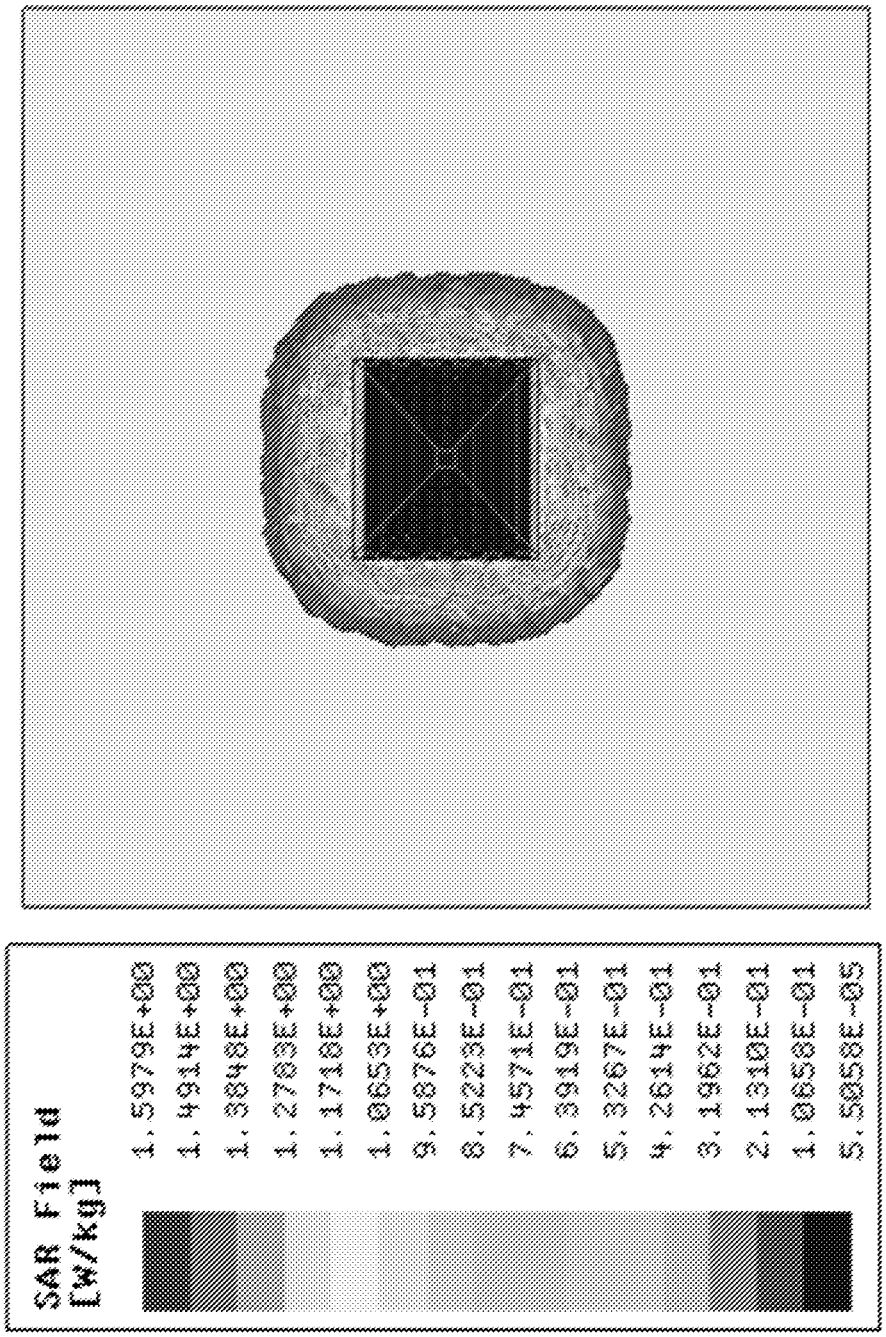

FIG. 34A is a side plan view diagram of the BMA 50 in accordance with another representative embodiment equipped with a small buffer lens 62 that is made of the same dielectric material that is used to make the BMA 50. FIGS. 34B and 34C show the E field and SAR field data, respectively, for preliminary simulations. The maximum input power has increased to 14.9 dBm. There is a slight decrease in |$S_{21}$| from −16.5 dB to −19.8 dB. The BMA 50 is also slightly detuned with an |$S_{11}$| of −8.8 dB. However, these can be overcome with further optimization.

Figure 35:
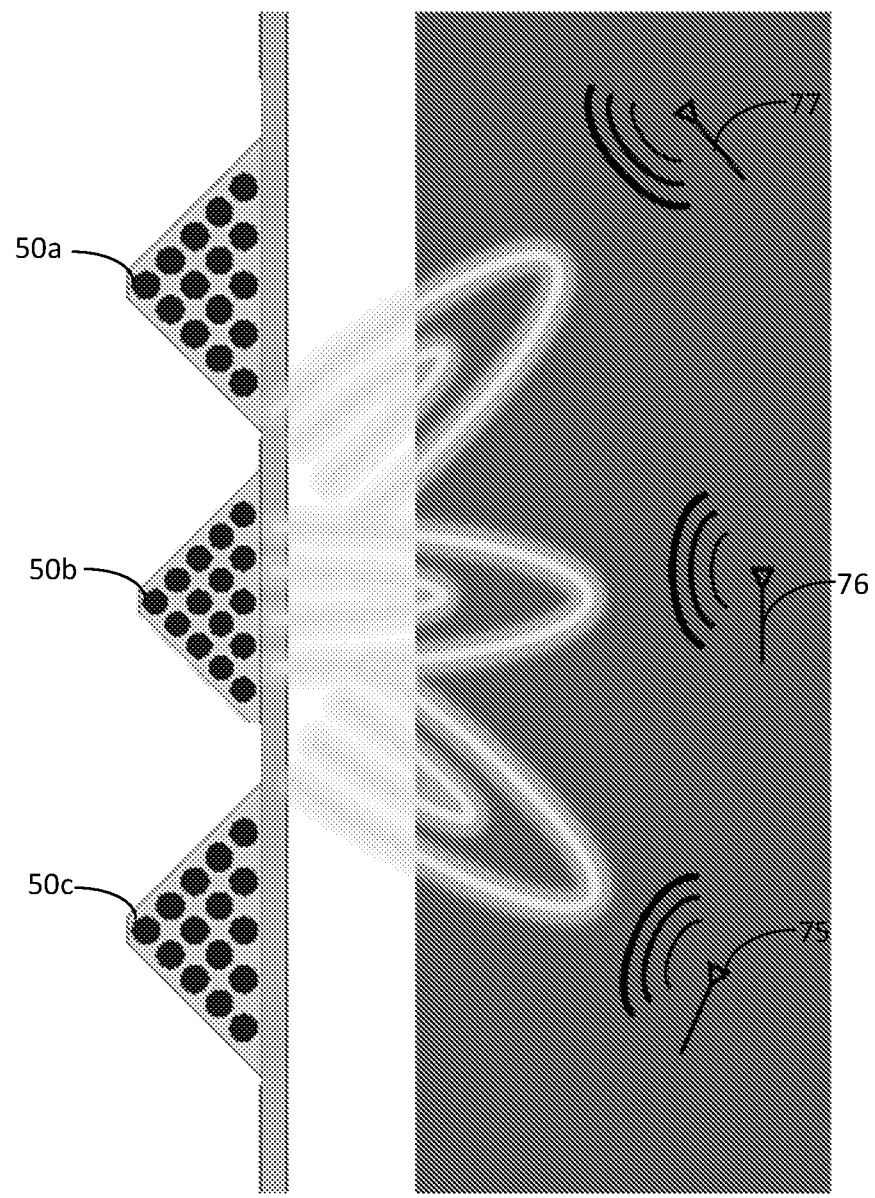
FIG. 35 is a pictorial illustration of an array of the BMAs employed with multiple implant devices in accordance with a representative embodiment.

FIG. 35 is a pictorial illustration of an array of the BMAs 50a, 50b and 50c employed with multiple implant devices 75-77 in accordance with a representative embodiment. The antenna array 50a, 50b and 50c can be used for higher spatial resolution and beamforming (tuning of beam direction and improving antenna directivity). It can also be used to ensure all-time communication with the implants despite potential misalignments.

Figure 36:
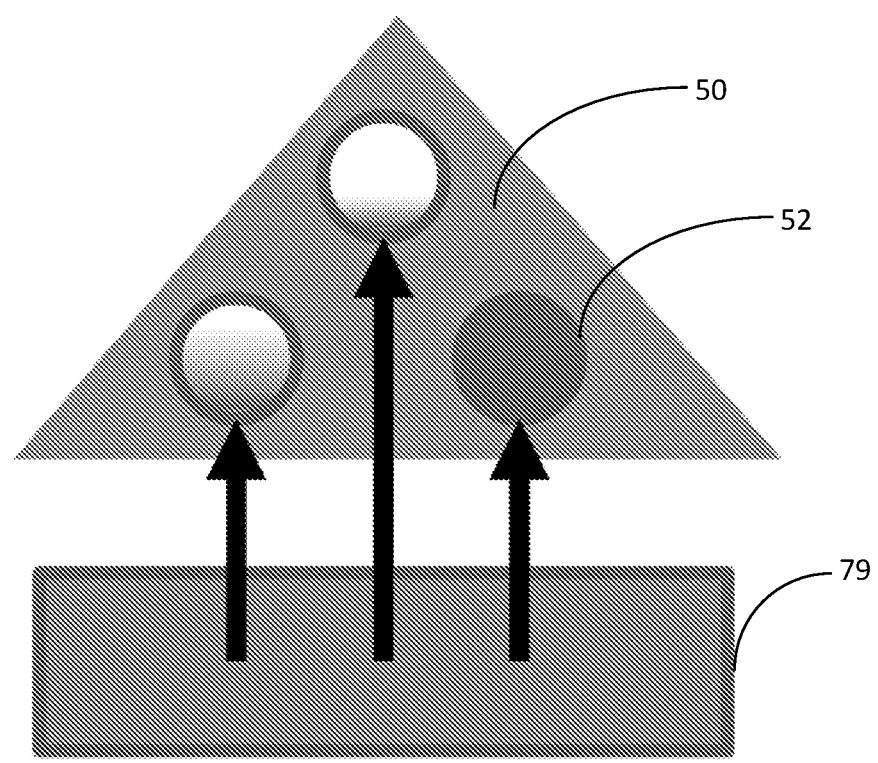
FIG. 36 is a side plan view of the BMA in accordance with another representative embodiment in which a pump is used to control the amount of water that is disposed in the holes in order to vary the permittivity of the antenna.

FIG. 36 is a side plan view of the BMA 50 in accordance with another representative embodiment in which a pump 79 is used to control the amount of water that is disposed in the holes 52 in order to vary the permittivity of the BMA 50. Variations in patient body composition as well as environmental differences can change the permittivity of the patient. Microchannel water pumping of the BMA 50 can be used to control the permittivity of the BMA 50 to ensure that it closely matches the permittivity of the patient's skin. The same concept can also be used to fine-tune the BMA 50 for different applications (e.g., operation on skin vs. operation on fur vs. operation on hair+skin).

It should also be noted that BMA 50 can be encapsulated with insulating material to prevent it from being directly affected by environmental temperatures that may change its permittivity. Also, materials other than distilled water that are more tolerant to extreme temperatures may be disposed in the holes 52.

Figure 37:
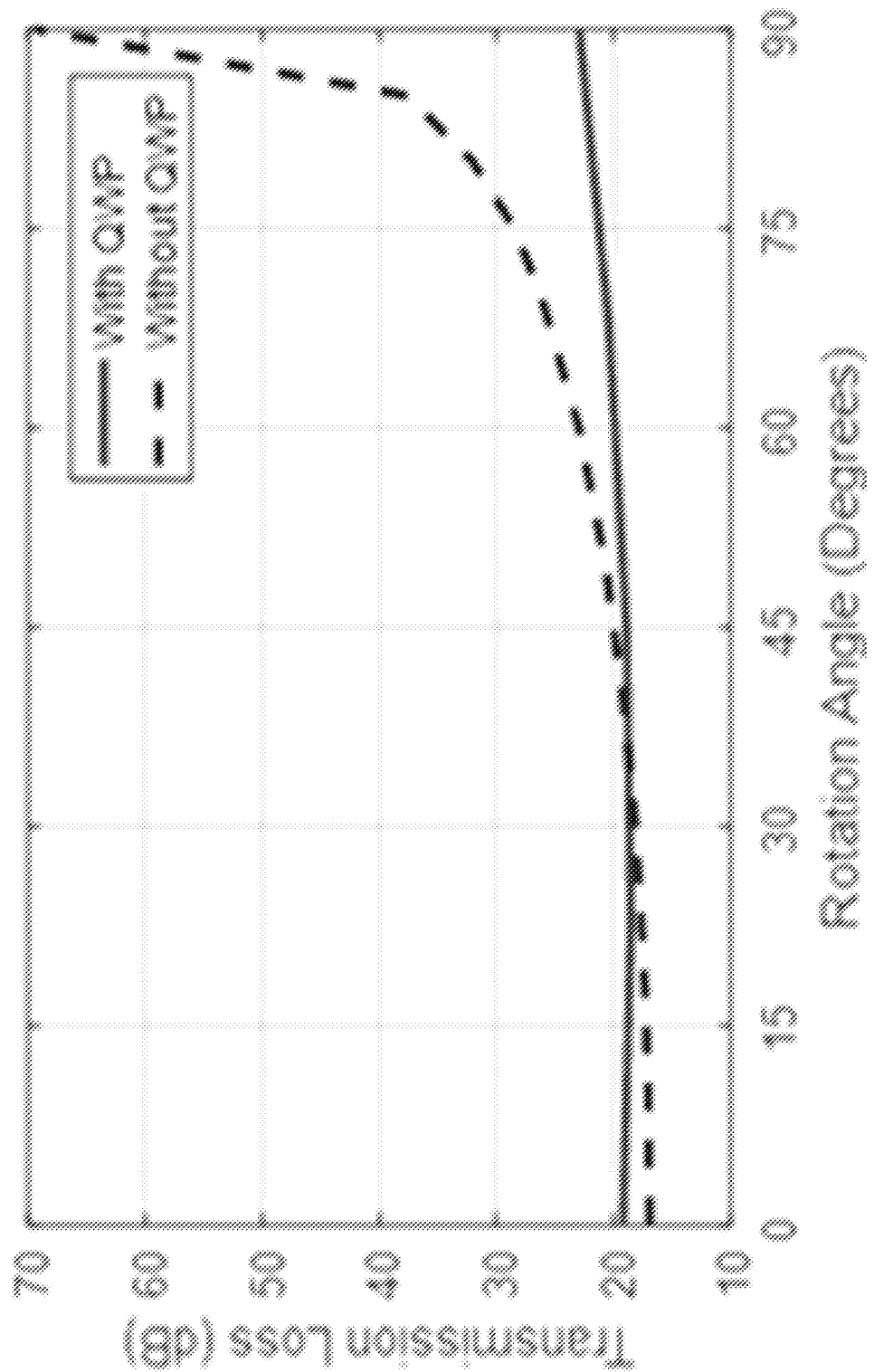
FIG. 37 is a plot of transmission loss at 2.4 GHz between a BMA and a 20-mm-deep implant vs. rotational misalignment when the BMA is used with and without a quarter-wave transformer lens.

FIG. 37 is a plot of transmission loss at 2.4 GHz between a BMA and a 20-mm-deep implant vs. rotational misalignment when the BMA is used with and without a quarter-wave transformer lens. As indicated above with reference to FIG. 27, the BMA typically maintains a linear polarization that causes it to be dependent on rotational alignment. Indeed, simulation results shown in FIG. 37 (dotted line plot) the transmission loss between the aforementioned antenna and a 20 mm-deep implanted patch. As the BMA rotates about its central axis, transmission loss degrades significantly. For rotational misalignment by up to 45°, loss remains within 3 dB of the perfectly matched polarization. At an angular offset of about 90°, however, losses increase by as much as 70 dB. Expectedly, for realistic scenarios where rotational misalignment cannot be precisely controlled, it is highly beneficial to develop BMAs that are circularly polarized.

In accordance with a representative embodiment, a lensing approach is implemented with the BMA that comprises using a quarter-wave plate transformer with the BMA to convert linear polarization into circular polarization. The lensing approach relies on birefringence concepts that have traditionally been used in optics to change the polarization of light. It is believed that the present disclosure is the first to disclose leveraging birefringence to develop polarization-transforming lenses in RF antenna design. Specifically, the quarter-wave plate transformer acts as a lens that shifts the phase between two perpendicular polarizations of the wave. In particular, the quarter-wave plate transformer provides a/2 phase delay, changing linearly polarized waves to circular polarized waves. A proof-of-concept simulation involved placing a quarter-wave plate lens directly under a BMA of the type shown in FIG. 15 (conical). Simulation results for the BMA rotating upon the lens are superimposed in FIG. 37 (solid line). As seen, the design is now much more rotationally robust-note that it still shows more as elliptically rather than circularly polarized.

VII. Conclusions

In conclusion, a few examples of BMAs have been presented in this disclosure as a new class of wearable, into-body radiators that employ periodic unit cells made of plastic and water to exceed state-of-the-art bandwidth and transmission performance.

In accordance with a representative embodiment, the BMA is configured for use in low-loss biomedical telemetry with wireless implants (first experimental setup and FIGS. 15-29). The BMA was shown to operate in the entire 1 to 9 GHz bandwidth, and its performance was thoroughly explored in the commonly used 2.4 GHz ISM band. The antenna's effective permittivity, enabled by the use of both water and plastic, has been engineered to closely match the permittivity of biological tissues over the entire bandwidth. With this uniquely engineered permittivity, the antenna was able to overcome conventional challenges of on-body antennas (mismatch vs. the high-permittivity biological tissue, varying tissue properties with frequency, and inter-subject/environmental variances of biological tissues).

Simulation and measurement results indicated that the BMA of the first experimental setup offers versatile communication capabilities for both subcutaneous and deep-tissue implants. The recorded transmission loss was remarkable and improved by 14.5 dB and 10.8 dB vs. the state-of-the-art for subcutaneous (4-mm-deep) and deep-tissue (2-cm-deep) telemetry, respectively. The antenna was also shown to be relatively robust to both rotational and positional misalignments. It can be rotationally misaligned by up to 45° and remain within 3 dB of the ideal transmission. It can also be positionally misaligned by up to ~1 cm and remain within 3 dB of optimal power transfer. Finally, the antenna was found to conform to FCC SAR standards for input power levels as high as 8.57 dBm.

Overall, the BMA demonstrated by the first experimental setup brings forward transformational opportunities for biomedical telemetry with wireless implants and the potential for integrating this antenna in communication systems to various implanted medical sensors, stimulators, and/or energy harvesters.

With respect to the second experimental setup and FIGS. 1-14 and 30A-37, a few examples of BMAs have been presented as a new class of wearable, into-body radiators that employ periodic unit cells made of plastic and water to exceed state-of-the-art bandwidth and transmission performance. The PWEM method was employed to derive the effective bio-matched dielectric properties, and design equations were derived for the high and low frequency cutoffs in terms of the BMA geometry. Effects of varying unit cells (cylindrical, rectangular, and hexagonal) were also discussed. Assuming homogeneous tissue media, the general trends of BMA design were shown, which can be fine-tuned for various anatomical locations. Building on this theoretical framework, novel BMAs were designed, fabricated, and tested with nearly twice the bandwidth and 6.2 dB less transmission loss across 3 cm of phantom material than the most wideband and most efficient into-body radiator previously reported.

The remarkably wide bandwidth and high gain demonstrated in this disclosure offer new opportunities for medical radiometry and telemetry. This could allow for high resolution in medical thermal imaging, high data rates in implant communication, advancement of multi-channel in-body medical device networks, and other advancements in the exciting intersection of electromagnetics and medicine.

Aspects According to the Inventivre Principles and Concepts

In accordance with one aspect, a BMA adapted to be attached to a body of a living subject comprises at least a first antenna element, at least a second material disposed in or on the first antenna element and an electrically-conductive material at least partially covering at least a first side of the first antenna element. The first antenna element is configured to receive an oscillating electric current and to radiate an oscillating electromagnetic field over a predetermined range of frequencies. The oscillating electromagnetic field has a predetermined beam shape and directionality. The first antenna element comprises at least a first non-electrically-conductive material having a first relative permittivity. The second material has a second relative permittivity. Disposing the second material on or in the first antenna element at one or more predetermined locations provides the first antenna element with an effective permittivity that is closely matched, over the predetermined range of frequencies, to a frequency-dependent permittivity of biological tissue of a body of a living subject.

In accordance with another aspect, the first non-electrically-conductive material is dielectric material engineered such that the first and second relative permittivities achieve anisotropy.

In accordance with another aspect, the first antenna element is a quasi-conical antenna element, and the first non-electrically-conductive material is formed into a pyramidal-shaped structure.

In accordance with another aspect, the first non-electrically-conductive material has a relative permittivity that is in a range of between 1.0 and 10.0.

In accordance with another aspect, the first non-electrically-conductive material comprises polylactic acid (PLA) and has a relative permittivity that is greater than or equal to 3.0 and less than or equal to 4.0.

In accordance with another aspect, the second material has a relative permittivity that is in a range of between 50.0 and 90.0.

In accordance with another aspect, the second material comprises water, such as distilled water or hydrogels, for example.

In accordance with another aspect, the second material is disposed in holes formed in at least a first side of the pyramidal-shaped structure. The first side of the pyramidal-shaped structure is the first side of the first antenna element that is at least partially covered with the electrically-conductive material.

In accordance with another aspect, the holes are at least one of cylindrically-shaped, rectangularly-shaped and hexagonally-shaped holes that are evenly spaced apart from one another.

In accordance with another aspect, the electrically-conductive material comprises electrically-conductive tape. The first side of the pyramidal-shaped structure and a second side of the pyramidal-shaped structure opposite the first side of the pyramidal-shaped structure are at least partially covered with first and second strips of the electrically-conductive tape, respectively. The first and second strips of tape prevent the second material disposed in the holes from passing out of the holes.

In accordance with another aspect, the first and second strips of tape are strips of copper tape, and the first and second strips of tape act as first and second flares, respectively, of the quasi-conical antenna element.

In accordance with another aspect, the predetermined range of frequencies includes frequencies ranging from 400 Megahertz (MHz) to 12 Gigahertz (GHz).

In accordance with another aspect, the BMA further comprises a buffer lens comprising the first non-electrically-conductive material having the first relative permittivity and the second material having the second relative permittivity. The buffer lens increases a maximum allowable input power of the BMA.

In accordance with another aspect, the BMA further comprises a quarter-wave plate transformer electromagnetically coupled with the BMA. The quarter-wave plate transformer acts as a lens that shifts a phase between two perpendicular polarizations of the oscillating electromagnetic field radiated by the BMA by $\pi/2$.

In accordance with another aspect, the BMA comprises a quasi-conical antenna element, a material disposed inside of the holes that has a second relative permittivity that ranges from about 40 to 90 and an electrically-conductive material at least partially covering at least a first side of the pyramidal-shaped structure. The quasi-conical antenna element is configured to receive an oscillating electric current and to radiate an oscillating electromagnetic field over a predetermined range of frequencies. The oscillating electromagnetic field has a predetermined beam shape and directionality. The quasi-conical antenna element is made of a non-electrically-conductive dielectric material having a first relative permittivity that ranges from about 1.0 to 10.0. The non-electrically-conductive dielectric material is formed into a pyramidal-shaped structure. At least a first side of the pyramidal-shaped structure having a plurality of holes formed therein. The material having the second relative permittivity is inside of the holes. Disposing the material inside of the holes provides the quasi-conical antenna element with an effective permittivity that is closely matched, over the predetermined range of frequencies, to a frequency-dependent permittivity of biological tissue of a body of a living subject.

In accordance with another aspect, the non-electrically-conductive dielectric material is a plastic material.

In accordance with another aspect, the plastic material comprises polylactic acid (PLA) having a relative permittivity that is greater than or equal to 3.0 and less than or equal to 4.0.

In accordance with another aspect, the material disposed inside of the holes comprises water having a fill factor, and the fill factor is preselected to affect an input impedance of the BMA.

In accordance with another aspect, the holes are through holes that extend from the first side of the pyramidal-shaped structure to a second side of the pyramidal-shaped structure.

In accordance with another aspect, the holes are at least one of cylindrically-shaped, rectangularly-shaped and hexagonally-shaped holes that are symmetrically positioned.

In accordance with another aspect, the electrically-conductive material comprises electrically-conductive tape. The first and second sides of the pyramidal-shaped structure are at least partially covered with first and second strips of the tape, respectively. The first and second strips of tape prevent the material disposed in the holes from passing out of the holes.

In accordance with another aspect, the first and second strips of tape are strips of copper tape. The first and second strips of copper tape act as first and second flares, respectively, of the BMA. The first and second flares have flare angles that are preselected to affect an input impedance of the BMA.

In accordance with another aspect, the predetermined range of frequencies includes frequencies ranging from 400 MHz to 12 Gigahertz GHz.

In accordance with another aspect, the BMA further comprises a buffer lens comprising the non-electrically-conductive material having the first relative permittivity and the material having the second relative permittivity. The buffer lens increases a maximum allowable input power of the BMA.

In accordance with another aspect, the BMA further comprises a quarter-wave plate transformer electromagnetically coupled with the BMA. The quarter-wave plate transformer acts as a lens that shifts a phase between two perpendicular polarizations of the oscillating electromagnetic field radiated by the BMA by $\pi/2$.

It should be emphasized that the above-described embodiments of the present invention are merely possible examples of implementations, merely set forth for a clear understanding of the principles of the invention. For example, while the experiment was described with reference to a quasi-horn/conical antenna having a particular configuration, other types of antennas (e.g., patch antennas) with suitable configurations may be used. Many variations and modifications may be made to the above-described embodiments of the invention without departing scope of the invention. All such modifications and variations are intended to be included herein within the scope of this disclosure and the present invention.

What is claimed is:

1. A bio-matched antenna (BMA) adapted to be attached to a body of a living subject, the BMA comprising:
    at least a first antenna element configured to receive an oscillating electric current and to radiate an oscillating electromagnetic field over a predetermined range of frequencies, the oscillating electromagnetic field having a predetermined beam shape and directionality, said at least a first antenna element comprising at least a first non-electrically-conductive material having a first relative permittivity;
    at least a second material disposed on or in the first antenna element at one or more predetermined locations on or in the first antenna element, the second material having a second relative permittivity, wherein disposing the second material on or in the first antenna element at one or more predetermined locations provides the first antenna element with an effective permittivity that is closely matched, over the predetermined range of frequencies, to a frequency-dependent permittivity of biological tissue of a body of a living subject;
    a buffer lens comprising the first non-electrically-conductive material having the first relative permittivity and the second material having the second relative permittivity, the buffer lens increasing a maximum allowable input power of the BMA; and
    an electrically-conductive material at least partially covering at least a first side of the first antenna element.

2. The BMA of claim 1, wherein the first non-electrically-conductive material is dielectric material engineered such that the first and second relative permittivities achieve anisotropy.

3. The BMA of claim 2, wherein the first antenna element is a quasi-conical antenna element, and wherein the first non-electrically-conductive material is formed into a pyramidal-shaped structure.

4. The BMA of claim 3, wherein the first non-electrically-conductive material has a relative permittivity that is in a range of between 1.0 and 10.0.

5. The BMA of claim 4, wherein the first non-electrically-conductive material comprises polylactic acid (PLA) and the relative permittivity is greater than or equal to 3.0 and less than or equal to 4.0.

6. The BMA of claim 4, wherein the second material has a relative permittivity that is in a range of between 50.0 and 90.0.

7. The BMA of claim 5, wherein the second material comprises water.

8. The BMA of claim 7, wherein the second material is disposed in holes formed in at least a first side of the pyramidal-shaped structure, the first side of the pyramidal-shaped structure being the first side of the first antenna element.

9. The BMA of claim 8, wherein the holes are at least one of cylindrically-shaped, rectangularly-shaped and hexagonally-shaped holes that are evenly spaced apart from one another.

10. The BMA of claim 9, wherein said electrically-conductive material comprises electrically-conductive tape, and wherein the first side of the pyramidal-shaped structure and a second side of the pyramidal-shaped structure opposite the first side of the pyramidal-shaped structure are at least partially covered with first and second strips of the electrically-conductive tape, respectively, the first and second strips of electrically-conductive tape preventing the second material disposed in the holes from passing out of the holes.

11. The BMA of claim 10, wherein the first and second strips of electrically-conductive tape are strips of copper tape, and wherein the first and second strips of electrically-conductive tape act as first and second flares, respectively, of the quasi-conical antenna element.

12. The BMA of claim 1, wherein the predetermined range of frequencies includes frequencies ranging from 400 Megahertz (MHz) to 12 Gigahertz (GHz).

13. The BMA of claim 1, further comprising:
    a quarter-wave plate transformer electromagnetically coupled with the BMA, the quarter-wave plate transformer acting as a lens that shifts a phase between two perpendicular polarizations of the oscillating electromagnetic field radiated by the BMA by $\pi/2$.

14. A bio-matched antenna (BMA) adapted to be attached to a body of a living subject, the BMA comprising:
    a quasi-conical antenna element configured to receive an oscillating electric current and to radiate an oscillating electromagnetic field over a predetermined range of frequencies, the oscillating electromagnetic field having a predetermined beam shape and directionality, the quasi-conical antenna element being made of a non-electrically-conductive dielectric material having a first relative permittivity that ranges from about 1.0 to 10.0, the non-electrically-conductive dielectric material being formed into a pyramidal-shaped structure, at least a first side of the pyramidal-shaped structure having a plurality of holes formed therein;
    a material disposed inside of the plurality of holes that has a second relative permittivity that ranges from about 40 to 90, wherein disposing the material inside of the plurality of holes provides the quasi-conical antenna element with an effective permittivity that is closely matched, over the predetermined range of frequencies, to a frequency-dependent permittivity of biological tissue of a body of a living subject;
    a buffer lens comprising the non-electrically-conductive material having the first relative permittivity and the material having the second relative permittivity, the buffer lens increasing a maximum allowable input power of the BMA; and
    an electrically-conductive material at least partially covering at least a first side of the pyramidal-shaped structure.

15. The BMA of claim 14, wherein the predetermined range of frequencies includes frequencies ranging from 400 Megahertz (MHz) to 12 Gigahertz (GHz).

16. The BMA of claim 15, wherein the non-electrically-conductive dielectric material is a plastic material.

17. The BMA of claim 16, wherein the plastic material comprises polylactic acid (PLA) having a relative permittivity that is greater than or equal to 3.0 and less than or equal to 4.0.

18. The BMA of claim 17, wherein material disposed inside of the plurality of holes comprises water having a fill factor, the fill factor being preselected to affect an input impedance of the BMA.

19. The BMA of claim 18, wherein the plurality of holes are through holes that extend from the first side of the pyramidal-shaped structure to a second side of the pyramidal-shaped structure.

20. The BMA of claim 19, wherein the plurality of holes are at least one of cylindrically-shaped, rectangularly-shaped and hexagonally-shaped holes that are symmetrically positioned.

21. The BMA of claim 20, wherein said electrically-conductive material comprises electrically-conductive tape, and wherein the first side and the second side of the the pyramidal-shaped structure are at least partially covered with first and second strips of the electrically-conductive tape, respectively, the first and second strips of electrically-conductive tape preventing the material disposed in the plurality of holes from passing out of the plurality of holes.

22. The BMA of claim 21, wherein the first and second strips of electrically-conductive tape are strips of copper tape, and wherein the first and second strips of copper tape act as first and second flares, respectively, of the BMA, the first and second flares having flare angles that are preselected to affect an input impedance of the BMA.

23. A bio-matched antenna (BMA) adapted to be attached to a body of a living subject, the BMA comprising:
a quasi-conical antenna element configured to receive an oscillating electric current and to radiate an oscillating electromagnetic field over a predetermined range of frequencies, the oscillating electromagnetic field having a predetermined beam shape and directionality, the quasi-conical antenna element being made of a non-electrically-conductive dielectric material having a first relative permittivity that ranges from about 1.0 to 10.0, the non-electrically-conductive dielectric material being formed into a pyramidal-shaped structure, at least a first side of the pyramidal-shaped structure having a plurality of holes formed therein;
a material disposed inside of the plurality of holes that has a second relative permittivity that ranges from about 40 to 90, wherein disposing the material inside of the plurality of holes provides the quasi-conical antenna element with an effective permittivity that is closely matched, over the predetermined range of frequencies, to a frequency-dependent permittivity of biological tissue of a body of a living subject;
an electrically-conductive material at least partially covering at least a first side of the pyramidal-shaped structure; and
a quarter-wave plate transformer electromagnetically coupled with the BMA, the quarter-wave plate transformer acting as a lens that shifts a phase between two perpendicular polarizations of the oscillating electromagnetic field radiated by the BMA by $\pi/2$.

24. The BMA of claim 23, wherein said electrically-conductive material comprises electrically-conductive tape, and wherein the first side and the second side of the pyramidal-shaped structure are at least partially covered with first and second strips of the electrically-conductive tape, respectively, the first and second strips of electrically-conductive tape preventing the material disposed in the plurality of holes from passing out of the plurality of holes.

25. The BMA of claim 24, wherein the first and second strips of electrically-conductive tape are strips of copper tape, and wherein the first and second strips of copper tape act as first and second flares, respectively, of the BMA, the first and second flares having flare angles that are preselected to affect an input impedance of the BMA.

* * * * *